US012203083B2

(12) United States Patent
Bayer et al.

(10) Patent No.: US 12,203,083 B2
(45) Date of Patent: *Jan. 21, 2025

(54) PROGRAMMABLE EPIGENETIC CONTROL OF GENE EXPRESSION IN PLANTS

(71) Applicant: Sound Agriculture Company, Emeryville, CA (US)

(72) Inventors: Travis Bayer, Emeryville, CA (US); Kevin L. Schneider, Emeryville, CA (US); Aden Kinne, Emeryville, CA (US); Jennifer Adele Samson, Emeryville, CA (US); Itxaso Garay, Emeryville, CA (US)

(73) Assignee: DECIBEL BIO, INC, Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/169,601

(22) Filed: Feb. 15, 2023

(65) Prior Publication Data

US 2023/0304028 A1  Sep. 28, 2023

Related U.S. Application Data

(63) Continuation of application No. 17/476,097, filed on Sep. 15, 2021, now Pat. No. 11,591,608, which is a continuation of application No. PCT/US2020/023391, filed on Mar. 18, 2020.

(60) Provisional application No. 62/820,172, filed on Mar. 18, 2019.

(51) Int. Cl.
    *C12N 15/82* (2006.01)
(52) U.S. Cl.
    CPC ....... *C12N 15/8218* (2013.01); *C12N 15/825* (2013.01); *C12N 15/8262* (2013.01); *C12N 15/8297* (2013.01); *C12N 15/8298* (2013.01)
(58) Field of Classification Search
    None
    See application file for complete search history.

(56) References Cited

U.S. PATENT DOCUMENTS

| 5,795,782 | A | 8/1998 | Church et al. |
|---|---|---|---|
| 9,288,952 | B2 | 3/2016 | Sisson |
| 10,813,311 | B2 | 10/2020 | Kramer |
| 11,812,738 | B2 | 11/2023 | Sammons et al. |
| 2005/0026160 | A1* | 2/2005 | Allerson ................ C07H 21/04 544/243 |
| 2018/0163219 | A1 | 6/2018 | Huang et al. |
| 2019/0024086 | A1 | 1/2019 | Lande et al. |
| 2019/0055555 | A1* | 2/2019 | Hauser ...................... A61K 9/14 |
| 2023/0054672 | A1 | 2/2023 | Berry et al. |

FOREIGN PATENT DOCUMENTS

| CN | 107714685 A | 2/2018 |
|---|---|---|
| CN | 109890962 A | 6/2019 |
| JP | 2013535212 A | 9/2013 |
| WO | 2012018754 A2 | 2/2012 |
| WO | 2014106837 A2 | 7/2014 |
| WO | 2014106838 A2 | 7/2014 |
| WO | 2020191072 A1 | 9/2020 |

OTHER PUBLICATIONS

Chi et al. BMC Plant Biology. 14(62): 1-18. (Year: 2014).*
Aufsatz et al., "RNA-directed DNA methylation in *Arabidopsis*", Proceedings of the National Academy of Sciences, vol. 99, No. 4, Dec. 10, 2002, pp. 16499-16506.
Ca3,129,708 , "Office Action", Aug. 22, 2023, 6 pages.
SG11202110204S , "Search Report and Written Opinion", Aug. 9, 2023, 11 pages.
Application No. PCT/US2020/023391, International Search Report and Written Opinion, mailed Jul. 6, 2021, 10 pages.
Application No. PCT/US2022/073384, International Search Report and Written Opinion, mailed Oct. 14, 2022, 15 pages.
Application No. EP20773409.6, Extended European Search Report, mailed Nov. 17, 2022, 6 pages.
"Solanum Lycopersicum Chromosome Ch07, Complete Genome", NCBI, GenBank: HG975519.1., Nov. 17, 2015, 1 page.
Bhagwat et al., "An in Vivo Transient Expression System can be Applied for Rapid and Effective Selection of Artificial Micro RNA Constructs for Plant Stable Genetic Transformation", Journal of Genetics and Genomics, vol. 40, No. 5, May 20, 2013, pp. 261-270.
Chi et al., "Reduced Polyphenol Oxidase Gene Expression and Enzymatic Browning in Potato (*Solanum tuberosum* L.) with Artificial MicroRNAs", BMC Plant Biology, vol. 14, No. 62, Mar. 11, 2014, pp. 1-18.
Ecker, "Epigenetic Trigger for Tomato Ripening", Nature Biotechnology, vol. 31, No. 2, Feb. 2013, 4 pages.
Finnegan et al., "DNA Methylation in Plants", Annual Review of Plant Physiology and Plant Molecular Biology, vol. 49, Jun. 1998, pp. 223-247.
Gebala et al., "Quantitative Studies of an RNA Duplex Electrostatics by Ion Counting", Biophysical Journal, vol. 117, Sep. 17, 2019, pp. 1116-1124.
Hermann et al., "RNA Bulges as Architectural and Recognition Motifs", Structure, vol. 8, No. 3, 2000, pp. R47-R54.
Horesh et al., "A Rapid Method for Detection of Putative RNAi Target Genes in Genomic Data", Bioinformatics, vol. 19, Nov. 2003, pp. ii73-ii80.
Lennox et al., "Chemical Modification and Design of Anti-miRNA Oligonucleotides", Gene Therapy, vol. 18, No. 12, Jul. 14, 2011, pp. 1111-1120.
Liu et al., "SIGRAS4 Accelerates Fruit Ripening by Regulating Ethylene Biosynthesis Genes and SIMADS1 in Tomato", Horticulture Research., vol. 8, No. 3, Jan. 1, 2021, pp. 1-11.

(Continued)

*Primary Examiner* — Mykola V. Kovalenko
*Assistant Examiner* — David R Byrnes
(74) *Attorney, Agent, or Firm* — Kilpatrick Townsend & Stockton LLP

(57) ABSTRACT

Disclosed herein are artificially synthesized nucleic acid constructs to guide an epigenetic modification for at least partially silencing or activating a target gene in an organism such as a plant or seed, and formulations thereof. Also disclosed are methods of applying such nucleic acid constructs to the plant or to the seed. Also disclosed are engineered seeds and plants obtained by the epigenetic modification.

14 Claims, 11 Drawing Sheets

Specification includes a Sequence Listing.

(56) References Cited

OTHER PUBLICATIONS

Ma et al., "Angiosperms Are Unique among Land Plant Lineages in the Occurrence of Key Genes in the RNA-Directed DNA Methylation (RdDM) Pathway", Genome Biology and Evolution, vol. 7, No. 9, Sep. 2, 2015, pp. 2648-2662.

Marienssen et al., "DNA Methylation and Epigenetic Inheritance in Plants and Filamentous Fungi", Science, vol. 293, No. 5532, Aug. 10, 2001, pp. 1070-1074.

Richmond et al., "The Structure of DNA in the Nucleosome Core", Nature, vol. 423, May 8, 2003, pp. 145-150.

Smalheiser et al., "Mammalian Argonaute-DNA Binding?", Biology Direct, vol. 9, No. 27, Dec. 2014, pp. 1-11.

Tanaka et al., "A'-form RNA Double helix in the Single Crystal Structure of r(UGAGCUUCGGCUC)", Nucleic Acids Research, vol. 27, No. 4, 1999, pp. 949-955.

Wang et al., "Mutual Regulation of MicroRNAs and DNA Methylation in Human Cancers", Epigenetics, vol. 12, No. 3, Mar. 4, 2017, pp. 187-197.

Xie et al., "siRNA-Directed DNA Methylation in Plants", Current Genomics, vol. 16 , No. 1, Feb. 2015, pp. 23-31.

Yoshizumi et al., "Selective Gene Delivery for Integrating Exogenous DNA into Plastid and Mitochondrial Genomes Using Peptide-DNA Complexes", Biomacromolecules, vol. 19, No. 15, 2018, pp. 1582-1591.

Yu et al., "Methylation as a Crucial Step in Plant MicroRNA Biogenesis", Science, vol. 307, No. 5711, Feb. 11, 2005, pp. 932-935.

Zhang et al., "Dynamics and Function of DNA Methylation in Plants", Nature Reviews: Molecular Cell Biology, vol. 19, Aug. 2018, pp. 489-506.

Zhang et al., "The SlFSR Gene Controls Fruit Shelf-Life in Tomato", Journal of Experimental Botany, vol. 69, No. 12, Apr. 4, 2018, pp. 2897-2909.

SG11202110204S , "Written Opinion", Sep. 28, 2023.

PCT/US2022/073384 , "International Preliminary Report on Patentability", Jan. 11, 2024, 11 pages.

Altschul , et al., "Basic Local Alignment Search Tool", Journal of Molecular Biology, vol. 215, 1990, pp. 403-410.

Ashapkin , et al., "Epigenetic variability in plants: Heritability, Adaptability, Evolutionary significance", Russian Journal of Plant Physiology, vol. 63, No. 2, 2016, pp. 181-192.

Batzer , et al., "Enhanced Evolutionary PCR Using Oligonucleotides with Inosine at the 3'-Terminus", Nucleic Acids Research, vol. 19, No. 18, Sep. 25, 1991, 1 page.

Karlin , et al., "Applications and Statistics for Multiple High-Scoring Segments in Molecular Sequences", Proceedings of the National Academy of Sciences USA, vol. 90, No. 12, Jun. 15, 1993, pp. 5873-5877.

Krueger , et al., "Bismark: A Flexible Aligner and Methylation Caller for Bisulfite-Seq Applications", Bioinformatics, vol. 27, No. 11, Jun. 1, 2011, pp. 1571-1572.

Mahajan , et al., "Postharvest Treatments of Fresh Produce", Philosophical Transactions of The Royal Society A, vol. 372, No. 2017, 2017, 19 pages.

Nambeesan , et al., "Overexpression of yeast spermidine synthase impacts ripening, senescence and decay symptoms in tomato", The Plant Journal, 63(5), Sep. 2010, pp. 836-847.

Rossolini , et al., "Use of Deoxyinosine-Containing Primers Vs Degenerate Primers for Polymerase Chain Reaction Based on Ambiguous Sequence Information", Molecular and Cellular Probes, vol. 8, No. 2, Apr. 1994, pp. 91-98.

Smith , et al., "Comparison of Biosequences", Advances in Applied Mathematics, vol. 2, No. 4, Dec. 1981, pp. 482-489.

* cited by examiner

SEQ ID NO: 289/290

TCAAAACCTCCCACCTACGGGmU
CGCGGTAGGTGGGAGGTTTTTTGAmA
TpCpApApApApApCpTpCpCpApCpCpTpApCpGpGpApmA
CpGpCpGpGpTpApGpGpTpGpGpGpApGpGpTpTpTpTpTpTpGpApmA

Example of 100% backbone modified (fN = 2'Fluoro, mN = 2'O-Methyl, s = phosphorothioate)

mUsmCsfApmApfApmApfApmCpfCpmApfCpmCpfGpmApfGpmGpfApmGpfGpmUpfUpmUpfGsmAsmA
fCsfGsmCpfGpmCpfGpfUpmApfGpmGpfUpmGpfGpmCpfGpmCsmGsmU

Example of PS linkage placement (s = PS)

TsCpApApApApApCpTpCpCpApCpCpTpApCpGpGpAps

PROGRAMMABLE EPIGENETIC CONTROL OF GENE EXPRESSION IN PLANTS

CROSS-REFERENCE

The present application is a continuation of U.S. Nonprovisional application Ser. No. 17/476,097, filed Sep. 15, 2021, which is a continuation of PCT/US2020/023391, filed Mar. 18, 2020, which claims the benefit of U.S. Provisional Application Ser. No. 62/820,172, filed Mar. 18, 2019, each of which are hereby incorporated by reference in their entirety.

SEQUENCE LISTING

The instant application contains a Sequence Listing in XML format. The Sequence Listing, named 1370744.xml, was created on Feb. 15, 2023, is 583 Kilobytes in size, and is hereby incorporated by reference in its entirety.

BRIEF SUMMARY

In some aspects, disclosed herein is a nucleic acid construct, e.g., a polynucleotide. In some instances, the present disclosure provides an artificial nucleic acid construct, wherein the artificial nucleic acid construct comprises: (a) a ribose modified at a 2' or 3' position, or a deoxyribose modified at a 2' or 3' position, or a combination thereof; and (b) a terminal end overhang, wherein: the artificial nucleic acid construct is double stranded; at least one strand of the artificial nucleic acid construct independently comprises a length from at least: about 10 to about 30 nucleotides or nucleosides or a combination thereof; and when contacted with an organism, at least a portion of the artificial nucleic acid construct is configured to facilitate: i) an epigenetic modification of at least one base of a nucleotide or nucleoside in a nucleic acid sequence of the organism, ii) a silencing of a target mRNA sequence that is at least partially complementary to the at least one strand of the artificial nucleic acid construct, iii) a cleavage of the target mRNA sequence, or iv) any combination of i), ii), or iii). In some instances, the artificial nucleic acid construct comprises no epigenetic modification on any purine or pyrimidine base of a nucleotide or nucleoside. In some instances, the artificial nucleic acid construct facilitates the epigenetic modification through a system that at least in part comprises a DNA methyltransferase, a biologically active fragment thereof, or a derivative thereof. In some instances, the artificial nucleic acid construct facilitates the epigenetic modification through a system that at least in part comprises a DNA acetyltransferase, a biologically active fragment thereof, or a derivative thereof. In some instances, the system comprises at least a portion of at least one component of an RNA directed DNA methylation pathway. In some instances, the at least one component comprises a protein or a portion thereof. In some instances, the protein or portion thereof is an enzyme or a portion thereof. In some instances, the artificial nucleic acid construct is capable of facilitating the epigenetic modification in the absence of a CRISPR, a CRISPR-associated protein (Cas), a biologically active fragment thereof, a derivative thereof, a fusion protein thereof, or any combination thereof. In some instances, the artificial nucleic acid construct is capable of facilitating the epigenetic modification in the absence of a Cas that comprises Cas1, Cas2, Cas3, Cas4, Cas5, Cas6, Cas7, Cas8, Cas9, or any combination thereof. In some instances, at least about 80% of sugars of the artificial nucleic acid construct, based on a total number of the sugars, each independently comprises a deoxyribose, modified deoxyribose, or a combination thereof. In some instances, less than about 20% of sugars of the artificial nucleic acid construct, based on a total number of the sugars, each independently comprises a ribose, a modified ribose, or a combination thereof. In some instances, the artificial nucleic acid construct is at least partially encoded by an RNA or DNA: nucleotide or nucleoside, or a combination thereof. In some instances, at least about 80% of the nucleotides, nucleosides, or a combination thereof of the artificial nucleic acid construct are DNAs. In some instances, a terminal nucleotide or terminal nucleoside of the artificial nucleic acid construct comprises an RNA: nucleotide or nucleoside, or a combination thereof. In some instances, multiple nucleotides in the nucleic acid sequence have the same epigenetic modification. In some instances, at least 10-12 nucleotides in the nucleic acid sequence have the same epigenetic modification. In some instances, the nucleic acid sequence comprises at least about 100 contiguous nucleotides. In some instances, the nucleic acid sequence comprises a CpG island. In some instances, the modified ribose or the modified deoxyribose is at a terminal nucleotide or nucleoside of the artificial nucleic acid construct. In some instances, the modified ribose or the modified deoxyribose comprises a 2'-O—R group. In some instances, R group is selected from the group consisting of: an alkyl, an aryl, a haloalkyl, an amino, a methyl, acetyl, and a halo. In some instances, the R group is the methyl. In some instances, the artificial nucleic acid construct further comprises a modification in at least one of a purine or pyrimidine base. In some instances, the modification comprises a plurality of modifications. In some instances, the modification increases stability of the artificial nucleic acid construct. In some instances, the modification increases uptake of the artificial nucleic acid construct by the organism. In some instances, the modification is substantially positioned at a 3' end of the artificial nucleic acid construct. In some instances, the modification is substantially positioned at a 5' end of the artificial nucleic acid construct. In some instances, the modification comprises a methyl group, a methoxy group, an ester group, a fluoro group, a phosphorthioate backbone, or any combination thereof. In some instances, the terminal end overhang is a 3' end overhang. In some instances, the artificial nucleic acid construct comprises two 3' end overhangs. In some instances, at least one strand of the artificial nucleic acid construct independently comprises a length from about 20 to about 30 nucleotides or nucleosides or a combination thereof. In some instances, the artificial nucleic acid construct comprises at least one deoxyribonucleic acid. In some instances, the artificial nucleic acid construct comprises at least one ribonucleic acid. In some instances, the artificial nucleic acid construct comprises at least one strand that is not phosphorylated at its 5' terminus. In some instances, the organism comprises a plant, a seed, a fruit, a leaf, a stalk, a root, a flower, an archaeon, a bacterium, a fungus, a virus, a virus-like particle, a protist, an alga, a nematode, a portion of any of these, or any combination thereof. In some instances, the artificial nucleic acid construct comprises at least about: 80%, 85%, 90%, 95%, or 98%; or about 100% sequence identity or at least 10 contiguous bases of one or more of SEQ ID NOs: 1-62. In some instances, the artificial nucleic acid construct comprises at least about: 80%, 85%, 90%, 95%, or 98%; or about 100% sequence identity or at least 10 contiguous bases of one or more of SEQ ID NOs: 63-194. In some instances, the artificial nucleic acid construct comprises at least about: 80%, 85%, 90%, 95%, or 98%; or about 100% sequence identity or at least 10 contiguous bases of one or more of SEQ ID NOs: 195-404. In some instances, the artificial nucleic acid construct comprises at least about: 80%, 85%, 90%, 95%, or 98%; or about 100% sequence identity or at least 10 contiguous bases of one or more of SEQ ID NOs: 405-584. In some instances, the artificial nucleic acid construct comprises at least about: 80%, 85%, 90%, 95%, or 98%; or about 100% sequence identity or at least 10 contiguous bases of one or more of SEQ ID NOs: 585-684. In some instances, the artificial nucleic acid construct comprises a peptide nucleic acid, a morpholino, a locked nucleic acid, a glycol nucleic acid, a threose nucleic acid, or any combination thereof positioned in the backbone of the artificial nucleic acid construct. In some instances, the epigenetic modification is comprised in a polynucleotide sequence at least partially encoding one or more proteins of Nuclear RNA polymerase D1 (NRPD1), NRPE1, NRPD2/NRPE2, NRPD4/NRPE4, NRPE5, NRPE9B, NRPB1, RNA-Dependent RNA Polymerase 2 (RDR2), DICER-Like 3 (DCL3), HUA Enhancer 1 (HEN1), Argonaute 4 (AGO4), AGO6, AGO9, Classy 1 (CLSY1), Defective in RNA-Directed DNA Methylation 1 (DRD1), Defective in Meristem Silencing 3 (DMS3), RNA-Directed DNA Methylation 1 (RDM1), KOW Domain-Containing Transcription Factor 1 (KTF1), Involved in De Novo 2 (IDN2), IDN2 Paralogue1 (IDP1), IDP2, DMS4, Domains Rearranged Methyltransferase 2 (DRM2), SUVH2, SUVH9, SUVR2, Microrchidia 1 (MORC1), MORC6, Sawadee homeodomain homologue 1 (SHH1), Histone Deacetylase 6 (HDA6), Jumonji 14 (JMJ14), Lysine-specific Histone Demethylase 1 (LDL1), LDL2, Ubiquitin-specific Protease 26 (UBP26), Needed For RDR2-Independent DNA Methylation (NERD), Chromomethylase 2 (CMT2), CMT3, Methyltransferase 1 (MET1), SUVH4, Decreased DNA Methylation 1 (DDM1), a biologically active fragment thereof, a regulatory element associated therewith, an intron associated therewith, or any combination thereof. In some instances, the epigenetic modification is catalyzed by an enzyme or a catalytically or biologically active fragment thereof. In some instances, the enzyme or catalytically or biologically active fragment thereof is endogenous to the organism. In some instances, the enzyme or catalytically or biologically active fragment thereof comprises a TET family enzyme or a catalytically or biologically active fragment thereof. In some instances, the enzyme or catalytically or biologically active fragment thereof comprises a methyltransferase or a catalytically or biologically active fragment thereof. In some instances, the methyltransferase comprises a chromomethyltransferase (CMT), a domain rearranged methyltransferase (DRM), or a combination thereof. In some instances, the epigenetic modification adds a chemical group to the at least one base. In some instances, the epigenetic modification adds a methyl group to the at least one base, and wherein the methyl group is oxidized to a methoxy, formyl, or carboxyl group, or a carboxylic acid. In some instances, the at least one base is a cytosine. In some instances, the epigenetic modification comprises a methyl group, a hydroxymethyl group, a formyl group, a carboxyl group, or any combination thereof. In some instances, the epigenetic modification comprises the methyl group. In some instances, the nucleic acid sequence comprises a transcription regulatory region. In some instances, a strand of the double stranded artificial nucleic acid construct comprises at least about: 80%, 85%, 90%, 95%, or 98%; or about 100% sequence identity to a portion of a transcription regulatory region. In some instances, the transcription regulatory region comprises at least about 30% guanine cytosine (GC) content.

In some aspects, the present disclosure provides a plurality of artificial nucleic acid constructs disclosed herein (double stranded or single stranded), for example at least about: 2-100, 2-90, 2-80, 2-70, 2-60, 2-50, 2-40, 2-30, 2-24, 2-12, 4-100, 4-90, 4-80, 4-70, 4-60, 4-50, 4-40, 4-30, 4-24, 4-12, 6-100, 6-90, 6-80, 6-70, 6-60, 2-50, 6-40, 6-30, 6-24, 6-12, 8-100, 8-90, 8-80, 8-70, 8-60, 8-50, 8-40, 8-30, 8-24, 8-12, 10-100, 10-90, 10-80, 10-70, 10-60, 10-50, 10-40, 10-30, 10-24, or 10-12 of the artificial nucleic acid constructs herein. In some instances, at least about 10% to about 100% of the number of the artificial nucleic acid constructs are different in the plurality. In some instances, each artificial nucleic acid construct in the plurality is different.

In some aspects, the present disclosure provides a method for making the artificial nucleic acid construct disclosed herein, comprising adding to the artificial nucleic acid construct a nucleotide or nucleoside comprising a ribose modified at a 2' or 3' position, or a deoxyribose modified at a 2' or 3' position, or a combination thereof.

In some aspects, the present disclosure provides a method for making the artificial nucleic acid constructs disclosed herein, comprising modifying a ribose, deoxyribose, or a combination thereof at the 2' or 3' position in the artificial nucleic acid construct.

In some aspects, the present disclosure provides a method for making the plurality of artificial nucleic acid constructs, comprising mixing two or more of the artificial nucleic acid constructs disclosed herein.

In some aspects, the present disclosure provides an isolated cell comprising the artificial nucleic acid construct disclosed herein or a plurality thereof. In some instances, the cell is a eukaryotic cell.

In some aspects, the present disclosure provides a plant, seed, solution, microorganism, fertilizer, or soil comprising the artificial nucleic acid construct disclosed herein or a plurality thereof.

In some aspects, the present disclosure provides a composition comprising: (a) an artificial nucleic acid construct disclosed herein and (b) an enzyme or a catalytically or biologically active fragment thereof that performs an epigenetic modification of at least one base in a nucleic acid sequence of an organism.

In some aspects, the present disclosure provides a composition comprising: a vector comprising one or more artificial nucleic acid constructs herein or a plurality thereof.

In some aspects, the present disclosure provides a kit comprising: (a) an artificial nucleic acid construct, a plurality thereof, or a composition thereof as disclosed herein; and (b) a container comprising a soil, a fertilizer, a seed, a plant, a liquid, or any combination thereof.

In some aspects, the present disclosure provides a formulation comprising: (a) an artificial nucleic acid construct, a plurality thereof, or a composition thereof as disclosed herein; and (b) an excipient. In some instances, the excipient is an agriculturally acceptable excipient. In some instances, the formulation further comprises a fertilizer or a soil.

In some aspects, the present disclosure provides a method of making a formulation, comprising contacting an artificial nucleic acid construct, a plurality thereof, or a composition thereof as disclosed herein with an excipient to form the formulation.

In some aspects, the present disclosure provides an engineered plant or seed comprising a heritable modification that at least partially silences or activates at least one gene of the engineered plant or seed, wherein the heritable modification comprises a methylated base in a transcription regulatory region of the at least one gene, and wherein the heritable modification does not comprise a transgene, optionally comprising the artificial nucleic acid construct or a plurality thereof. In some instances, two genes are silenced. In some instances, the at least one methylated base is not naturally methylated in the nucleic acid sequence. In some instances, the transcription regulatory region comprises at least one selected from the group consisting of: a transcription start site, a TATA box, and an upstream activating sequence. In some instances, the methylated base comprises a plurality of methylated bases.

In some aspects, the present disclosure provides a plurality of engineered plants or seeds comprising variable gene expressions that at least partially silence or activate at least one gene of the engineered plants or seeds, optionally comprising the artificial nucleic acid construct or a plurality thereof disclosed herein. In some instances, the engineered plants or seeds comprise at least one modified base in at least one gene therein, which is not naturally methylated in the gene. In some instances, the base is modified with an alkyl, an aryl, a haloalkyl, an amino, a methyl, acetyl, a halo, or a combination thereof. In some instances, the engineered plants or seeds comprise at least one methylated base in at least one gene therein. In some instances, the plurality comprises at least about: 10-20, 20-50, 50-100, 100-1000, 100-900, 100-800, 100-700, 100-600, 100-500, 100-400, 100-300, 100-240, 100-120, or 1000-10000 of engineered plants or seeds.

In some aspects, the present disclosure provides a method, comprising applying a substance to an agricultural object, wherein the agricultural object comprises a seed, a plant, a constituent of a plant, or any combination thereof, and wherein the substance comprises the artificial nucleic acid construct or a plurality thereof disclosed herein. In some instances, the method at least partially silencing or activating a gene in the agricultural object. In some instances, the gene is at least partially silenced for at least one or two reproduction cycles. In some instances, the applying results in one or more of the following: (a) preventing or reducing or delaying an enzymatic browning of the agricultural object; (b) increasing a growth rate, a yield, or a lifespan of the agricultural object; (c) decreasing a growth rate, a yield, or a lifespan of the agricultural object; (d) increasing a pest resistance, a salt tolerance, a heat tolerance, a heavy metal tolerance, a disease tolerance, or a drought resistance of the agricultural object; (e) increasing or at least partially decreasing an amount or a production of a molecule made by the agricultural object; (f) altering a color of at least a portion of the agricultural object; (g) increasing or at least partially decreasing a flowering rate of the agricultural object; (h) increasing a volume or a weight of the agricultural object; (i) improving a flavor or a texture of an edible product of the agricultural object; (j) increasing a shelf life of the agriculture product; (k) decreasing the number and size of seeds of the agriculture product; and (j) increasing a nutritional content of the agricultural object; when the agricultural object is compared to a comparable agricultural object without application of the substance comprising the artificial nucleic acid construct. In some instances, the agricultural object is a plant embryo. In some instances, the agricultural object is selected from the group consisting of: soybean, corn, rice, tomato, alfalfa, wheat, potato, and green algae. In some instances, the contacting decreases the growth rate, the yield, or the lifespan of a weed. In some instances, the contacting increases the growth rate, the yield, or the lifespan of the agricultural object, and wherein the molecule is a psychoactive substance. In some instances, the psychoactive substance comprises a tetrahydrocannabinol. In some instances, the substance is a liquid, soil, microorganism, fertilizer, or herbicide.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative instances, in which the principles of the disclosure are utilized, and the accompanying drawings of which:

FIG. 6A illustrates that in a wild type plant, shoots grow in the opposite direction of the force of gravity (gravitropism). FIG. 6B illustrates that LZY1-CATS plants show a loss of gravitropism compared to wild type plants. FIG. 6C illustrates that in a wild type plant, shoots grow in the opposite direction of the force of gravity (gravitropism). FIG. 6D illustrates that LZY1-CATS plants show a loss of gravitropism compared to wild type plants.

FIG. 7A illustrates that a CATS-treated potato shows a slower enzymatic browning as compared to an untreated control potato. FIG. 7B depicts RT-PCT analysis of PPO mRNA levels in CATS-treated potato plants. CATS plants have reduced levels of the mRNA transcript, as compared to the control mRNA in untreated plants (FIG. 7C).

FIG. 11 depicts exemplary CATS oligonucleotides with modified backbones comprising phosphorothioate modifications, 2'O-Methyl modifications, 2'-Fluoro modifications, or any combination thereof.

DETAILED DESCRIPTION

Introduction

Figure 1:
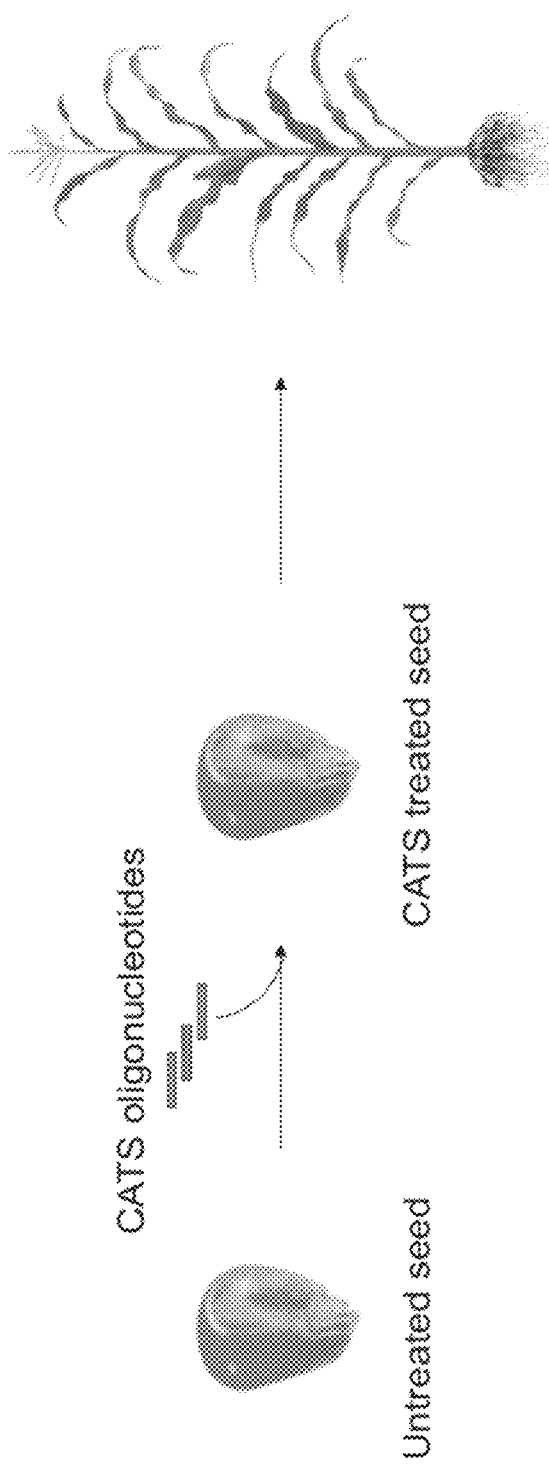
FIG. 1 depicts schematically treatment of an untreated seed with a plurality of CATS oligonucleotides.
Figure 2:
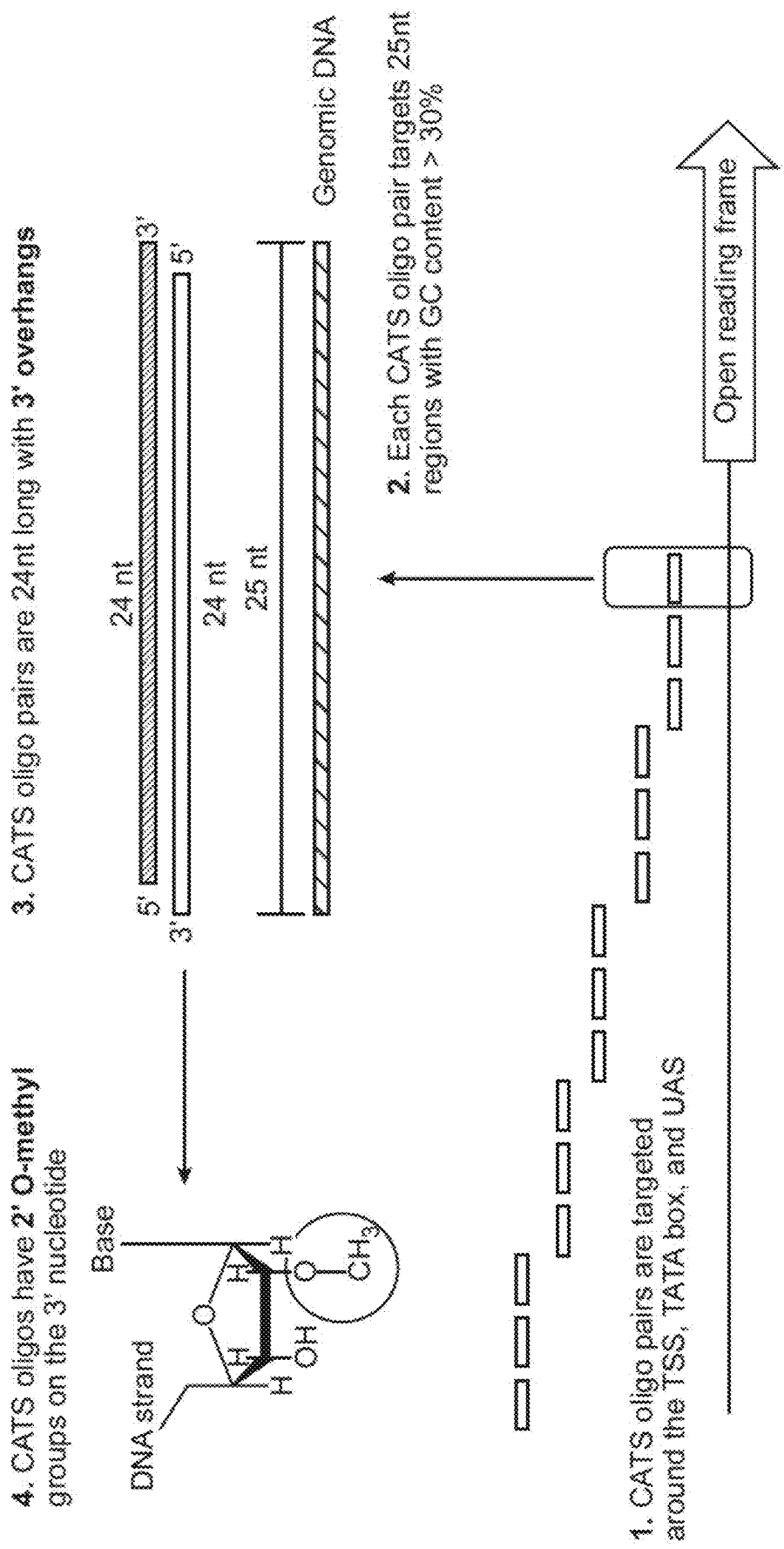
FIG. 2 depicts a non-limiting example of the design of a CATS oligonucleotide.

Disclosed herein are molecular techniques for at least partially silencing or activating specific target genes in plants to elicit desired phenotypes with commercial value. In some instances, this technology is referred to as Coat Applied Transcriptional Silencing (CATS) and uses specifically engineered DNA oligonucleotides constructs to induce nitrogenous base modification (e.g., cytosine methylation) and epigenetic silencing of target genes. The methods disclosed herein allow the specific and multiplex manipulation of plant gene expression, with design and build workflow of days, compared to the months or years necessary for transgenic approaches.

An engineered DNA oligonucleotide described herein can be prepared to mimic a nucleic acid sequence present in an RNA interference pathway. In some cases, an RNA interference pathway can be a pathway naturally present in an organism (e.g. a plant, a fungus, a bacterium, or an animal). For example, an engineered DNA oligonucleotide can be prepared to mimic a nucleic acid sequence present in a Drosophila melanogaster, Caenorhabditis elegans, or Arabidopsis thaliana RNA interference pathway. An exemplary RNA interference pathway can include an Arabidopsis thaliana RNA interference pathway. In the exemplary Arabidopsis thaliana RNA interference pathway, a first RNA nucleic acid is prepared through transcription using a polymerase IV enzyme. The first RNA nucleic acid transcribed from polymerase IV can be single stranded, or can be converted into a double stranded RNA nucleic acid. A resulting double stranded nucleic acid can be processed by a dicer enzyme (for instance, a Dicer-Like 3 (DCL3) enzyme) to produce smaller double stranded RNA nucleic acid fragments. Such RNA nucleic acid fragments can be methylated on a 2' or 3' hydroxyl group present on a ribose sugar present on the RNA nucleic acid fragments by a HUA Enhancer 1 (RENO enzyme or biological equivalent thereof. The methylated double-stranded RNA strand can be processed by an Argonaute 4 (AGO4) enzyme or biological equivalent thereof to produce a single stranded, methylated RNA nucleic acid. In some cases, the methylated RNA nucleic acid can modulate an expression of a gene (including a level of mRNA encoded by a gene or a polypeptide encoded by an mRNA) in an organism through multiple pathways. For instance, a methylated RNA nucleic acid can bind directly to an mRNA sequence encoding the polypeptide, thus acting as a silencing RNA nucleic acid. Further, a methylated RNA nucleic acid can recruit enzymes, such as AGO4, capable of inducing a cleavage of the mRNA when the methylated RNA nucleic acid associates with the mRNA sequence. Further, a methylated mRNA nucleic acid can associate with a DNA methylating enzyme, such as Domains Rearranged Methyltransferase 2 (DRM2), to catalyze a de novo methylation of genomic DNA encoding the mRNA sequence. In some cases, a methylated RNA nucleic acid can modulate an expression of a gene in an organism through any one, any 2, or all of 3 of these actions.

Accordingly, an engineered oligonucleotide can be engineered to mimic a nucleic acid present in an RNA interference pathway. For example, an engineered oligonucleotide can be engineered to mimic a methylated RNA nucleic acid, such as an RNA nucleic acid methylated using a HEN1 enzyme. Accordingly, such an engineered oligonucleotide can modulate an expression of a gene (including a level of mRNA encoded by a gene or a polypeptide encoded by an mRNA) in an organism through any combination of the actions referenced above. For example, an engineered oligonucleotide can bind directly to an mRNA sequence encoding the polypeptide, thus acting as a silencing nucleic acid. Further, an engineered oligonucleotide can recruit enzymes, such as AGO4, capable of inducing a cleavage of the mRNA when the engineered oligonucleotide associates with the mRNA sequence. Further, an engineered oligonucleotide can associate with a DNA methylating enzyme, such as Domains Rearranged Methyltransferase 2 (DRM2), to catalyze a de novo methylation of genomic DNA encoding the mRNA sequence. In some cases, an engineered oligonucleotide can modulate an expression of a gene in an organism through any one, any 2, or all of 3 of these actions.

Furthermore, an engineered oligonucleotide can be designed to be at least partially complementary to a desired target mRNA sequence. In some cases, a desired target mRNA sequence can be an mRNA that is a target of a natural methylated RNA nucleic acid in an RNA interference pathway. In some cases, a desired target mRNA can be an mRNA that is separate and distinct from any target of a natural methylated RNA nucleic acid in an RNA interference pathway. Accordingly, highly specific gene regulation can be accomplished by generating engineered oligonucleotides that are capable of associating with a target mRNA nucleic acid of interest.

In some instances, engineered nucleic acid constructs are designed with high sequence homology to a transcription regulatory region upstream of a target gene's open reading frame. In some instances, the nucleic acid constructs can be a double stranded DNA construct having at least one end overhang, such that the DNA construct mimics the double stranded RNA recognized by the plant's endogenous DNA methylation machinery, thereby directing endogenous DNA methylation to the transcription regulatory region. In some instances, methylation of cytosines in a gene's transcription regulatory region at least partially silence the gene.

Use of the nucleic acid constructs described herein has several advantages. The specifically designed oligonucleotides introduce cytosine methylation at a defined region of a plant genome, which can control transcript expression levels. The nucleic acid constructs can be introduced by application to the seed coat or to the growing roots of the plant, enabling rapid construction of plants with tailored gene expression profiles. In some instances, the modified bases (e.g., methylated cytosines) are heritable, enabling generation of parental breeding lines with desired expression profiles. Methylation and altered transcript levels can be propagated through future progeny generations. Additionally, the application of nucleic acid constructs to plants can be multiplexed by application of mixtures of nucleic acid constructs having unique targeting sequences, such that multiple transcription regulatory regions of a gene, and/or multiple gene, may be targeted simultaneously.

Yield drivers can be regulated by epigenetic mechanisms. Examples of yield drivers are hybrid vigor, photosynthesis and seed size. Stress resistance can be regulated by epigenetic mechanisms. Examples of stress resistance are disease resistance, drought tolerance, salt tolerance, heat tolerance and heavy metal stress. The applications of the CATs nucleotides can be broad and potentially encompass many gene regulatory networks that affect phenotype.

For example, constructs as described herein may provide one or more epigenetic modifications to one or more genes of an organism—such as an agricultural product. Introduction of such epigenetic modifications may modify one or more characteristics of the agricultural product. Such characteristics may include one or more of: photosynthesis, heterosis, nutrient efficiency, energy efficiency, seed size, plant biomass, circadian rhythm, flowering time, seed development, root development, disease resistance, drought tolerance, salt tolerance, heat tolerance, heavy metal stress, or any combination thereof. One or more characteristics may comprise flavor, color, texture, shelf-life, seedless varieties, or any combination thereof. An epigenetic modification to a gene may modify a characteristic. An epigenetic modification to a gene may modify a plurality of characteristics. A plurality of epigenetic modifications may modify a characteristic. A plurality of epigenetic modifications may modify a plurality of characteristics.

Additionally, constructs as described herein can be utilized to create diverse pools of organisms such as an agricultural product. Constructs can introduce one or more epigenetic modifications into one or more genes of an organism. Introduction of one or more epigenetic modifications can result in at least partial silencing or at least partial activation of one or more genes. Activation or silencing or a combination thereof of one or more genes in an organism can result in diversifying a species. Introducing epigenetic modifications into one or more genes of an organism can create a diverse pool of progeny. Such downstream applications can include breeding selection, such as selecting for advantageous characteristics.

Definitions

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the formulations or unit doses herein, some methods and materials are now described. Unless mentioned otherwise, the techniques employed or contemplated herein are standard methodologies. The materials, methods and examples are illustrative only and not limiting.

The details of one or more inventive instances or aspects are set forth in the accompanying drawings, the claims, and the description herein. Other features, objects, and advantages of the inventive instances or aspects disclosed and contemplated herein can be combined with any other instance or aspect unless explicitly excluded.

The open terms for example "contain," "containing," "include," "including," and the like mean comprising.

The singular forms "a", "an", and "the" are used herein to include plural references unless the context clearly dictates otherwise.

Unless otherwise indicated, some instances herein contemplate numerical ranges. When a numerical range is provided, unless otherwise indicated, the range can include the range endpoints. Unless otherwise indicated, numerical ranges can include all values and subranges therein as if explicitly written out.

The term "about" in relation to a reference numerical value can include a range of values plus or minus 10% from that value. For example, the amount "about 10" includes amounts from 9 to 11, including the reference numbers of 9, 10, and 11. The term "about" in relation to a reference numerical value can also include a range of values plus or minus 10%, 9%, 8%, 7%, 6%, 5%, 4%, 3%, 2%, or 1% from that value.

The term "facilitates" herein can refer to i) a machinery that when a construct is introduced to an organism with an appropriate molecular system for an epigenetic modification, it facilitates or enables the organism to use at least a part of the molecular system to epigenetically modify a nucleic acid sequence in the organism, or ii) a silencing of a target mRNA sequence that is at least partially complementary to the at least one strand of the artificial nucleic acid construct, iii) a cleavage of the target mRNA sequence, or iv) any combination of i), ii), or iii).

The term "compounds" can refer to compounds encompassed by generic formulae disclosed herein, any subgenus of those generic formulae, and any specific compounds within those generic or subgeneric formulae. The compounds can be a specific species, a subgenus or larger genus identified either by their chemical structure and/or chemical name. Further, compounds also include substitutions or modifications of any of such species, subgenuses or genuses, which are set forth herein. When the chemical structure and chemical name conflict, the chemical structure can be determinative of the identity of the compound. The compounds can contain one or more chiral centers and/or double bonds and therefore, can exist as stereoisomers, isomers, enantiomers or diastereomers. Accordingly, the chemical structures within the scope of the specification encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Further, when partial structures of the compounds are illustrated, asterisks indicate the point of attachment of the partial structure to the rest of the molecule. Enantiomeric and stereoisomeric mixtures can be resolved into their component enantiomers or stereoisomers using separation techniques or chiral synthesis techniques well known to the skilled artisan. The compounds can include any salt or solvate forms of the compounds. The compounds can include any derivatives of the compounds.

The term "derivative," which can be used interchangeably with the term "analog." Compound A can be a derivative or analog of compound B if 1, 2, 3, 4, or 5 atoms of compound A is replaced by another atom or a functional group (e.g., amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, or substituted or unsubstituted heterocycloalkyl) to form compound B. The term "derivative" may also refer to a chemical compound that is structurally similar to another but differs slightly in composition (as in the replacement of one atom by an atom of a different element or in the presence of a particular functional group)

The term "solvate" can include, but is not limited to, a solvate that retains one or more of the activities and/or properties of the compound and that is not undesirable. Examples of solvates include, but are not limited to, a compound in combination with water, isopropanol, ethanol, methanol, DMSO, ethyl acetate, acetic acid, ethanolamine, or combinations thereof.

The term "salt" can include, but are not limited to, salts that retain one or more of the activities and properties of the free acids and bases and that are not undesirable. Illustrative examples of salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

Unless otherwise indicated, a chemical structure can refer to any compound having the chemical structure.

Unless otherwise indicated, formulations herein can be powdery, pellets, or beads or be a liquid.

Unless otherwise indicated, formulations herein can contain water in an amount from about 0% to about 15% w/w, for example about: 0-10%, 0-5%, or 0-1% w/w; or less than about: 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90% or 99% w/w, based on the weight of the formulation.

Unless otherwise indicated, whenever there is a stereocenter in a structure disclosed or illustrated herein, the stereocenter can be R or S in each case.

Unless otherwise indicated, whenever there is a symbol

when used as part of a molecular structure herein can refer to a single bond.

The term "amino" can refer to functional groups that contain a basic nitrogen atom with a lone pair. For example, amino can include the radical

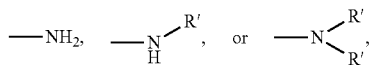

wherein each R' is independently H, halo, alkyl, aryl, heteroalkyl, arylalkyl, heteroaryl, heteroarylalkyl, cycloalkyl, or heterocycloalkyl.

The term "halo" or "halogen" can refer to fluorine, chlorine, bromine or iodine or a radical thereof.

The term "alkyl" can refer to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl; and the like.

The term "aryl" can refer to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain instances, an aryl group comprises from 6 to 20 carbon atoms.

The terms "heteroalkyl, heteroalkanyl, heteroalkenyl, heteroalkynyl" refer to alkyl, alkanyl, alkenyl and alkynyl groups, respectively, in which one or more of the carbon atoms (and any associated hydrogen atoms) are each independently replaced with the same or different heteroatomic groups. Typical heteroatomic groups include, but are not limited to, —O—, —S—, —O—O', —S—S—, —O—S, NR', —N═N—, ═N—N═, —N═N—NR'—, —PH—, —P(O)$_2$—, —O—P(O)$_2$—, —S(O)—, —S(O)$_2$—, —SnH$_2$—and the like, wherein R' is hydrogen, alkyl, substituted alkyl, cycloalkyl, substituted cycloalkyl, aryl or substituted aryl.

The term "heteroaryl" can refer to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain instances, the heteroaryl group is from 5-20 membered heteroaryl, and in other instances is from 5-10 membered heteroaryl. In certain instances heteroaryl groups are those derived from thiophene, pyrrole, benzothiophene, benzofuran, indole, pyridine, quinoline, imidazole, oxazole and pyrazine.

The term "arylalkyl" can refer to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain instances, an arylalkyl group is (C$_6$-C$_{30}$) arylalkyl, e.g., the alkanyl, alkenyl or alkynyl moiety of the arylalkyl group is (C$_1$-C$_{10}$) and the aryl moiety is (C$_6$-C$_{20}$).

The term "heteroarylalkyl" can refer to an acyclic alkyl group in which one of the hydrogen atoms bonded to a carbon atom, typically a terminal or spa carbon atom, is replaced with a heteroaryl group. Where specific alkyl moieties are intended, the nomenclature heteroarylalkanyl, heteroarylalkenyl and/or heteroarylalkynyl is used. In certain instances, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl.

The term "cycloalkyl" can refer to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In a certain instance, the cycloalkyl group is ($C_3$-$C_{10}$) cycloalkyl, or in certain instances ($C_3$-$C_6$) cycloalkyl.

The term "heterocycloalkyl" can refer to a saturated or unsaturated cyclic alkyl group in which one or more carbon atoms (and any associated hydrogen atoms) are independently replaced with the same or different heteroatom. Typical heteroatoms to replace the carbon atom(s) include, but are not limited to, N, P, O, S, and Si. Typical heterocycloalkyl groups include, but are not limited to, groups derived from epoxides, imidazolidine, morpholine, piperazine, piperidine, pyrazolidine, pyrrolidine, quinuclidine, and the like.

The term "diastereomeric excess" (DE) can refer to the difference from the relative abundance of two diastereomers. For instance, if there are two diastereomers and their mole or weight percentages are A and B, then DE can be calculated as: DE=[(A−B)/(A+B)]*100%. For example, if a mixture contains 75% of one diastereomer and 25% of the other diastereomer, the diastereomeric excess is 50%. In another example, if a mixture that is 95% of one diastereomer, the diastereomeric excess is 90%.

The term "enantiomeric excess" (EE) can refer to the difference from the relative abundance of two enantiomers. For instance, if there are two enantiomers and their mole or weight percentages are A and B, then EE can be calculated as: EE=[(A−B)/(A+B)]*100%. For example, if a mixture contains 75% of one enantiomer and 25% of the other enantiomer, the enantiomeric excess is 50%. In another example, if a mixture that is 95% of one enantiomer, the enantiomeric excess is 90%.

The term "substituted" can refer to a group in which one or more hydrogen atoms are each independently replaced with the same or different substituent(s). Typical substituents include, but are not limited to halo, alkyl, aryl, heteroalkyl, arylalkyl, heteroaryl, heteroarylalkyl, cycloalkyl, and heterocycloalkyl.

Unless otherwise indicated, "treated" can refer to "contacted." Similarly, "untreated" can refer to "uncontacted."

The term "substantially comparable plant" can refer to a plant of the same species as an earlier referenced plant. For example, a substantially comparable but otherwise uncontacted plant belongs to the same species as a contacted plant. The substantially comparable but otherwise uncontacted plant can have a height of about 80% to 120% of the contacted plant (as measured from the surrounding soil to the highest point of the plant) and/or can have a mass of about 80% to 120% of the contacted plant.

The term "drought" can mean conditions with less than 20 inches, 15 inches, 10 inches, or 5 inches of rainfall within the past 12 months. The term "drought" can also mean conditions with a Palmer Drought Severity Index (PDSI) of less than −1.0. The term "adequately irrigated condition" can mean a condition with more than 20 inches of rainfall within the past 12 months. The term "adequately irrigated condition" can mean a condition with a PDSI of more than −1.0.

The term "plant" can be used interchangeably with the term "crop" and can include, but is not limited to any crop, cultivated plant, fungus, or alga that may be harvested for food, clothing, livestock fodder, biofuel, medicine, or other uses. For example, plants include field and greenhouse crops, including but not limited to broad acre crops, fruits and vegetables, perennial tree crops, and ornamentals. Plants include, but are not limited to sugarcane, pumpkin, maize (corn), wheat, rice, cassava, soybeans, hay, potatoes, cotton, tomato, alfalfa, and green algae. Plants also include, but are not limited to any vegetable, such as cabbage, turnip, carrot, parsnip, beetroot, lettuce, beans, broad beans, peas, potato, eggplant, tomato, cucumber, pumpkin, squash, onion, garlic, leek, pepper, spinach, yam, sweet potato, and cassava. In some instances, the plant can also include a fruit, a leaf, a stalk, a root, a flower, a plant embryo, or any combination thereof.

Nucleic Acid Constructs

Disclosed herein are nucleic acid constructs for at least partially silencing or activating a gene in an organism, wherein the nucleic acid construct is configured to guide endogenous modification (e.g., methylation) of at least one base of the gene in the organism. In some instances, the nucleic acid construct can be single-stranded or double-stranded.

In some instances, the nucleic acid construct can be an artificial double-stranded nucleic acid construct comprising 1) a modified ribose or a modified deoxyribose or a combination thereof and 2) a terminal end overhang, wherein, when the nucleic acid construct associates with a nucleic acid sequence of an organism, an enzyme performs an epigenetic modification of at least one base in the nucleic acid sequence of the organism. In some instances, the modified ribose or the modified deoxyribose is comprised in a terminal nucleotide of the nucleic acid construct. In some instances, the nucleic acid construct associates with an argonaut protein that associates with the nucleic acid sequence.

In some instances, the nucleic acid construct can comprise deoxyribonucleic acid (DNA), ribonucleic acid (RNA), or a combination thereof. In some instances, the nucleic acid construct can comprise at least one deoxyribonucleic acid. In some instances, the nucleic acid construct can comprise at least about: 2, 3, 4, 5, 6, 7, 8, 9, 10, 15, 20, 25, 30, 35, 40, 45, 50, 55, 60, 65, 70, 75, 80, 85, or 100 deoxyribonucleic acids. In some instances, the nucleic acid construct can comprise at least one ribonucleic acid. In some instances, the nucleic acid construct can comprise at least about: 2, 3, 4, 5, 6, 7, 8, 9, 10, 15, 20, 25, 30, 35, 40, 45, 50, 55, 60, 65, 70, 75, 80, 85, or 100 ribonucleic acids.

In some instances, the base of the gene may be a cytosine. In some instances, the base of the gene may be an adenine, a guanine, or a thymine.

In some instances, the nucleic acid construct may be a double stranded DNA construct. In some instances, the double stranded DNA construct may comprise two polynucleotide strands of the same length. In some instances, the double stranded DNA construct may comprise two polynucleotide strands of a different length. In some instances, the double stranded DNA construct may comprise at least one end overhang. In some instances, an end overhang may comprise a single nucleotide. In some instances, an end overhang may comprise at least about: 2, 3, 4, 5, 6, 7, 8, 9, or 10 nucleotides. In some instances, the double stranded DNA construct may comprise an end overhang at each end of the DNA construct. In some instances, the double stranded DNA construct may comprise an end overhang at each end of the DNA construct, wherein the end overhangs are of the same length. In some instances, the double stranded DNA construct may comprise a one-nucleotide end overhang at each end of the DNA construct. In some instances, the double stranded DNA construct may comprise a 3'-end overhang. In some instances, the double stranded DNA construct may comprise a 5'-end overhang. In some instances, the double stranded DNA construct may comprise a one-nucleotide 3'-end overhang at each end of the DNA construct.

In some instances, the nucleic acid construct may comprise at least one modified sugar, for example modified at the 2' position and/or the 3' position. Numbering of a nucleotide sugar should be understood to follow normal conventions of positional numbering in the art. Specifically, carbon numbering in nucleotide sugar is as illustrated by ribose sugar shown below:

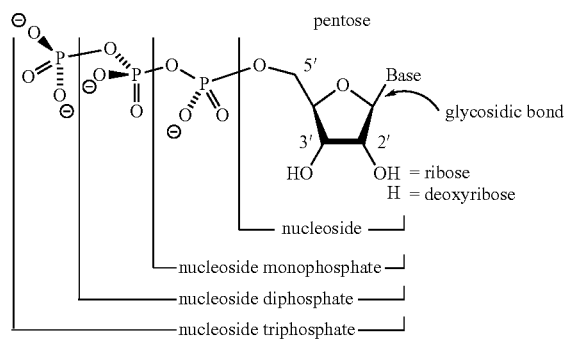

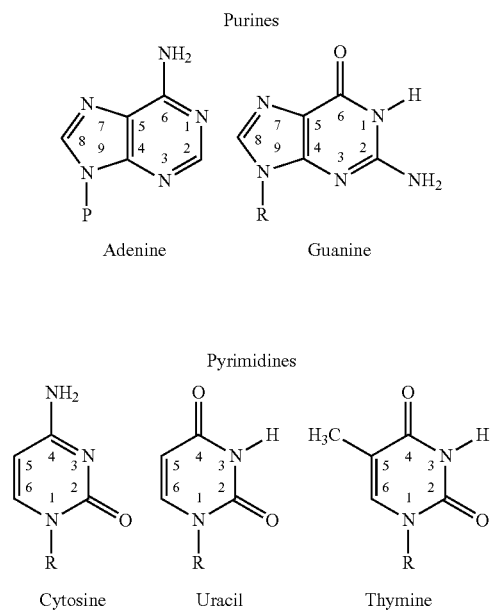

In some instances, the modified sugar may comprise a 2'-R, 2'-O—R, 3'-R, or 3'-O—R group. In some instances, the R group may be selected from the group consisting of alkyl, aryl, haloalkyl, amino, and halogen. In some instances, the R group can be a fluro-(F). In some instances, the R group can be methoxyethyl. In some instances, the R group can be methyl. In some instances, R can be —(C═O)n-R1, or the ribose modification comprises the structure represented by:

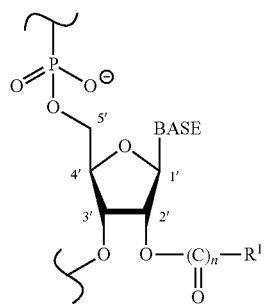

In some instances, R1 can be alkyl, alkenyl, alkynyl aryl, substituted alkyl, substituted alkenyl, substituted alkynyl, or a substituted aryl.

In some instances, the modified sugar may be comprised in a terminal nucleotide of at least one strand of the nucleic acid construct. In some instances, the modified sugar may be comprised in a 3'-terminal nucleotide of at least one strand of the nucleic acid construct. In some instances, the nucleic acid construct may be a double stranded DNA construct, wherein each strand of the DNA construct comprises at least one modified sugar. In some instances, the nucleic acid construct may be a double stranded DNA construct, wherein each strand of the DNA construct comprises at least one modified sugar in the strand's 3'-terminal nucleotide.

In some cases, the sugar can be a derivative of ribose. In some instances, the sugar can be arabinose. In some instances, the sugar may be 2'-deoxy-2'-fluoro-arabino (FANA). In some instances, the sugar may be a derivative of hexose (e.g. HNA; hexose nucleic acid). In some instances, the sugar may be a derivative of threose (e.g. TNA; threose nucleic acid). In some instances, the sugar may be replaced with a morpholino group and the backbone composed of phosphoramidate linkages (e.g. PMO; Phosphorodiamidate Morpholino Oligomer) In some instances, the sugar may be a bridged sugar (e.g. BNA; bridged nucleic acid). In some instances, the bridging carbon between the 2' and 4' positions may be a methylene group (e.g. LNA; locked nucleic acid). In some instances, the bridging carbon between the 2' and 4' positions may be an ethyl group. In some instances, the 2',4'-constrained ethyl sugar derivative may be in the S stereochemical configuration (e.g. (S)-cET). In some instances, the sugar can be acyclic. In some instances, sugar may be a derivative or ribose lacking the 2' and 3'-bond (e.g. UNA; unlocked nucleic acid). In some instances, the sugar may be a derivative of threoninol (e.g aTNA; threoninol nucleic acid). In some instances, the sugar may be a derivative of serinol (e.g. SNA; serinol nucleic acid). In some instances, the sugar may be a derivative of glycol (e.g. GNA; glycol nucleic acid).

In some cases, the sugars within each strand are linked 3' to 5' by a bridging phosphodiester linkage. In some instances one oxygen within the phosphodiester linkage may be replaced with a sulfur forming a phosphorthioate. In some instances, two oxygens within phosphodiester linkage are replaced with sulfur forming a phosphorodithioate linkage. In some instances, the 3'-5' phosphodiester contains an additional ester group on a non-bridging oxygen. In some instances the sugar bridging phosphate may be a phosphotriester. In some instances, the phosphotriester may be stable. In some instances, the phosphotriester may be bior-eversible.

In some cases, a nucleic acid disclosed herein is associated with or encapsulated within a liposome. In some instances, the liposome may be comprised of a cationic peptide (e.g. DOTAP). In some instances, the liposome may be comprised of an ionizable lipid (e.g. DLinDMA or KC2-DMA).

In some cases, a nucleic acid disclosed herein may be associated with or encapsulated within a nano or microparticle. In some instances, nano or microparticle may be comprised of poly lactic-co-glycolic acid (PLGA). In some instances, the nucleic acid may be attached to a nanoparticle. In some instances the nanoparticle may be a liposome. In some instances the nanoparticle may be a micelle. In some instances the nanoparticle comprises silica. In some instances the nanoparticle comprises a mineral or mineral derivative. In some instances, the nucleic acid may be conjugated to a nanoparticle comprised gold. In some instances the nanoparticle may be a quantum dot. In some instances, the nucleic acid may be conjugated to a nanoparticle comprised of DNA or other nucleic acids. In some instances, the nucleic acid may be attached to a microparticle. In some instances the microparticle may comprise silica. In some instances the microparticle may comprise clay.

In some cases, one or more nucleic acid sequences may be directly conjugated to a ligand or other moiety to enhance uptake, transport, cytoplasmic or nuclear delivery. In some instances, the ligand may be attached to a 5' end of the nucleic acid duplex. In some instances, the ligand may be attached to a 3' end of the nucleic acid duplex. In some instances, the ligand may be attached to both the 5' end and the 3' end of the nucleic acid duplex. In some instances, the ligand may be attached to a position within the nucleic acid duplex. In some instances, the ligand may be attached to the non-Watson-Crick face of one of the nucleobases. In some instances, the ligand may be attached to the 5-position of uracil. In some instances, the ligand is attached to multiple positions on the nucleic acid. In some instances, more than one ligand may be attached. In some instances, the multiple copies of the same ligand are attached. In some instances, multiple different ligands are attached.

In some instances, the ligand may be a sugar or polysaccharide. In some instances, the ligand may be GalNAc. In some instances, the ligand may be two GalNAc moieties attached to a single position on the nucleic acid. In some instances, the ligand may be three GalNAc moieties attached to a single position on the nucleic acid. In some instances, the ligand may be more than three GalNAc moieties attached to a single position on the nucleic acid. In some instances, the ligand may be chitin or a derivative thereof. In some instances, the ligand may be mannose or a derivative thereof. In some instances, the ligand may be sialic acid or a derivative thereof.

In some instances, a nucleic acid disclosed herein may be conjugated to a peptide or derivative thereof. In some instances, the peptide may enhance nucleic acid uptake. In some instances, the peptide may enhance endosomal escape. In some instances, the peptide may enhance both uptake and endosomal escape. In some instances, the peptide may enhance delivery to vascular tissue and long-distance transport. In some instances, the peptide may be a cationic. In some instances, the peptide may be a derivative of a viral protein. In some instances, the ligand may be an arginine rich peptide (e.g. TAT). In some instances, the peptide may be histidine rich peptide (e.g. endoporter). In some instances, the peptide may be a lytic peptide (e.g. melittin). In some instances, the peptide may be a masked peptide that may be activated upon exposure to acidic conditions. In some instances, the peptide may be pH sensitive. In some instances, the peptide may be a derivative of a bacterial protein. In some instances, the peptide may be a derivative of flagellin. In some instances, the peptide may be a derivative of EF-Tu.

In some cases, a nucleic acid disclosed herein may be conjugated to a sterol or sterol derivative. In some instances, the nucleic acid may be conjugated to cholesterol or a cholesterol derivative. In some instances the nucleic acid may be conjugated to a lipid. In some instances the nucleic acid may be conjugated to a single chain lipid. In some instances the nucleic acid may be conjugated to a single chain lipid that contains from 1 to 22 carbons. In some instances the nucleic acid may be conjugated to a single chain lipid that is saturated. In some instances the nucleic acid may be comprised of at least one unsaturated position. In some instances the nucleic acid may be conjugated to a diacyl lipid. In some instances the nucleic acid may be conjugated to diacyl lipid that contains from 1 to 22 carbons. In some instances the nucleic acid may be conjugated to a diacyl lipid that is saturated. In some instances the nucleic acid comprises at least one unsaturated position. In some instances, the nucleic acid may be conjugated to a vitamin or vitamin derivative. In some instances, the nucleic acid may be conjugated to tocopherol.

In some instances, the nucleic acid construct comprises at least about: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 base pairs. In some instances, the nucleic acid construct comprises at least about: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 base pairs. In some instances, the nucleic acid construct comprises from 2 to about 100 base pairs. In some instances, the nucleic acid construct comprises from about 10 to about 100 base pairs. In some instances, the nucleic acid construct comprises from about 10 to about 50 base pairs. In some instances, the nucleic acid construct comprises from about 10 to about 40 base pairs. In some instances, the nucleic acid construct comprises from about 10 to about 30 base pairs. In some instances, the nucleic acid construct comprises from about 20 to about 30 base pairs. In some instances, the nucleic acid construct comprises from about (4, 6, 8, or 10) to about 24 base pairs, e.g., about 10 to about 24 base pairs. In some instances, the nucleic acid construct comprises 23 base pairs. In some instances, the nucleic acid construct comprises 24 base pairs.

In some instances, the nucleic acid construct comprises at least about 60%, 65%, 70%, 75%, 80%, 85%, 90%, 91%, 92%, 93%, 94%, 95%, 96%, 97%, 98%, 99%, 99.5%, 99.9%, or 100% sequence identity to a transcription regulatory region of the gene.

In some instances, the transcription regulatory region comprises at least about 10%, 15%, 20%, 25%, 30%, 35%, 40%, 45%, 50%, 55%, 60%, 65%, 70%, 75%, 80%, 85%, or 90% guanine-cytosine content (G-C content). In some instances, the nucleic acid construct comprises at least one nucleotide strand having at least about 10%, 15%, 20%, 25%, 30%, 35%, 40%, 45%, 50%, 55%, 60%, 65%, 70%, 75%, 80%, 85%, or 90% G-C content.

In some instances, the nucleic acid construct comprises at least one polynucleotide strand that may not be phosphorylated at a terminal nucleotide of the polynucleotide strand. In some instances, the nucleic acid construct comprises at least one polynucleotide strand that may not be phosphorylated at a 5'-terminal nucleotide of the polynucleotide strand. In some instances, the nucleic acid construct comprises at least one polynucleotide strand that may not be phosphorylated at a 3'-terminal nucleotide of the polynucleotide strand. In some instances, the nucleic acid construct may be a double stranded nucleic acid construct that comprises two polynucleotide strands, wherein each of the polynucleotide strands may not be phosphorylated at a 5'-terminal nucleotide of the polynucleotide strand. In some instances, the nucleic acid construct may be a double stranded DNA construct that comprises two polynucleotide strands, wherein each of the polynucleotide strands may not be phosphorylated at a 3'-terminal nucleotide of the polynucleotide strand.

In some instances, the gene is at least partially silenced for at least one reproduction cycle. At least partial gene silencing should be understood to mean that the gene is transcribed at a level that is decreased relative to the unmodified gene. In some instances, the unmodified gene is a wild type gene. Measurement of gene transcription may be done by any of methods commonly known in the art, such as measure of mRNA transcript levels. In some instances, the gene is at least partially silenced for at least about: 2, 3, 4, 5, 6, 7, 8, 9, 10, 15, 20, or 30 reproduction cycles. In some instances, the gene may be at least about: 5%, 10%, 15%, 20%, 25%, 30%, 35%, 40%, 45%, 50%, 55%, 60%, 65%, 70%, 75%, 80%, 85%, 90%, 95%, 99%, or 100% silenced, as determined by measurement of a corresponding mRNA transcript level of the gene.

In some instances, disclosed herein is a nucleic acid construct configured to recruit an endogenous epigenetic modifying enzyme or fragment thereof to a portion of said nucleic acid sequence that is targeted for epigenetic modification. "Endogenous" should be understood to mean naturally occurring within the organism that contains the gene. Thus, an "endogenous" epigenetic modifying enzyme should be understood to mean a modifying enzyme that is naturally present in the organism that contains the gene.

In some instances, the nucleic acid construct may comprise a nucleic acid sequence having 50%, 55%, 60%, 65%, 70%, 75%, 80%, 85%, 90%, 95%, 96%, 97%, 98%, 99%, 99.5%, 99.9%, or 100% sequence identity to a nucleic acid sequence of any one SEQ ID NOs: 1-664. In some instances, the nucleic acid construct may comprise a nucleic acid sequence having a nucleic acid sequence of any one SEQ ID NOs: 1-664.

In some cases, an enzyme or fragment thereof may catalyze a transfer of a methyl group to at least one base of a nucleic acid sequence, such as a portion of a gene or a transcription regulatory region of a gene. In some cases, an enzyme or fragment thereof may comprise a methyltransferase. In some cases, an enzyme or fragment thereof may comprise a methyltransferase (MET), a chromomethyltransferase (CMT), a domain rearranged methyltransferase (DRM), any catalytically active fragment thereof, or any combination thereof. In some cases, enzyme may comprise Dnmt3a, Dnmt3b, Dnmt3L, DRM1, DRM2, NtDRM1, Zmet3, Fmu, Dnmt1, MET1, DIM2, DRM2, CMT1, CMT3, any catalytically active fragment thereof, or any combination thereof. A CMT enzyme may comprise OsCMT3, ZCMT3, OsCMT1, NtCMT1, CMT3, any catalytically active fragment thereof or any combination thereof. A MET enzyme may comprise NtMET1, OsMET1-2, ZMET1, OsMET1-1, MET1, any catalytically active fragment thereof, or any combination thereof. A DRM enzyme may comprise OsDRM3, OsDRM2, OsDRM1a, OsDRM1b, ZMET3, NtDRM1, DRM1, DRM2, any catalytically active fragment thereof, or any combination thereof. A DNMT2 enzyme may comprise OsDNMT2, ZMET4, OsCMT2, any catalytically active fragment thereof, or any combination thereof. A nucleic acid sequence may be contacted with any of the forgoing enzymes or fragments thereof thereby yielding an epigenetic modification of at least one base in a nucleic acid sequence (such as a gene of interest). Compositions as described herein, including nucleic acid constructs, may guide endogenous enzymes or fragments thereof to a base of interest in a nucleic acid sequence and thereby direct the contact of the enzyme or fragment thereof with the base of interest such that the enzyme or fragment thereof performs epigenetic modification of the base of interest.

Methods as described herein may comprise methylating one or more bases of a nucleic acid sequence (such as a portion of a gene or a transcription regulatory region of a gene). Methods as described herein may comprise oxidizing one or more bases of a nucleic acid sequence, such as a portion of a gene or a transcription regulatory region of a gene. Methods as described herein may comprise epigenetically modifying at least one base of a nucleic acid sequence, said epigenetically modification being heritable to a plant progeny.

In some cases, an enzyme or fragment thereof may catalyze a change in an epigenetic modification of at least one base of a nucleic acid sequence (such as a portion of a gene or a transcription regulatory region of a gene). A change in an epigenetic modification may include a conversion of a methylated base to a hydroxymethylated base, a carboxylated base, a formylated base, or a combination of any of these. In some cases, an enzyme may comprise a dioxygenase. In some cases, an enzyme may comprise a ten-eleven translocation (TET) family enzyme. In some cases, an enzyme may comprise TET1, TET2, TET3, CXXC finger protein 4 (CXXC4), any catalytically active fragment thereof, or any combination thereof.

An epigenetic modification may occur at any base, such as a cytosine, a thymine, a uracil, an adenine, a guanine, or any combination thereof. The epigenetic modification may be a heritable epigenetic modification, such as an epigenetic modification passed to at least one progeny of an organism. The epigenetic modification may be an engineered epigenetic modification, such as an epigenetic modification that is not non-naturally occurring at a particular base in a nucleic acid sequence of a native organism but one that is introduced into the organism or into an ancestor of an organism using a method as described herein. An organism may comprise a heritable epigenetic modification that may have been previously introduced into a parent organism or an ancestor organism that is retained for at least one reproduction cycle.

In some cases, an epigenetic modification may comprise an oxidation or a reduction. A nucleic acid sequence may comprise one or more epigenetically modified bases. An epigenetically modified base may comprise any base, such as a cytosine, a uracil, a thymine, adenine, or a guanine. An epigenetically modified base may comprise a methylated base, a hydroxymethylated base, a formylated base, or a carboxylic acid containing base or a salt thereof. An epigenetically modified base may comprise a 5-methylated base, such as a 5-methylated cytosine (5-mC). An epigenetically modified base may comprise a 5-hydroxymethylated base, such as a 5-hydroxymethylated cytosine (5-hmC). An epigenetically modified base may comprise a 5-formylated base, such as a 5-formylated cytosine (5-fC). An epigenetically modified base may comprise a 5-carboxylated base or a salt thereof, such as a 5-carboxylated cytosine (5-caC).

A construct may comprise one or more modifications, such as a chemical modification. A construct may comprise about: 1, 2, 3, 4, 5, 6, 7, 8, 9, 10, 11, 12, 13, 14, 15, 16, 17, 18, 19, 20, 25, 30, 35 modifications or more. A construct may comprise from about 1 to about 10 modifications. A construct may comprise from about 1 to about 20 modifications. A construct may comprise from about 5 to about 20 modifications. A modification may be added to a construct to enhance stability of the construct, such as when delivered in vivo. A modification may be added to a construct to enhance update of the construct, such as when delivered in vivo. A portion of bases of a construct may comprise a modification, such as about 10%, 20%, 30%, 40%, 50%, 60%, 70%, 80%, 90% of bases or more. A modification may comprise addition of a methyl group, a fluoro group, a phosphorthioate backbone, or any combination thereof.

A construct may be double stranded. A double stranded constructs may comprise a length of from about 10 basepairs (bp) to about 100 bp. Constructs may comprise a length of from about 10 bp to about 20 bps. Constructs may comprise a length of from about 10 bp to about 30 bps. Constructs may comprise a length of from about 10 bp to about 40 bps. Constructs may comprise a length of from about 10 bp to about 50 bps. Constructs may comprise a length of from about 10 bp to about 60 bps. Constructs may comprise a length of from about 10 bp to about 70 bps. Constructs may comprise a length of from about 10 bp to about 80 bps. Constructs may comprise a length of from about 10 bp to about 90 bps. Constructs may comprise a length of from about 15 bp to about 40 bp. Constructs may comprise a length of from about 15 bp to about 35 bp. Constructs may comprise a length of from about 15 bp to about 60 bp. Constructs may comprise a length of from about 5 bp to about 30 bp. Constructs may comprise a length of from about 5 bp to about 25 bps.

Detection of Epigenetic Modification

In some aspects, an epigenetic modification disclosed herein such as DNA methylation can be detected. In some instances, the modification, e.g., methylated nucleotide, may be detected by bisulfite sequencing. Bisulfite treatment may convert a cytosine base to uracil and leave methylated cytosines unconverted. Bisulfite treatment may be applied to a portion of a sample and leave a second portion of the sample untreated. Bisulfite treatment may be performed on a sample prior to sequencing or after sequencing. Bisulfite treatment may be utilized alone or in combination with additional techniques to determine a presence, a pattern or a level of epigenetic modification in a nucleic acid sequence, such as a presence, a pattern or a level of methylation in a sequence. Bisulfite sequencing may determine a presence, a pattern, or a level of an epigenetic modification in a nucleic acid sequence. Bisulfite-free sequencing may determine a presence, a pattern, or a level of an epigenetic modification in a nucleic acid sequence. A bisulfite treated sequence may be compared to a comparable sequence having not been treated with bisulfite to determine a presence, a pattern, or a level of epigenetic modification in a nucleic acid sequence.

Sequencing (such as bisulfite-free sequencing) may be utilized alone or in combination with additional techniques to determine a presence, a pattern or a level of epigenetic modification in a nucleic acid sequence, such as a presence, a pattern or a level of methylation in a sequence. Sequencing (such as bisulfite-free sequencing) may determine a presence, a pattern, or a level of an epigenetic modification in a nucleic acid sequence. Sequencing may determine a presence, a pattern, or a level of an epigenetic modification in a nucleic acid sequence. A treated sequence (such as a sequence having a label added to an epigenetic modification) may be compared to a comparable sequence having not been treated to determine a presence, a pattern, or a level of epigenetic modification in a nucleic acid sequence.

The term "sequencing" as used herein, may comprise bisulfite-free sequencing, bisulfite sequencing, TET-assisted bisulfite (TAB) sequencing, ACE-sequencing, high-throughput sequencing, Maxam-Gilbert sequencing, massively parallel signature sequencing, Polony sequencing, 454 pyrosequencing, Sanger sequencing, Illumina sequencing, SOLiD sequencing, Ion Torrent semiconductor sequencing, DNA nanoball sequencing, Heliscope single molecule sequencing, single molecule real time (SMRT) sequencing, nanopore DNA sequencing, shot gun sequencing, RNA sequencing, Enigma sequencing, or any combination thereof.

In some cases, a method may comprise sequencing. The sequencing may include bisulfite sequencing or bisulfite-free sequencing.

In some instances, the methods may include storing the sample for a time such as seconds, minutes, hours, days, weeks, months, years or longer after the sample is obtained and before the sample is analyzed. In some cases, the sample obtained from a subject is subdivided prior to the step of storage or further analysis such that different portions of the sample are subject to different downstream methods or processes including but not limited to any combination of methods described herein, storage, bisulfite treatment, amplification, sequencing, labeling, cytological analysis, adequacy tests, nucleic acid extraction, molecular profiling or a combination thereof.

In some cases, a portion of the sample may be stored while another portion of said sample is further manipulated. Such manipulations may include but are not limited to any method as described herein; bisulfite treatment; sequencing; amplification; labeling; molecular profiling; cytological staining; nucleic acid (RNA or DNA) extraction, detection, or quantification; gene expression product (RNA or Protein) extraction, detection, or quantification; fixation; and examination.

In some instances, a methylated nucleotide may be detected by nanopore sequencing. Nanopores may be used to sequence, a sample, a small portion (such as one full gene or a portion of one gene), a substantial portion (such as multiple genes or multiple chromosomes), or the entire genomic sequence of an individual. Nanopore sequencing technology may be commercially available or under development from Sequenom (San Diego, Calif.), Illumina (San Diego, Calif.), Oxford Nanopore Technologies LTD (Kidlington, United Kingdom), and Agilent Laboratories (Santa Clara, Calif.). Nanopore sequencing methods and apparatus are have been described in the art and for example are provided in U.S. Pat. No. 5,795,782, herein incorporated by reference in its entirety.

Nanopore sequencing can use electrophoresis to transport a sample through a pore. A nanopore system may contain an electrolytic solution such that when a constant electric field is applied, an electric current can be observed in the system. The magnitude of the electric current density across a nanopore surface may depend on the nanopore's dimensions and the composition of the sample that is occupying the nanopore. During nanopore sequencing, when a sample approaches and or goes through the nanopore, the samples cause characteristic changes in electric current density across nanopore surfaces, these characteristic changes in the electric current enables identification of the sample. Nanopores used herein may be solid-state nanopores, protein nanopores, or hybrid nanopores comprising protein nanopores or organic nanotubes such as carbon or graphene nanotubes, configured in a solid-state membrane, or like framework. In some instances, nanopore sequencing can be biological, a solid state nanopore or a hybrid biological/solid state nanopore.

In some instances, a biological nanopore can comprise transmembrane proteins that may be embedded in lipid membranes. In some instances, a nanopore described herein may comprise alpha hemolysin. In some instances, a nanopore described herein may comprise *Mycobacterium smegmatis* porin.

Solid state nanopores do not incorporate proteins into their systems. Instead, solid state nanopore technology uses various metal or metal alloy substrates with nanometer sized pores that allow samples to pass through. Solid state nanopores may be fabricated in a variety of materials including but not limited to, silicon nitride ($Si_3N_4$), silicon dioxide ($SiO_2$), and the like. In some instances, nanopore sequencing may comprise use of tunneling current, wherein a measurement of electron tunneling through bases as sample (ssDNA) translocates through the nanopore is obtained. In some instances, a nanopore system can have solid state pores with single walled carbon nanotubes across the diameter of the pore. In some instances, nanoelectrodes may be used on a nanopore system described herein. In some instances, fluorescence can be used with nanopores, for example solid state nanopores and fluorescence. For example, in such a system the fluorescence sequencing method converts each base of a sample into a characteristic representation of multiple nucleotides which bind to a fluorescent probe strand-forming dsDNA (were the sample comprises DNA). Where a two-color system is used, each base is identified by two separate fluorescence, and will therefore be converted into two specific sequences. Probes may consist of a fluorophore and quencher at the start and end of each sequence, respectively. Each fluorophore may be extinguished by the quencher at the end of the preceding sequence. When the dsDNA is translocating through a solid state nanopore, the probe strand may be stripped off, and the upstream fluorophore will fluoresce.

In some instances, a 1-100 nm channel or aperture may be formed through a solid substrate, usually a planar substrate, such as a membrane, through which an analyte, such as single stranded DNA, is induced to translocate. In other instances, a 2-50 nm channel or aperture is formed through a substrate; and in still other instances, a 2-30 nm, or a 2-20 nm, or a 3-30 nm, or a 3-20 nm, or a 3-10 nm channel or aperture if formed through a substrate.

In some instances, nanopores used in connection with the methods and devices useful herein are provided in the form of arrays, such as an array of clusters of nanopores, which may be disposed regularly on a planar surface. In some instances, clusters are each in a separate resolution limited area so that optical signals from nanopores of different clusters are distinguishable by the optical detection system employed, but optical signals from nanopores within the same cluster cannot necessarily be assigned to a specific nanopore within such cluster by the optical detection system employed.

Sequence Identity

The terms "homologous," "homology," or "percent homology" as used herein refer to the degree of sequence similarity between an amino acid or nucleotide sequence and a reference sequence. As used herein, the term "homology" can be used interchangeably with the term "identity." In some instances, the degree of sequence similarity herein can be at least about 60%, at least about 65%, at least about 70%, at least about 75%, at least about 80%, at least about 85%, at least about 90%, or at least about 95%, or about 100%. In some instances, percent sequence homology can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application. In some instances, percent homology of sequences can be determined using Smith-Waterman homology search algorithm. Smith & Waterman (1981) Adv. Appl. Math. 2: 482-489.

Percent homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues. Most sequence comparison method over longer sequences are designed to produce optimal alignments that take into consideration possible insertions and deletions without penalizing unduly the overall homology score. This is achieved by inserting "gaps" in the sequence alignment to try to maximize local homology. These more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is a commonly used gap scoring system. High gap penalties will of course produce optimized alignments with fewer gaps. Most alignment programs allow the gap penalties to be modified. Typically the default values are used when using such software for sequence comparisons. Calculation of maximum % homology therefore firstly requires the production of an optimal alignment, taking into consideration gap penalties. Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. In some instances, an alignment is determined by the Smith-Waterman homology search algorithm using an affine gap search with a gap open penalty of 12 a gap extension penalty of 2, and a blocks substitution matrix (BLOSUM) of 62.

Formulations

Also disclosed herein are formulations comprising: one or more nucleic acid constructs, one or more plants or seeds, one or more plant growth regulators, or any salt or solvate thereof, or any combination thereof. The formulation can be as a seed treatment, soil drench, granule formulation, or foliar spray to improve the productivity or alter the phenotype of a wide variety of crops.

Further disclosed herein are formulations comprising one or more nucleic acid construct described herein. The one or more nucleic acid constructs, salts or solvates can at least partially silence a gene a plant or seed. The one or more nucleic acid constructs can alter a phenotype of a gene in a plant or seed.

The formulation comprising one or more nucleic acid constructs, plants, or seeds can further comprise one or more strigolactones, salts, or solvates. The formulation can further comprise one or more plant growth regulators (PGRs), salts or solvates. The formulation can further comprise one or more inhibitors of abscisic acid (ABA) biosynthesis, or any salt or solvate thereof. The formulation can further comprise one or more strigolactones, salts, or solvates and one or more plant growth regulators (PGRs), salts, or solvates. The formulation can further comprise one or more strigolactones, salts, or solvates and one or more inhibitors of abscisic acid (ABA) biosynthesis, or any salt or solvate thereof. The formulation can further comprise one or more plant growth regulators (PGRs), salts, or solvates and one or more inhibitors of abscisic acid (ABA) biosynthesis, or any salt or solvate thereof.

In some cases, the formulations disclosed herein may further comprise one or more additives to facilitate nucleic acid delivery. In some instances, the additive may be a low or high molecular weight polyamine. In some instances, the additive may be polyethylenimine (PEI). In some instances, the additive may be a polyamidoamine (PAMAM) dendrimer. In some instances, the peptide may be a derivative of a viral protein. In some instances, the additive may be a cationic peptide. In some instances, the additive may be an arginine rich peptide (e.g. TAT). In some instances, the additive may be histidine rich peptide (e.g. endoporter). In some instances, the additive may be a lytic peptide (e.g. melittin).

The formulations may comprise at least about 0.1% (w/w) of an nucleic acid construct, plant, or seed, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the nucleic acid construct, plant, or seed.

The formulations may comprise less than about 95% (w/w) of an nucleic acid construct, plant, or seed, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the nucleic acid construct, plant, or seed.

The formulations may comprise about 0.1%-100% (w/w) of a nucleic acid construct, plant, or seed, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the nucleic acid construct, plant, or seed.

Plant Growth Regulators (PGRs)

The formulation can comprise one or more plant growth regulators (PGRs), salts, or solvates. PGRs can be numerous chemical substances that can influence the growth and/or differentiation of plant cells, tissues, or organs. Plant growth regulators can function as chemical messengers for intercellular communication. PGRs can include auxins, gibberellins, cytokinins, abscisic acid (ABA) and ethylene, brassinosteroids, and polyamines. They can work together coordinating the growth and/or development of cells. PGRs can elicit hydraulic enhancement of a plant. PGRs can increase the harvest yield of a plant. Auxins can comprise indole-3-acetic acid (IAA) or its derivative or chemical analog.

The formulation comprising one or more plant growth regulators (PGRs), salts, or solvates can further comprise one or more nucleic acid constructs or modified plants or seeds. The formulation comprising one or more plant growth regulators (PGRs), salts, or solvates can further comprise one or more strigolactones, salts, or solvates. The formulation comprising one or more plant growth regulators (PGRs), salts, or solvates can further comprise one or more inhibitors of abscisic acid (ABA) biosynthesis, or any salt or solvate thereof. The formulation comprising one or more plant growth regulators (PGRs), salts, or solvates can further comprise one or more nucleic acid constructs and one or more strigolactones, salts, or solvates. The formulation comprising one or more plant growth regulators (PGRs), salts, or solvates can further comprise one or more nucleic acid constructs and one or more inhibitors of abscisic acid (ABA) biosynthesis, or any salt or solvate thereof. The formulation comprising one or more plant growth regulators (PGRs), salts, or solvates can further comprise one or more strigolactones, salts, or solvates and one or more inhibitors of abscisic acid (ABA) biosynthesis, or any salt or solvate thereof.

The formulations may comprise at least about 0.1% (w/w) of a plant growth regulator (PGR), salt, or solvate, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the PGR, salt, or solvate.

The formulations may comprise less than about 95% (w/w) of a PGR, salt, or solvate, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the PGR, salt, or solvate.

The formulations may comprise about 0.1%-100% (w/w) of a PGR, salt, or solvate, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the PGR, salt, or solvate.

Auxins (e.g., IAA)

The formulations may comprise at least about 0.1% (w/w) of an auxin (e.g., IAA), for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the auxin (e.g., IAA).

The formulations may comprise less than about 95% (w/w) of an auxin (e.g., IAA), for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the auxin (e.g., IAA).

The formulations may comprise about 0.1%-100% (w/w) of an auxin (e.g., IAA), for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the auxin (e.g., IAA).

Gibberellins

The formulations may comprise one or more gibberellins, such as GA1, GA3, GA4, GA7, GA0, ent-gibberellane, ent-kaurene, their derivatives and chemical analogs. The formulations may comprise at least about 0.1% (w/w) of a gibberellin, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the gibberellin.

The formulations may comprise less than about 95% (w/w) of a gibberellin, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the gibberellin.

The formulations may comprise about 0.1%-100% (w/w) of a gibberellin, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the gibberellin.

Cytokinins

The formulations may comprise one or more cytokinins, such as kinetin, zeatin, 6-benzylaminopurine, diphenylurea, thidiazuron, their derivatives and chemical analogs. The formulations may comprise at least about 0.1% (w/w) of a cytokinin, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the cytokinin.

The formulations may comprise less than about 95% (w/w) of a cytokinin, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the cytokinin.

The formulations may comprise about 0.1%-100% (w/w) of a cytokinin, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the cytokinin.

Excipients

The formulations disclosed herein may further comprise one or more excipients. The one or more excipients can be one or more pesticides, one or more stabilizers, one or more additives, one or more carriers, one or more dispersants, one or more fertilizer, or any combination thereof. In one example, one or more excipients comprise acetone.

The formulations disclosed herein may further comprise one or more pesticides. The pesticide may be a biopesticide. A biopesticide may be a form of a pesticide that can be based on microorganisms or natural products. A biopesticide may include naturally occurring substances that control pests (biochemical pesticides), microorganisms that control pests (microbial pesticides), and pesticidal substances produced by plants containing added genetic material (plant-incorporated protectants) or PIPs. Examples of biopesticides can include, but are not limited to, gluocosinolate, chitosan, spinosad, alkaloids, terpenoids, phenolics, pyrethroids, rotenoids, nicotinoids, strychnine, scilliroside, canola oil and baking soda. The pesticide may be an organophosphate pesticide, carbamate pesticide, organochlorine insecticide, pyrethroid pesticide, sulfonylurea pesticides, or a combination thereof. The pesticide may be a herbicide, algicide, avidicide, bactericide, fungicide, insecticide, miticide, molluscicide, nematicide, rodenticide, virucide, or a combination thereof.

The formulations may further comprise one or more stabilizers and/or other additives. The stabilizers and/or additives can include, but are not limited to, penetration agents, adhesives, anticaking agents, dyes, dispersants, wetting agents, emulsifying agents, defoamers, antimicrobials, antifreeze, pigments, colorants, buffers, and carriers. The formulations may further comprise surfactants and/or adjuvants.

The formulations may further comprise one or more carriers. Examples of carriers include, but are not limited to, solid carriers, sponges, textiles, and synthetic materials. The synthetic material may be a porous synthetic material. Additional carriers can include organic carriers, such as waxes, linolin, paraffin, dextrose granules, sucrose granules and maltose-dextrose granules. Alternatively, the carrier can be an anorganic carrier such as natural clays, kaolin, pyrophyllite, bentonite, alumina, montmorillonite, kieselguhr, chalk, diatomaceous earths, calcium phosphates, calcium and magnesium carbonates, sulphur, lime, flours or talc. The formulation may be adsorbed into the carrier. The carrier may be characterized by enabling release of the compound, salt, solvate, or formulation.

The formulations may further comprise one or more dispersants. The dispersant may be a negatively charged anion dispersant. The dispersant may be a nonionic dispersant.

The formulations may further comprise fertilizer. The fertilizer may be a chemical fertilizer. The fertilizer may be an organic fertilizer. The fertilizer may be an inorganic fertilizer. The fertilizer may be a granulated or powdered fertilizer. The fertilizer may be a liquid fertilizer. The fertilizer may be a slow-release fertilizer.

The formulations disclosed herein may be formulated as a dry sprayable formulation. Examples of dry sprayable formulations can include, but are not limited to, wettable powders and water dispersible granules. Wettable powders may comprise nucleic acid constructs that have been microionized to powder form. Wettable powders may be applied as suspended particles after dispersion into water. Water dispersible granules may consist of granules that are applied after disintegration or dispersion in water. The water dispersible granules may comprise particles within the range of 0.2 to 4 mm. Water dispersible granules may be formed by agglomeration, spray drying, or extrusion techniques.

The formulations may be formulated as a liquid sprayable formulation. Examples of liquid sprayable formulations can include, but are not limited to, soluble concentrates, suspension concentrates, emulsifiable concentrates, microemulsions, oil dispersions, and microencapsulated particles. Suspension concentrates may comprise a stable suspension of the compound, salt, solvate, or formulation in a fluid usually intended for dilution with water before use. Emulsifiable concentrates may comprise a compound, salt, solvate, or formulation with an emulsifying agent in a water insoluble organic solvate which will form an emulsion when added to water. Microemulsions may comprise a compound, salt, solvate, or formulation with an emulsifying agent in a water insoluble organic solvate which will form a solution/emulsion when added to water.

The formulations may be formulated as a dry spreadable granule formulation. The dry spreadable granule formulation may comprise soil applied granule on inert or fertilizer carriers.

The formulations may be formulated as a seed treatment or seed dressing.

The formulations may be formulated for rapid release. The formulations may be formulated for slow release.

Methods

Also disclosed herein are methods of at least partially silencing a gene in an organism, e.g., plant or seed. The methods can comprise contacting the organism with the nucleic acid constructs disclosed herein, e.g., contacting the organism such as a seed, with a solution of nucleic acid constructs, or directly administering the nucleic acid constructs to the organism such as a leaf of a plant.

The nucleic acid constructs, plants, seeds, and formulations disclosed herein may be used in agriculture. The nucleic acid constructs, plants, seeds, and formulations may be used to promote plant growth. The nucleic acid constructs and formulations disclosed herein may be used for enhancing shoot stability in plants. The nucleic acid constructs, plants, seeds, and formulations may be used for increasing transport capacity in plants. The nucleic acid constructs, plants, seeds, and formulations may be used for increasing drought tolerance of a plant.

Further disclosed herein are methods of improving agriculture comprising applying a formulation comprising a nucleic acid construct to a plant or seed, thereby improving agriculture. Improving agriculture may comprise promoting plant growth. Improving agriculture may comprise enhancing shoot stability in plants. Improving agriculture may comprise increasing transport capacity in plants. Improving agriculture may comprise increasing drought tolerance. Improving agriculture may comprise reducing an application of one or more pesticides. Improving agriculture may comprise terminating application of one or more pesticides. Improving agriculture may comprise reducing watering amounts applied to the plants. Improving agriculture may comprise reducing watering frequency to the plants. Improving agriculture may comprise controlling phytopathogenic fungi. Improving agriculture may comprise controlling unwanted plant growth. Improving agriculture may comprise controlling unwanted insect or mite infestation. Improving agriculture may comprise regulating growth of the plant. Improving agriculture may comprise promoting or stimulating activity in one or more fungi.

Further disclosed herein are methods of controlling phytopathogenic fungi and/or unwanted plant growth and/or unwanted insect or mite infestation and/or for regulating the growth of plants. The methods may comprise use of a formulation comprising a nucleic acid construct disclosed herein to act on the respective pests, their habitat or the plants to be protected from the respective pest, to the soil and/or to unwanted plants and/or the crop plants and/or their habitat.

The nucleic acid constructs described herein may increase plant growth by at least about 5%. The nucleic acid constructs may increase plant growth by at least about 10%. The nucleic acid constructs may increase plant growth by at least about 15%. The nucleic acid constructs may increase plant growth by at least about 20%. The nucleic acid constructs may increase plant growth by at least about 25%. The nucleic acid constructs may increase plant growth by at least about 30%. The nucleic acid constructs may increase plant growth by at least about 50%. The nucleic acid constructs may increase plant growth by at least about 60%, 70%, 80%, 90%, 95%, 100% or more.

The nucleic acid constructs may increase plant growth by at least about 1.5, 2, 3, 4, 5, 6, 7, 8, 9, 10, 11, 12, 13, 14, 15, 16, 17, 18, 19, 20, 25, 30, 40, 50-fold or more. The nucleic acid constructs may increase plant growth by at least about 1.5-fold or more. The nucleic acid constructs may increase plant growth by at least about 2-fold or more. The nucleic acid constructs may increase plant growth by at least about 3-fold or more. The nucleic acid constructs may increase plant growth by at least about 5-fold or more. The nucleic acid constructs may increase plant growth by at least about 10-fold or more. Plant growth may comprise secondary plant growth.

The nucleic acid constructs may enhance shoot growth by at least about 5%. The nucleic acid constructs may enhance shoot growth by at least about 10%. The nucleic acid constructs may enhance shoot growth by at least about 15%. The nucleic acid constructs may enhance shoot growth by at least about 20%. The nucleic acid constructs may enhance shoot growth by at least about 25%. The nucleic acid constructs may enhance shoot growth by at least about 30%. The nucleic acid constructs may enhance shoot growth by at least about 50%. The nucleic acid constructs may enhance shoot growth by at least about 60%, 70%, 80%, 90%, 95%, 100% or more. The nucleic acid constructs may enhance shoot growth by at least about 1.5, 2, 3, 4, 5, 6, 7, 8, 9, 10, 11, 12, 13, 14, 15, 16, 17, 18, 19, 20, 25, 30, 40, 50-fold or more.

The nucleic acid constructs may enhance shoot growth by at least about 1.5-fold or more. The nucleic acid constructs may enhance shoot growth by at least about 2-fold or more. The nucleic acid constructs may enhance shoot growth by at least about 3-fold or more. The nucleic acid constructs may enhance shoot growth by at least about 5-fold or more. The nucleic acid constructs may enhance shoot growth by at least about 10-fold or more.

The nucleic acid constructs may increase transport capacity in plants by at least about 5%. The nucleic acid constructs may increase transport capacity in plants by at least about 10%. The nucleic acid constructs may increase transport capacity in plants by at least about 15%. The nucleic acid constructs may increase transport capacity in plants by at least about 20%. The nucleic acid constructs may increase transport capacity in plants by at least about 25%. The nucleic acid constructs may increase transport capacity in plants by at least about 30%. The nucleic acid constructs may increase transport capacity in plants by at least about 50%. The nucleic acid constructs may increase transport capacity in plants by at least about 60%, 70%, 80%, 90%, 95%, 100% or more.

The nucleic acid constructs may increase transport capacity in plants by at least about 1.5, 2, 3, 4, 5, 6, 7, 8, 9, 10, 11, 12, 13, 14, 15, 16, 17, 18, 19, 20, 25, 30, 40, 50-fold or more. The nucleic acid constructs may increase transport capacity in plants by at least about 1.5-fold or more. The nucleic acid constructs may increase transport capacity in plants by at least about 2-fold or more. The nucleic acid constructs may increase transport capacity in plants by at least about 3-fold or more. The nucleic acid constructs may increase transport capacity in plants by at least about 5-fold or more. The nucleic acid constructs may increase transport capacity in plants by at least about 10-fold or more.

The nucleic acid constructs may increase drought tolerance in plants by at least about 5%. The nucleic acid constructs may increase drought tolerance in plants by at least about 10%. The nucleic acid constructs may increase drought tolerance in plants by at least about 15%. The nucleic acid constructs may increase drought tolerance in plants by at least about 20%. The nucleic acid constructs may increase drought tolerance in plants by at least about 25%. The nucleic acid constructs may increase drought tolerance in plants by at least about 30%. The nucleic acid constructs may increase drought tolerance in plants by at least about 50%. The nucleic acid constructs may increase drought tolerance in plants by at least about 60%, 70%, 80%, 90%, 95%, 100% or more.

The nucleic acid constructs may increase drought tolerance in plants by at least about 1.5, 2, 3, 4, 5, 6, 7, 8, 9, 10, 11, 12, 13, 14, 15, 16, 17, 18, 19, 20, 25, 30, 40, 50-fold or more. The nucleic acid constructs may increase drought tolerance in plants by at least about 1.5-fold or more. The nucleic acid constructs may increase drought tolerance in plants by at least about 2-fold or more. The nucleic acid constructs may increase drought tolerance in plants by at least about 3-fold or more. The nucleic acid constructs may increase drought tolerance in plants by at least about 5-fold or more. The nucleic acid constructs may increase drought tolerance in plants by at least about 10-fold or more.

The nucleic acid constructs may reduce the application of one or more pesticides. Reducing the application of one or more pesticides may comprise reducing an amount of the one or more pesticides that are applied to the plant. The amount of the one or more pesticides applied to the plant may be reduced by at least about 1%, 5%, 10%, 15%, 20%, 25%, 30%, 35%, 40%, 50%, 60%, 70%, 80%, 90%, 95%, or 100%. The amount of the one or more pesticides applied to the plant may be reduced by at least about 10%. The amount of the one or more pesticides applied to the plant may be reduced by at least about 20%. The amount of the one or more pesticides applied to the plant may be reduced by at least about 30%. The amount of the one or more pesticides applied to the plant may be reduced by at least about 50%.

Alternatively, or additionally, reducing the application of the one or more pesticides may comprise reducing a frequency of which the one or more pesticides are applied to the plant. The frequency of which the one or more pesticides are applied to the plant may be reduced by at least about 1%, 5%, 10%, 15%, 20%, 25%, 30%, 35%, 40%, 50%, 60%, 70%, 80%, 90%, 95%, or 100%. The frequency of which the one or more pesticides are applied to the plant may be reduced by at least about 10%. The frequency of which the one or more pesticides are applied to the plant may be reduced by at least about 20%. The frequency of which the one or more pesticides are applied to the plant may be reduced by at least about 30%. The frequency of which the one or more pesticides are applied to the plant may be reduced by at least about 40%. The frequency of which the one or more pesticides are applied to the plant may be reduced by at least about 50%.

Use of the nucleic acid constructs may allow a reduction in the amount of water applied to the plants. The amount of the water applied to the plant may be reduced by at least about 1%, 5%, 10%, 15%, 20%, 25%, 30%, 35%, 40%, 50%, 60%, 70%, 80%, 90%, 95%, or 100%. The amount of the water applied to the plant may be reduced by at least about 10%. The amount of the water applied to the plant may be reduced by at least about 20%. The amount of the water applied to the plant may be reduced by at least about 30%. The amount of the water applied to the plant may be reduced by at least about 50%.

Use of the nucleic acid constructs may allow a reduction in the frequency of which the water is applied to the plant. The frequency of which the water is applied to the plant may be reduced by at least about 1%, 5%, 10%, 15%, 20%, 25%, 30%, 35%, 40%, 50%, 60%, 70%, 80%, 90%, 95%, or 100%. The frequency of which the water is applied to the plant may be reduced by at least about 10%. The frequency of which the water is applied to the plant may be reduced by at least about 20%. The frequency of which the water is applied to the plant may be reduced by at least about 30%. The frequency of which the water is applied to the plant may be reduced by at least about 40%. The frequency of which the water is applied to the plant may be reduced by at least about 50%.

The compound, salt, solvate, formulation disclosed herein may be used to control phytopathogenic fungi. Improving agriculture may comprise controlling unwanted plant growth. Controlling unwanted plant growth may comprise stimulating germination activity of the unwanted plant. The unwanted plant may be a parasitic plant. The unwanted plant may be a root parasitic plant. Examples of parasitic plants can include, but are not limited to, witchweeds (*Striga* spp.), broomrapes (*Orobanche* spp, *Phelipanche* spp), *Alectra*, dodders, and mistletoes. The unwanted plant may belong to the family Orobanchaceae. The unwanted plant may be witchweed. Examples of unwanted plants can include but are not limited to bindweed, poison sumac, Japanese knotweed, crabgrass, dandelion, plantain plant, ragweed plant, ground ivy, stinging nettle, creeping thistle, poison ivy, bittersweet, tansy, wisteria, ajuga, sweet autumn clematis, barberry, lantana, butterfly bush, common privet, kudzu or English ivy. The unwanted plant may be *Orobanche* spp. The compound, salt, solvate, or formulation may be applied directly to the unwanted plant. The compound, salt, solvate, or formulation may be applied indirectly to the unwanted plant.

The nucleic acid construct or formulation disclosed herein may be used to control unwanted insect or mite infestation. Examples of insects and mites can include, but are not limited to spiders, gnats, mealybugs, whiteflies, predator mites, spider mites and aphids.

The nucleic acid construct or formulation disclosed herein may be used to regulate growth of the plant. Regulating plant growth may comprise regulating plant breeding. Regulating plant growth may comprise inhibiting shoot branching. Regulating plant growth may comprise regulating one or more plant products. Regulating plant growth may comprise inhibiting root development.

The nucleic acid construct or formulation disclosed herein may be used to promote or stimulate activity in fungi. The compound, salt, solvate, or formulation may stimulate hyphal branching activity of one or more fungi. The compound, salt, solvate, or formulation may induce spore germination of one or more fungi. The one or more fungi may be arbuscular mycorrhizal (AM) fungi.

Further disclosed herein are methods of preserving or extending the life of a plant. Generally, the method may comprise contacting the plant with a nucleic acid construct or formulation disclosed herein.

The nucleic acid construct or formulation may be used to preserve or extend the life of a cut plant. The cut plant may be a flower. The cut plant may be a tree. The cut plant may be bush or shrub. The cut plant may be a vegetable. The compound, salt, solvate, or formulation may be used to preserve or extend the life of an uncut plant. The uncut plant may be a flower. The uncut plant may be a tree. The uncut plant may be bush or shrub. The uncut plant may be a vegetable. The compound, salt, solvate, or formulation may be used to preserve or extend the life of a potted plant. The potted plant may be a flower. The potted plant may be a tree. The potted plant may be bush or shrub. The potted plant may be a vegetable.

The nucleic acid construct or formulation may be used to preserve or extend the life of a flower. Examples of flowers can include, but are not limited to, lilies, daisies, roses, marigolds, Angel's trumpet, phlox, vinca, snapdragons, toadflax, orchids, ferns, black-eyed Susans, blood flowers, blue lobelias, morning glories, poppies, calendulas, geraniums, impatiens, lantanas, larkspurs, calla lilies, hyacinths, azaleas, pointsettias, and begonias.

The nucleic acid construct or formulation may be used to preserve or extend the life of a bush or shrub. Examples of bushes and shrubs can include, but are not limited to, forsynthia, fuchsia, hibiscus, currant, lilac, rose, hydrangea, willow, magnolia, thyme, snowberry, dogwood and holly.

The nucleic acid construct or formulation may be used to preserve or extend the life of a tree. Examples of trees can include, but are not limited to, cypress, poinsettia, palm, fir, pine, spruce, cedar, oak, mulberry, chestnut, hawthorn, poplar, and maple. The tree may be a fir tree. The fir tree may be a Douglas, Balsam or Fraser fir tree. The tree may be a pine tree. The pine tree may be a Scotch or White pine tree. The tree may be a spruce tree. The spruce tree may be a White, Norway or Blue spruce tree. The tree may be a cedar tree. The cedar tree may be a Deodara or Eastern red cedar.

The tree may be a cypress tree. The cypress tree may be an Arizona or Leland cypress tree.

The plant may be contacted with a nucleic acid construct or formulation disclosed herein, thereby extending or preserving the life of the plant. Contacting the plant with the nucleic acid construct or formulation may comprise administering the nucleic acid construct or formulation as a spray. Contacting the plant with the nucleic acid construct or formulation may comprise injecting the nucleic acid into the plant. Contacting the plant with the nucleic acid construct or formulation may comprise adding the plant growth material to the irrigation water of the plant. Contacting the plant with the nucleic acid construct or formulation may comprise applying the nucleic acid construct or formulation to the habitat of the plant. Contacting the plant with the nucleic acid construct or formulation may comprise adding the nucleic acid construct or formulation to a plant container (e.g., vase) and placing the plant in the plant container. Contacting the plant with the nucleic acid construct or formulation may comprise adding the nucleic acid construct or formulation to soil.

The life of the plant may be extended by at least about 1%, 5%, 10%, 15%, 20%, 25%, 30%, 35%, 40%, 45%, 50%, 55%, 60%, 65%, 70%, 75%, 80%, 85%, 90%, 95%, or 97% as compared to an untreated plant. The life of the plant may be extended by at least about 20% as compared to an untreated plant. The life of the plant may be extended by at least about 30% as compared to an untreated plant. The life of the plant may be extended by at least about 40% as compared to an untreated plant. The life of the plant may be extended by at least about 50% as compared to an untreated plant. The life of the plant may be extended by at least about 55% as compared to an untreated plant. The life of the plant may be extended by at least about 60% as compared to an untreated plant. The life of the plant may be extended by at least about 65% as compared to an untreated plant. The life of the plant may be extended by at least about 70% as compared to an untreated plant. The life of the plant may be extended by at least about 75% as compared to an untreated plant. The life of the plant may be extended by at least about 80% as compared to an untreated plant. The life of the plant can be determined by measuring the growth time between initial planting of a seed of the plant to the death of the plant.

The life of the plant may be extended by at least about 6, 12, 24, 30, 36, 42, 48, 54, 60, 66, 72, 78, 84, 90, 96, 102, 108, 114, or 120 hours as compared to an untreated plant. The life of the plant may be extended by at least about 24 hours as compared to an untreated plant. The life of the plant may be extended by at least about 36 hours as compared to an untreated plant. The life of the plant may be extended by at least about 48 hours as compared to an untreated plant. The life of the plant may be extended by at least about 72 hours as compared to an untreated plant. The life of the plant may be extended by at least about 96 hours as compared to an untreated plant.

The life of the plant may be extended by at least about 1, 1.5, 2, 2.5, 3, 3.5, 4, 4.5, 5, 5.5, 6, 6.5, or 7 days as compared to an untreated plant. The life of the plant may be extended by at least about 8, 9, 10, 11, 12, 13, 14, 15, 16, 17, 18, 19, or 20 days as compared to an untreated plant. The life of the plant may be extended by at least about 1 day as compared to an untreated plant. The life of the plant may be extended by at least about 2 days as compared to an untreated plant. The life of the plant may be extended by at least about 2.5 days as compared to an untreated plant. The life of the plant may be extended by at least about 3 days as compared to an untreated plant. The life of the plant may be extended by at least about 3.5 days as compared to an untreated plant. The life of the plant may be extended by at least about 4 days as compared to an untreated plant. The life of the plant may be extended by at least about 4.5 days as compared to an untreated plant.

The life of the plant may be extended by at least about 1, 1.5, 2, 2.5, 3, 3.5, 4, 4.5, 5, 5.5, 6, 6.5, or 7 weeks as compared to an untreated plant. The life of the plant may be extended by at least about 8, 9, 10, 11, 12, 13, 14, 15, 16, 17, 18, 19, or 20 weeks as compared to an untreated plant. The life of the plant may be extended by at least about 1, 1.5, 2, 2.5, 3, 3.5, 4, 4.5, 5, 5.5, 6, 6.5, or 7 months as compared to an untreated plant. The life of the plant may be extended by at least about 8, 9, 10, 11, 12, 13, 14, 15, 16, 17, 18, 19, or 20 months as compared to an untreated plant.

Preserving or extending the life of the plant may comprise reducing wilting of the plant. Reducing wilting of the plant may comprise reducing flower or leaf rolling of the plant. The wilting of the plant may be reduced by at least about 1%, 5%, 10%, 15%, 20%, 25%, 30%, 35%, 40%, 45%, 50%, 55%, 60%, 65%, 70%, 75%, 80%, 85%, 90%, 95%, or 97% as compared to an untreated plant. The wilting of the plant may be reduced by at least about 10% as compared to an untreated plant. The wilting of the plant may be reduced by at least about 30% as compared to an untreated plant. The wilting of the plant may be reduced by at least about 50% as compared to an untreated plant. The wilting of the plant may be reduced by at least about 70% as compared to an untreated plant. The wilting of the plant may be reduced by at least about 80% as compared to an untreated plant.

A sign of plant stress may include wilting of the plant. For example, stressed plants may have rolled leaves or petals. The plant growth materials disclosed herein may promote the life of the plant by reducing the wilting of the plant. Reducing the wilting of the plant may comprise delaying the wilting of the plant as compared to an untreated plant. For example, an untreated cut plant may show signs of wilting within 36 hours of being cut, however, a cut plant treated with a plant growth material may have delayed wilting. The wilting of the plant may be delayed by at least about 2, 3, 4, 5, 6, 7, 8, 9, 10, 11, 12, 13, 14, 15, 16, 17, 18, 19, 20, 21, 22, 23, or 24 hours as compared to an untreated plant. The wilting of the plant may be delayed by at least about 12 hours as compared to an untreated plant. The wilting of the plant may be delayed by at least about 24 hours as compared to an untreated plant. The wilting of the plant may be delayed by at least about 36 hours as compared to an untreated plant. The wilting of the plant may be delayed by at least about 48 hours as compared to an untreated plant.

An additional sign of plant stress may include reduced turgidity. Turgidity may refer to pressure caused by the osmotic flow of water from an area of low solute concentration outside of the cell into the cell cell's vacuole. Turgidity may be used by plants to maintain rigidity. Often, healthy plants are turgid, whereas, unhealthy plants are less turgid. Preserving or extending the life of the plant may comprise prolonging or maintaining the turgidity of the plant. The turgidity of the plant may be greater than the turgidity of an untreated plant. The turgidity of the plant may be at least about 1%, 5%, 10%, 15%, 20%, 25%, 30%, 35%, 40%, 45%, 50%, 55%, 60%, 65%, 70%, 75%, 80%, 85%, 90%, 95%, or 97% greater than the turgidity of an untreated plant. The turgidity of the plant may be at least about 10% greater than the turgidity of an untreated plant. The turgidity of the plant may be at least about 15% greater than the turgidity of an untreated plant. The turgidity of the plant may be at least about 25% greater than the turgidity of an untreated plant. The turgidity of the plant may be at least about 35% greater than the turgidity of an untreated plant. The turgidity of the plant may be at least about 45% greater than the turgidity of an untreated plant. The turgidity of the plant may be at least about 60% greater than the turgidity of an untreated plant. The turgidity of the plant may be at least about 75% greater than the turgidity of an untreated plant.

A stressed plant may also show a reduction in the turgid state. The turgid state may refer to a period of time in which the plant maintains its rigidity. The rigidity of the plant may refer to the rigidity of the stem of the plant. For example, as cut plants die, the stem of the plant may be less rigid, thereby causing the cut plant to fall over or bend. A stressed plant may be unable to hold itself upright. Preserving or extending the life of the plant may comprise prolonging the turgid state of the plant. The turgid state of the plant may be increased by at least about 1%, 5%, 10%, 15%, 20%, 25%, 30%, 35%, 40%, 45%, 50%, 55%, 60%, 65%, 70%, 75%, 80%, 85%, 90%, 95%, or 97% as compared to an untreated plant. The turgid state of the plant may be increased by at least about 20% as compared to an untreated plant. The turgid state of the plant may be increased by at least about 30% as compared to an untreated plant. The turgid state of the plant may be increased by at least about 40% as compared to an untreated plant. The turgid state of the plant may be increased by at least about 50% as compared to an untreated plant.

The turgid state of the plant may be increased by at least about 2, 3, 4, 5, 6, 7, 8, 9, 10, 11, 12, 13, 14, 15, 16, 17, 18, 19, 20, 21, 22, 23, or 24 hours as compared to an untreated plant. The turgid state of the plant may be increased by at least about 6 hours as compared to an untreated plant. The turgid state of the plant may be increased by at least about 12 hours as compared to an untreated plant. The turgid state of the plant may be increased by at least about 24 hours as compared to an untreated plant.

A stressed plant may lose leaves or petals. Contacting a plant with a plant growth material may reduce or delay the loss of one or more petals or leaves of the plant. For example, an untreated plant may lose 50% of its leaves or petals, whereas a treated plant may lose 10-25% of its leaves or petals. The loss of the one or more petals of the plant may be reduced by least about 1%, 5%, 10%, 15%, 20%, 25%, 30%, 35%, 40%, 45%, 50%, 55%, 60%, 65%, 70%, 75%, 80%, 85%, 90%, 95%, or 97% as compared to the loss of the one or more petals of an untreated plant. The loss of the one or more petals of the plant may be reduced by least about 10% as compared to the loss of the one or more petals of an untreated plant. The loss of the one or more petals of the plant may be reduced by least about 20% as compared to the loss of the one or more petals of an untreated plant. The loss of the one or more petals of the plant may be reduced by least about 35% as compared to the loss of the one or more petals of an untreated plant. The loss of the one or more petals of the plant may be reduced by least about 50% as compared to the loss of the one or more petals of an untreated plant. The loss of the one or more petals of the plant may be reduced by least about 60% as compared to the loss of the one or more petals of an untreated plant. The loss of the one or more petals of the plant may be reduced by least about 70% as compared to the loss of the one or more petals of an untreated plant.

The loss of the one or more petals of the plant may be delayed by at least about 2, 3, 4, 5, 6, 7, 8, 9, 10, 11, 12, 13, 14, 15, 16, 17, 18, 19, 20, 21, 22, 23, or 24 hours as compared to the loss of one or more petals of an untreated plant. The loss of the one or more petals of the plant may be delayed by at least about 25, 30, 35, 40, 45, 50, 55, 60, 65, 70, 75, 80, 85, 90, 95 or 100 hours as compared to the loss of one or more petals of an untreated plant. The loss of the one or more petals of the plant may be delayed by at least about 6 hours as compared to the loss of one or more petals of an untreated plant. The loss of the one or more petals of the plant may be delayed by at least about 12 hours as compared to the loss of one or more petals of an untreated plant. The loss of the one or more petals of the plant may be delayed by at least about 18 hours as compared to the loss of one or more petals of an untreated plant. The loss of the one or more petals of the plant may be delayed by at least about 36 hours as compared to the loss of one or more petals of an untreated plant. The loss of the one or more petals of the plant may be delayed by at least about 48 hours as compared to the loss of one or more petals of an untreated plant. The loss of the one or more petals of the plant may be delayed by at least about 60 hours as compared to the loss of one or more petals of an untreated plant. The loss of the one or more petals of the plant may be delayed by at least about 72 hours as compared to the loss of one or more petals of an untreated plant. The loss of the one or more petals of the plant may be delayed by at least about 96 hours as compared to the loss of one or more petals of an untreated plant.

A stressed plant may show signs of discoloration. The stressed plant may appear brownish. Alternatively, or additionally, the stressed plant shows a reduction in the appearance of green leaves. The chlorophyll content of the stressed plant may also be reduced. Preserving or extending the life of the plant may comprise maintaining the chlorophyll content of the plant. For example, a reduction in the chlorophyll content of an untreated plant may appear within 48 hours of being cut. However, a reduction in the chlorophyll content of a treated plant may appear after 60 hours of being cut. The chlorophyll content of the plant may be maintained for at least about 2, 3, 4, 5, 6, 7, 8, 9, 10, 11, 12, 13, 14, 15, 16, 17, 18, 19, 20, 21, 22, 23, or 24 hours. The chlorophyll content of the plant may be maintained for at least about 6 hours. The chlorophyll content of the plant may be maintained for at least about 12 hours. The chlorophyll content of the plant may be maintained for at least about 24 hours. Discoloration such as leaf firing (premature yellowing) may occur as a result of poor nutrient availability, and can be an indicator of poor plant health. For, example, leaf firing may be a result of nitrogen deficiency.

Preserving or extending the life of the plant may comprise reducing or delaying the loss of the chlorophyll content of the plant. The chlorophyll content of the plant may be greater than the chlorophyll content of an untreated plant. The chlorophyll content of the plant may be at least about 1%, 5%, 10%, 15%, 20%, 25%, 30%, 35%, 40%, 45%, or 50% greater than the content of an untreated plant. The chlorophyll content of the plant may be at least about 55%, 60%, 65%, 70%, 75%, 80%, 85%, 90%, 95% or 97% greater than the content of an untreated plant. The chlorophyll content of the plant may be at least about 20% greater than the content of an untreated plant. The chlorophyll content of the plant may be at least about 30% greater than the content of an untreated plant. The chlorophyll content of the plant may be at least about 40% greater than the content of an untreated plant. The chlorophyll content of the plant may be at least about 50% greater than the content of an untreated plant. The chlorophyll content of the plant may be at least about 60% greater than the content of an untreated plant. The chlorophyll content of the plant may be at least about 1.5, 2, 2.5, 3, 3.5, 4, 4.5, 5, 5.5, 6, 6.5, 7, 8, 9, or 10-fold greater than the content of an untreated plant. The chlorophyll content of the plant may be at least about 11, 12, 13, 14, 15, 16, 17, 18, 19, 20, 25, 30, 35, 40, 45, 50, 55, 60, 65, 70, 75, 80, 85, 90, 95 or 100-fold greater than the content of an untreated plant. The chlorophyll content of the plant may be at least about 2-fold greater than the content of an untreated plant. The chlorophyll content of the plant may be at least about 3-fold greater than the content of an untreated plant. The chlorophyll content of the plant may be at least about 4-fold greater than the content of an untreated plant. The chlorophyll content of the plant may be at least about 5-fold greater than the content of an untreated plant. The chlorophyll content of the plant may be at least about 10-fold greater than the content of an untreated plant.

The loss of the chlorophyll content of the plant may be delayed by at least about 2, 3, 4, 5, 6, 7, 8, 9, 10, 11, 12, 13, 14, 15, 16, 17, 18, 19, 20, 21, 22, 23, or 24 hours as compared to the loss of the chlorophyll content of an untreated plant. The loss of the chlorophyll content of the plant may be delayed by at least about 30, 35, 40, 45, 50, 55, 60, 65, 70, 75, 80, 85, 90, 95, or 100 hours as compared to the loss of the chlorophyll content of an untreated plant. The loss of the chlorophyll content of the plant may be delayed by at least about 6 hours as compared to the loss of the chlorophyll content of an untreated plant. The loss of the chlorophyll content of the plant may be delayed by at least about 12 hours as compared to the loss of the chlorophyll content of an untreated plant. The loss of the chlorophyll content of the plant may be delayed by at least about 24 hours as compared to the loss of the chlorophyll content of an untreated plant. The loss of the chlorophyll content of the plant may be delayed by at least about 36 hours as compared to the loss of the chlorophyll content of an untreated plant. The loss of the chlorophyll content of the plant may be delayed by at least about 48 hours as compared to the loss of the chlorophyll content of an untreated plant. The loss of the chlorophyll content of the plant may be delayed by at least about 60 hours as compared to the loss of the chlorophyll content of an untreated plant. The loss of the chlorophyll content of the plant may be delayed by at least about 72 hours as compared to the loss of the chlorophyll content of an untreated plant.

The loss of the chlorophyll content of the plant may be less than the loss of the chlorophyll content of an untreated plant. The loss of the chlorophyll content of the plant may be at least about 1%, 5%, 10%, 15%, 20%, 25%, 30%, 35%, 40%, 45%, 50%, 55%, or 60% less than the loss of the chlorophyll content of an untreated plant. The loss of the chlorophyll content of the plant may be at least about 65%, 70%, 72%, 75%, 77%, 80%, 85%, 90%, 92%, 95%, or 97% less than the loss of the chlorophyll content of an untreated plant. The loss of the chlorophyll content of the plant may be at least about 5% less than the loss of the chlorophyll content of an untreated plant. The loss of the chlorophyll content of the plant may be at least about 10% less than the loss of the chlorophyll content of an untreated plant. The loss of the chlorophyll content of the plant may be at least about 20% less than the loss of the chlorophyll content of an untreated plant. The loss of the chlorophyll content of the plant may be at least about 30% less than the loss of the chlorophyll content of an untreated plant. The loss of the chlorophyll content of the plant may be at least about 40% less than the loss of the chlorophyll content of an untreated plant. The loss of the chlorophyll content of the plant may be at least about 50% less than the loss of the chlorophyll content of an untreated plant. The loss of the chlorophyll content of the plant may be at least about 60% less than the loss of the chlorophyll content of an untreated plant.

The loss of the chlorophyll content of the plant may be at least about 1.5, 2, 2.5, 3, 3.5, 4, 4.5, 5, 5.5, 6, 6.5, 7, 7.5, 8, 8.5, 9, 9.5, or 10-fold less than the loss of the chlorophyll content of an untreated plant. The loss of the chlorophyll content of the plant may be at least about 11, 12, 13, 14, 15, 16, 17, 18, 19, 20, 25, 30, 35, 40, 45, 50, 55, 60, 65, 70, 75, 80, 85, 90, 95 or 100-fold less than the loss of the chlorophyll content of an untreated plant. The loss of the chlorophyll content of the plant may be at least about 2-fold less than the loss of the chlorophyll content of an untreated plant. The loss of the chlorophyll content of the plant may be at least about 3-fold less than the loss of the chlorophyll content of an untreated plant. The loss of the chlorophyll content of the plant may be at least about 5-fold less than the loss of the chlorophyll content of an untreated plant. The loss of the chlorophyll content of the plant may be at least about 10-fold less than the loss of the chlorophyll content of an untreated plant.

The nucleic acid construct or formulation may be applied directly to the plant. The nucleic acid construct or formulation may be applied to one or more parts of the plant. The one or more parts of the plant may comprise a terminal bud, flower, lateral bud, leaf blade, leaf axil, node, internode, petiole, primary root, lateral root, root hair, root cap, or a combination thereof. The formulations may be applied to the leaf blade of the plant. The formulations may be applied to the root of the plant.

Alternatively, or additionally, the nucleic acid construct or formulation can be applied to a soil. The formulation may be applied to an area around the plant. The area around the plant may comprise soil. The area around the plant may comprise an adjacent plant. The formulation may be applied to a soil before placing a plant or seed in the soil. The formulation may be applied to bacterial consortium present in the soil. The formulation may be applied with additional bacteria to supplement the natural bacterial consortium in the soil.

The nucleic acid construct or formulation may be applied to a plant that is susceptible to a parasitic weed. Examples of plants include, but are not limited to, corn, rice, sorghum, millets, and sugar cane. The plant may be corn. The plant may be tobacco. The plant may be rice.

The nucleic acid construct or formulation may improve taste or texture of an edible product of the plant. In non-limiting examples, the targeted gene may be control sugar and/or starch biosynthesis or storage. The targeted gene may control tannin biosynthesis. The targeted gene may control anthocyanin biosynthesis. The target gene may control metabolite biosynthesis.

The nucleic acid construct may improve nutritional content of the plant, for example, by increasing or decreasing sugar, starch, protein, and/or fat content of an edible product of the plant, enhancing the accumulation of vitamins and/or minerals in the plant. The targeted gene may control sugar biosynthesis, carbohydrate biosynthesis and/or storage, protein biosynthesis and/or degradation, and/or secondary metabolite biosynthesis.

The nucleic acid construct may increase the shelf life of an edible product of the plant, for example by decreasing ethylene biosynthesis in the plant. The targeted gene may control ethylene biosynthesis.

The nucleic acid construct or formulation may be applied as a seed coating. The nucleic acid construct or formulation may be applied as a seed treatment. The nucleic acid construct or formulation may be applied as a seed dressing. The nucleic acid construct or formulation may be applied as a spray. The nucleic acid construct or formulation may be applied as a foliar spray. The nucleic acid construct or formulation may be applied as a powder. The powder may be a wettable powder.

In some instances, the measurements described herein can be made at a temperature of about 1, 2, 3, 4, 5, 6, 7, 8, 9, 10, 11, 12, 13, 14, 15, 16, 17, 18, 19, 20, 21, 22, 23, 24, 25, 6, 27, 28, 29, 30, 31, 32, 33, 34, 35, 36, 37, 38, 39, or 40° C.

Kits

Also provided are kits that find use in practicing the subject methods, as mentioned above. A kit can include one or more of the compositions described herein. A kit can include at least nucleic acid construct. A kit can include at least one engineered plant or seed.

A kit can include one or more reagents for performing administration of nucleic acid constructs to plants or seeds (e.g., polynucleotides, buffers, cations, etc.), and the like. Additional reagents that are desired in the protocol to be practiced with the kit components may be present. Such additional reagents include, but are not limited to, one or more of the following an enzyme or combination of enzymes such as a polymerase, reverse transcriptase, nickase, restriction endonuclease, uracil-DNA glycosylase enzyme, enzyme that methylates or demethylates DNA, endonuclease, ligase, etc.

The kit components may be present in separate containers, or one or more of the components may be present in the same container, where the containers may be storage containers and/or containers that are employed during the assay for which the kit is designed.

In addition to the above components, the subject kits may further include instructions for practicing the subject methods. These instructions may be present in the subject kits in a variety of forms, such as printed information on a suitable medium or substrate (e.g., a piece or pieces of paper on which the information is printed), in the packaging of the kit, in a package insert, etc. Yet another means would be a computer readable medium (e.g., diskette, CD, etc.), on which the information has been recorded. Yet another means that may be present is a website address which may be used via the internet to access the information at a removed site.

Communicating Results

The present disclosure provides the communication of assay results or diagnoses or both to technicians, physicians or subjects, for example. In certain instances, computers will be used to communicate results of the methods herein to interested parties, e.g., customers, technicians, physicians and their subjects, etc. In some instances, the methods can be performed, or results analyzed in a country or jurisdiction which differs from the country or jurisdiction to which the results are communicated. In some instances, a result may be communicated to the subject as soon as possible after the diagnosis is obtained. The results may be sent to a subject by email or communicated to the subject by phone. A computer may be used to communicate the result by email or phone. In certain instances, the message containing result may be generated and delivered automatically to the subject using a combination of computer hardware and software which will be familiar to artisans skilled in telecommunications. In certain instances or some of the method steps, including the preparation of plants and seeds, and communicating of assay results, may be carried out in diverse (e.g., foreign) jurisdictions.

The section headings used herein are for organizational purposes only and are not to be construed as limiting the subject matter described.

It is to be understood that the methods and compositions described herein are not limited to the particular methodology, protocols, cell lines, constructs, and reagents described herein and as such may vary. It is also to be understood that the terminology used herein is for the purpose of describing particular instances only, and is not intended to limit the scope of the methods and compositions described herein, which will be limited only by the appended claims. While preferred instances of the present disclosure have been shown and described herein, it will be obvious to those skilled in the art that such instances are provided by way of example only. Numerous variations, changes, and substitutions will now occur to those skilled in the art without departing from the disclosure. It should be understood that various alternatives to the instances of the disclosure described herein may be employed in practicing the disclosure. It is intended that the following claims define the scope of the disclosure and that methods and structures within the scope of these claims and their equivalents be covered thereby.

Several aspects are described with reference to example applications for illustration. Unless otherwise indicated, any instance can be combined with any other instance. It should be understood that numerous specific details, relationships, and methods are set forth to provide a full understanding of the features described herein. A skilled artisan, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

EXAMPLES

Example 1—Preparation of CATS Oligonucleotide Nucleic Acid Construct Solutions

Oligonucleotides were custom synthesized. 96 well oligo plates were obtained; one plate for each locu of interest. Pooled stocks for each oligo plate were made by taking 20 uL of a 400 uM stock from each well of that plate and combining these in a 2 mL tube. Afterwards, each pooled sock was combined in a 12 mL sterile falcon tube, mixed by pipetting, and briefly centrifuged to collect all contents. This pooled oligo mix was then pipetted into two eight-well PCT strip tubes and spun down. Tubes were placed in a PTC-200 Thermal cycler at 95 degrees for 1 minute to denature contents, and then cooled at room temperature for 10 minutes. Contents of strip tubes were again combined in a fresh sterile 12 mL falcon tube, mixed by pipetting and centrifuged briefly to collect contents. Applications of serial dilution of this full-strength oligo mix were applied to plants. Representative sequences of oligonucleotides are shown in SEQ ID NOs 1-664.

Example 2—Application of CATS Nucleotides to Plants and Seeds

Vacuum Treatment Method in Corn

Five 20 mL clear glass scintillation vials were obtained, and six B73 Maize seeds were place in each vial, lying flat.

Seeds in vials 1-4 received 900 uL of an oligo treatment (full strength, 1/10, 1/100, and 1/1000, respectively) and seeds in vial 5 received 900 uL of water. After incubating for 20 minutes, caps were removed from all five vials, which were then placed in an airtight chamber and vacuumed 18 hours at 400 mbar. After 18 hours, vials were removed from the vacuum and each seed was planted in 100 mm² plastic pot filled with moistened Sunshine Mix No. 4. Seeds were left to germinate under next light Veg 8 LED panels set to long day conditions.

Germination and Outgrowth in Solution Method

Five 20 mL clear glass scintillation vials were obtained, and six B73 Maize seeds were placed in each vial, lying flat. Seeds in vials 1-4 received 900 uL of an oligo treatment (full strength, 1/10, 1/100, and 1/1000, respectively) and seeds in vial 5 received 900 uL of water. Vials were placed in the dark with caps on and seeds were left to germinate, for 4 days. Once epicotyls had emerged, vials were removed from dark, embryos were removed from treatment solutions, and each was planted in 100 mm² plastic pot filled with moistened Sunshine Mix No. 4.

Syringe Infiltration Method

CATS oligonucleotide solutions described above can be administered directly to plant tissue by syringe in order to locally deliver the oligonucleotides to a particular location on the plant.

Example 3—Targeting the Phytoene Desaturase (PDS1) in Maize

CATS oligonucleotides were constructed in to target the phytoene desaturase, an enzyme involved in the synthesis of carotenoids in plants. Mutations or knockouts of this gene result in albino phenotypes.

Figure 3:
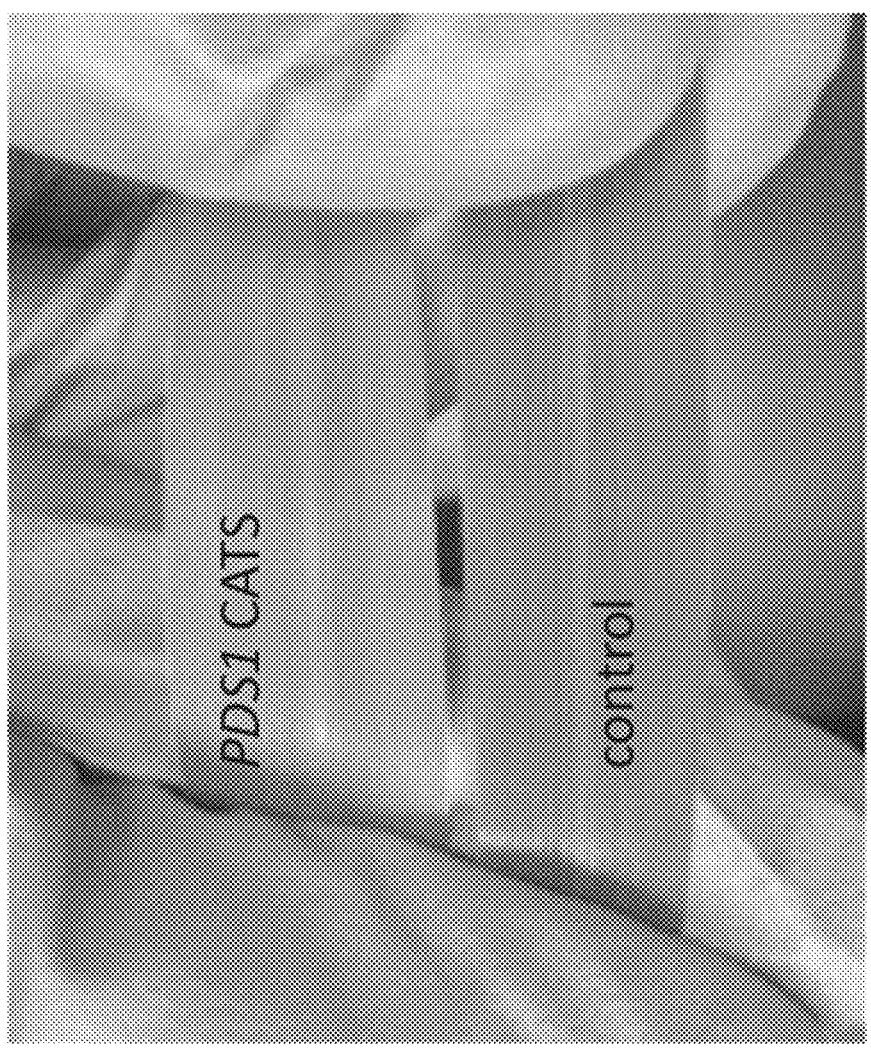
FIG. 3 depicts the result of silencing a PDS1 gene in maize by treatment with CATS oligonucleotides. PDS1-CATS plants show a pale green leaf phenotype (upper leaf), as compared to a control maize plant (lower leaf).

A total of 62 oligonucleotides (31 oligonucleotide pairs, shown in SEQ ID NOs:1-62) were synthesized targeting transcription regulatory regions upstream of PDS1 gene open reading frame in a maize plant. The mixture of oligonucleotides was applied to maize seeds, and seedlings grown from the seeds. PDS1-CATS plants showed pale green leaf phenotype compared to the uncontacted control plants (FIG. 3).

Figure 4:
FIG. 4 depicts the results of silencing a PDS1 gene in maize plants by treatment with CATS oligonucleotides using an infiltration administration method.

Administration of CATS oligonucleotides directly to a maize leaf by syringe infiltration results in local loss of pigmentation (FIG. 4).

Confirmation of DNA Methylation by Bisulfite Sequencing

Figure 5:
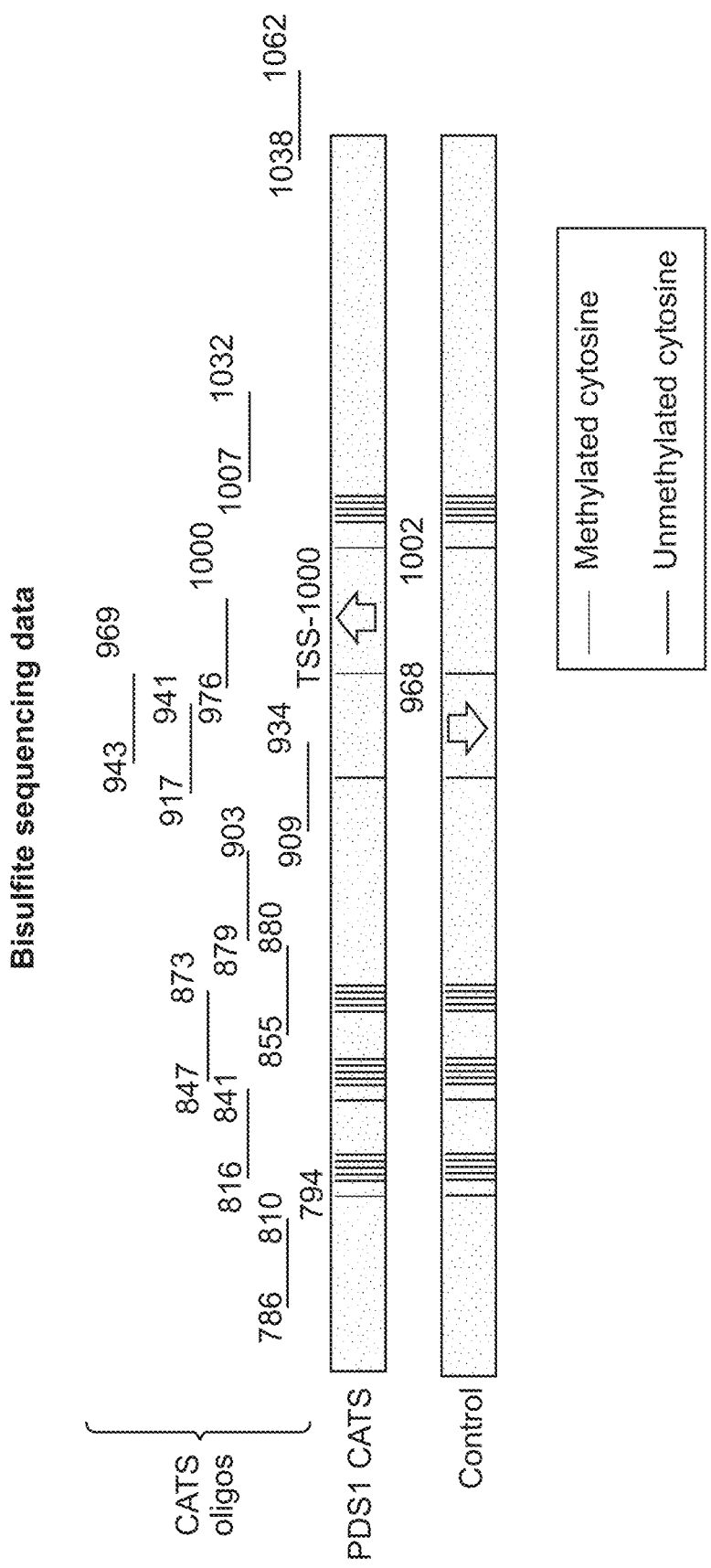
FIG. 5 depicts bisulfite sequencing analysis of a PDS1 gene in CATS-treated maize plants. Treatment with CATS oligonucleotides results in methylated cytosines upstream of the PDS1 open reading frame.

Leaf tissue from sterile scissors were cut and placed in a chilled (LN2) closed cap tube with one medium glass bead. Leaf tissue was bead beated for 1:30 at 1800 RPN. DNA was extracted using the PureLink Plant Total DNA extraction kit. A total of 20 µL of DNA from the extraction was used with Zymo Research Corp Easy DNA Methylation kit. Human standards were used to confirm the kit was working. Primers were designed using MethPrimer2 (http://www.urogene.org/cgi-bin/methprimer2/MethPrimer.cgi) and allowing degeneracy in the primers if necessary. Bi-sulfite treated DNA from the kit was used to perform a PCR reaction using 12.5 µL Zymotaq, 1 µL primer-F, 1 µL primer-R, 4 µL BS treated DNA and 7.5 µL water. The first set of BS-PCR primers were amplified at 50° C. and cover GC islands. Amplicons were sequence cloned to confirm. Initial analysis of the sequenced data indicates that some of the cytosines were methylated (FIG. 5).

Example 4—Targeting the LZY1 Gravitropism Regulator in Maize

The plant regulator Lazy1 (LZY1) is known to control the plant's shoot gravitropism. In wildtype plants, shoots grow in the opposite direction of gravity and respond to changes in orientation by bending to maintain this directionality. In contrast, mutants in LZY1 expression do not respond to changes in orientation. CATS oligos were designed to target the LZY1 regulator. A total of 132 oligonucleotides (67 oligonucleotide pairs, shown in SEQ ID NOs: 63-194) were synthesized targeting transcription regulatory regions upstream of LZY1 gene open reading frame in a maize plant. The mixture of oligonucleotides was applied to maize seeds, and seedlings grown from the seeds.

Figure 6B:
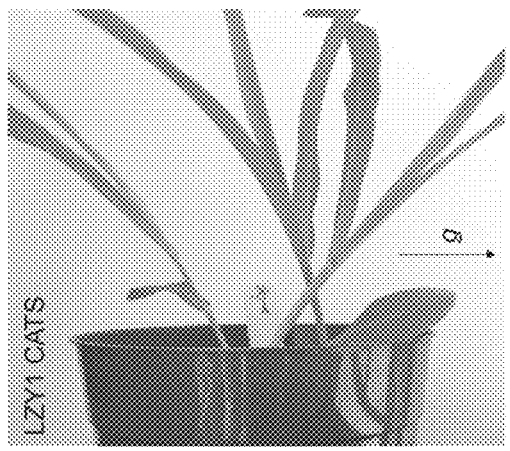
FIGS. 6A-6D depict the result of silencing a LZY1 gene in maize by treatment with CATS oligonucleotides.
Figure 6D:
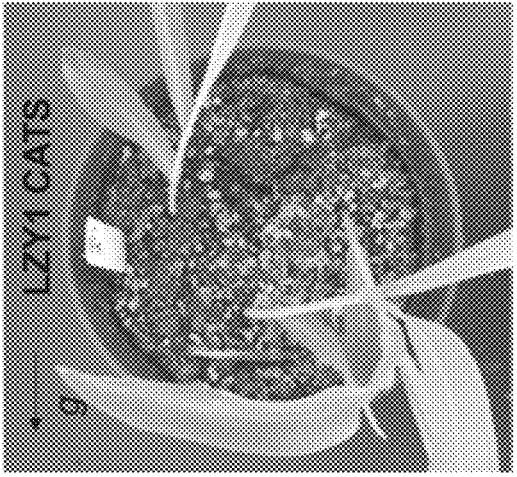
Figure 6A:
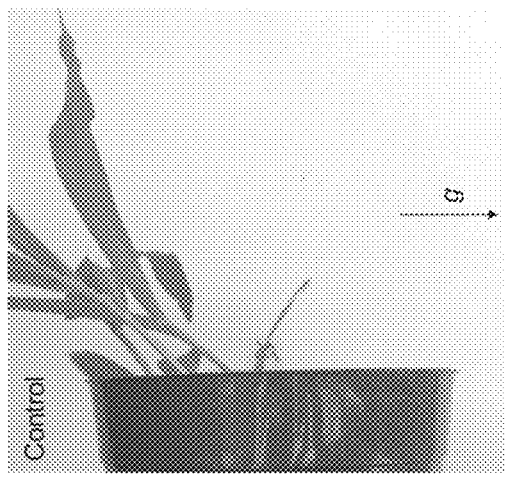
Figure 6C:
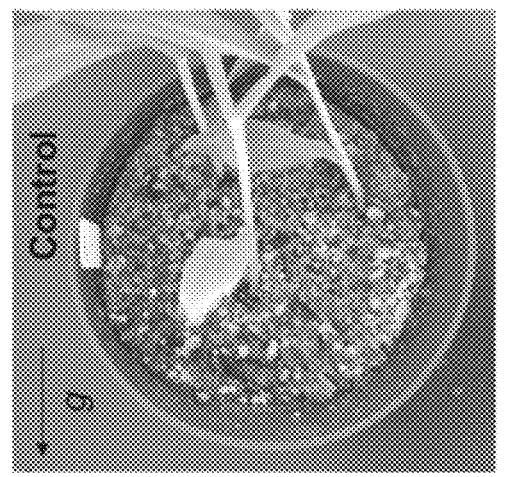

As shown in FIGS. 6B and 6D, CATS::LZY1 seedlings display reduced or absent gravitropism when turned on their side, as compared to unmodified plants (FIGS. 6A and 6C), where the control plants display a strong gravitropic response.

Example 5—Targeting Polyphenol Oxidases in Potato

Figure 7A:
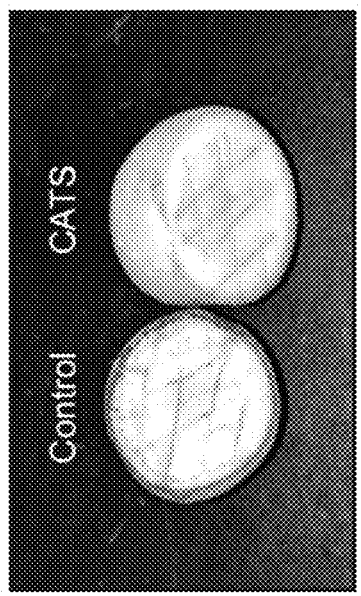
FIGS. 7A-7C depict the result of silencing a polyphenol oxidase (PPO) gene in potato plants.
Figure 7C:
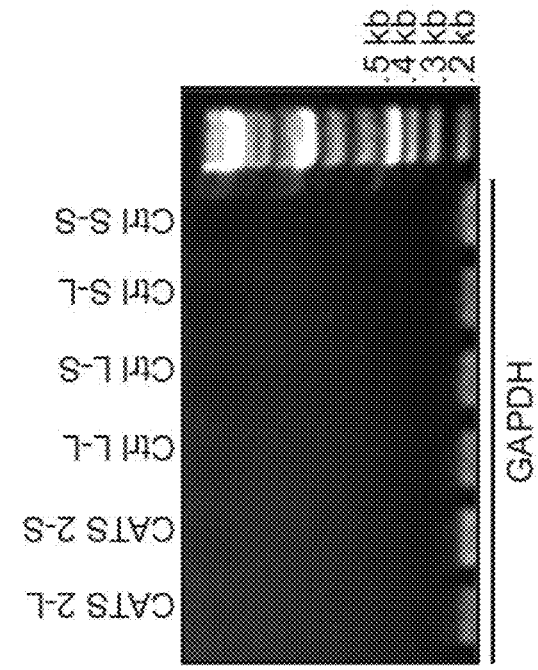
Figure 7B:
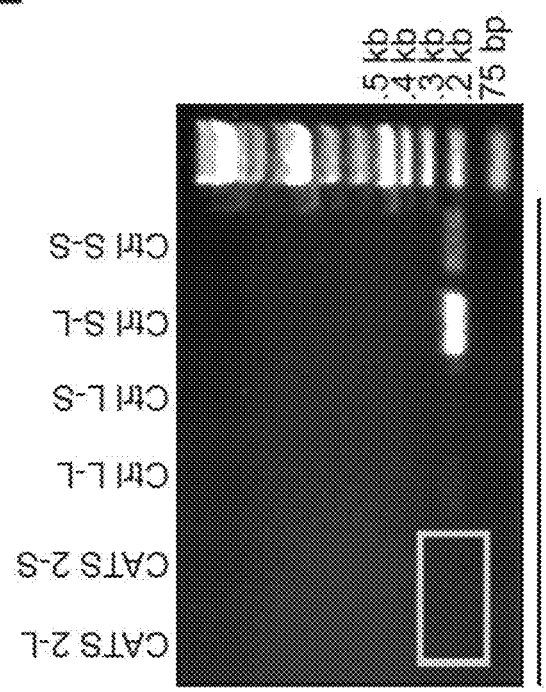

The polyphenol enzyme oxidase (PPO) enzymes in plants are responsible for the enzymatic browning phenotype that occurs after cutting or wounding of the plant. Non-browning crops are desirable from a consumer acceptance and food waste perspective. To achieve non-browning potatoes, CATS oligos were designed to simultaneously target the 7 PPO alleles in potato (*Solanum tuberosum*). A total of 210 individual oligos (105 oligo pairs, shown in SEQ ID NOs: 195-404) were applied to seed potatoes using the 'outgrowth in solution' method above. Plants were grown in greenhouse conditions and tubers were harvested approximately 3 months after planting. RT-PCT analysis of PPO mRNA levels indicated that CATS plants had reduced levels of the transcript (FIG. 7B), and phenotype analysis shows that tubers from CATS plants had greatly reduced enzymatic browning when cut, as compared to the potatoes of unmodified control plants (FIG. 7A).

Example 6—Creation of Short Stature Corn

Figure 8:
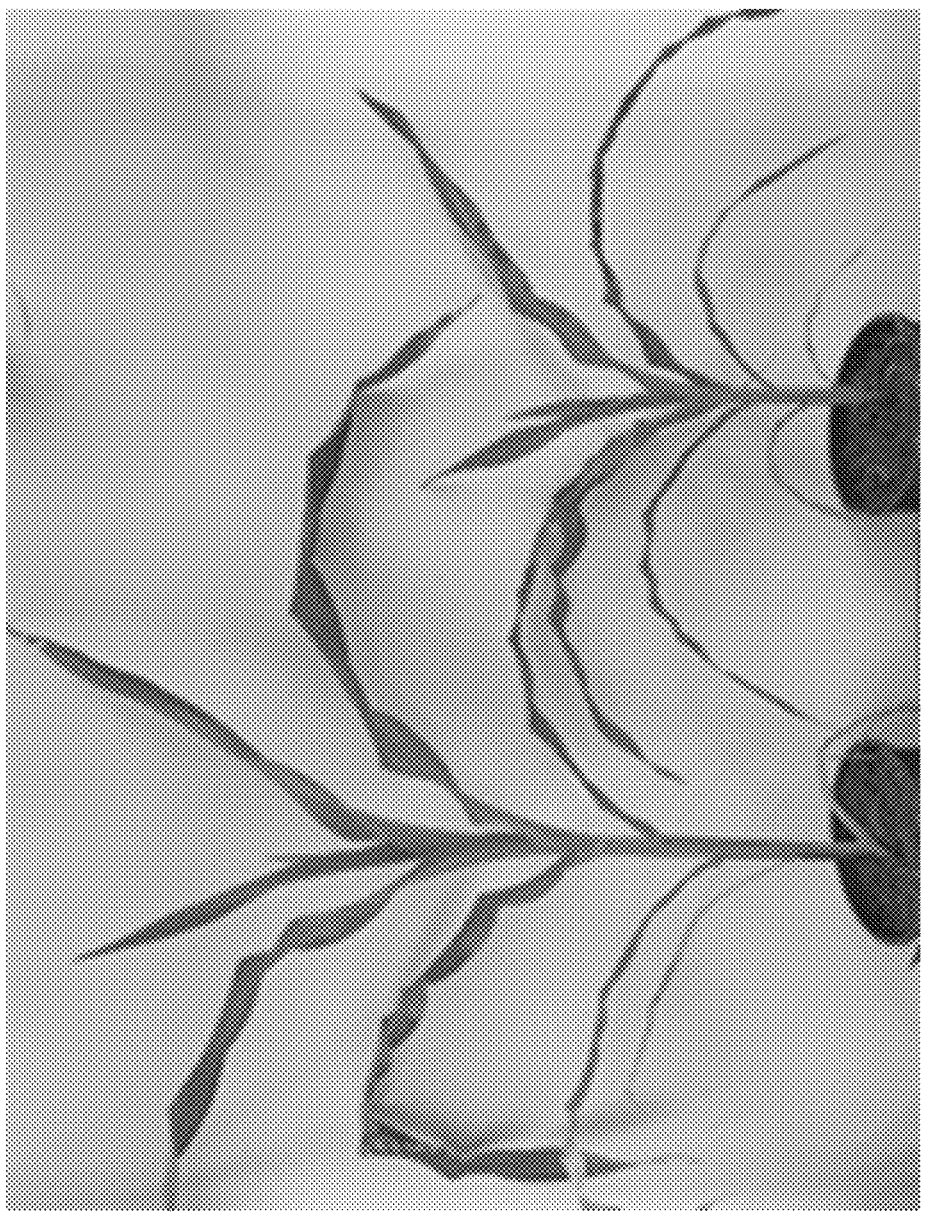
FIG. 8 depicts the result of silencing BWF1 and BR2 genes in maize. Treatment with CATS oligonucleotides targeting BWF1 and BR2 results in shorter maize plants compared to an untreated control plant.

CATS oligos were designed to target genes involved in the biosynthesis of brassinosteroids and involved in the gibberellin-brassinosteroid balance (BWF1 and BR2). A total of 180 individual oligos (90 oligo pairs, shown in SEQ ID NOs: 405-584) were applied to maize seeds. Plants grown from contacted seeds were shorter than control plants not contacted with the CATS oligos (FIG. 8).

Example 7—Targeting the Old Gold Gene in a Population of Tomato Plants

Oligo Treatment and Plant Growth Conditions

Oligos were designed to target the microTom genome (~500 bp upstream and downstream of the Old Gold translation start site, shown in SEQ ID NOs: 585-684) with non-overlapping oligos across this ~1 kb region. Complementary oligos were annealed by incubating at 95° C. for 10 mins with gradual cooling to room temperature, then annealed oligo pairs were pooled for each treatment. Seeds were incubated with 900 ul of oligos at 250 μM concentration (0.5×TE buffer) either targeting Old Gold (treated) or with random oligos as a control (untreated). Seeds were incubated at room temperature in the dark for 3 days before planting in Sunshine Mix soil #4 and grown under 16 hr photoperiods until two true leaves had established (~2 weeks). 50-100 mg of true leaf tissue was harvested from each sample that emerged and frozen in liquid nitrogen before being stored at −80 for later analysis.

RNA Isolation

Total RNA isolation from the starting material was collected using the PureLink Pro 96 total RNA Purification Kit (ThermoFisher Scientific) according to the manufacturer's instructions. Total RNA was eluted in RNase free water. Samples with tissue that were unable to be isolated were discarded. Total RNA was quantified using the Quant-iT™ RNA Assay Kit, broad range, (ThermoFisher Scientific) using fluorescence on the SpectraMax iD3 plate reader. Quantified total RNA was diluted to 1 ng using RNase free water. RNA lower than 1 ng/uL were discarded. After isolation and quantification were complete, there were population sizes of 40 samples of 1 KB treatment; 45 samples of 2.5 KB; 44 samples of RO (random oligonucleotides) control; and 11 samples of Water control.

Quantitative Real-Time PCR Conditions

RT-qPCR was carried out in a 96-well optical plate using Quantstudios 6 Flex Real-Time PCR Systems (Applied Biosystems). Reactions were performed using Luna Universal One-Step RT-qPCR Kit, which uses Luna WarmStart Reverse Transcriptase and SYBR Green I (New England Biolabs); 10 μM of each primer; RNase free water; and 1 μL of diluted RNA (1 ng/uL) in a final volume of 20 μL. The following thermal cycling conditions were used for all amplifications (following the Luna Universal One-Step RT-qPCR Kit manual): 55° C. for 10 minutes for reverse transcription, 95° C. for 1 minute for denaturation, 40 amplification cycles of 95° C. for 10 seconds and 60° C. for 1 minute, and a melt curve of various stages of 60-95° C. All samples were prepared in technical triplicates and three non template controls of RNase free water for each qPCR plate.

Data Analysis

Figure 10:
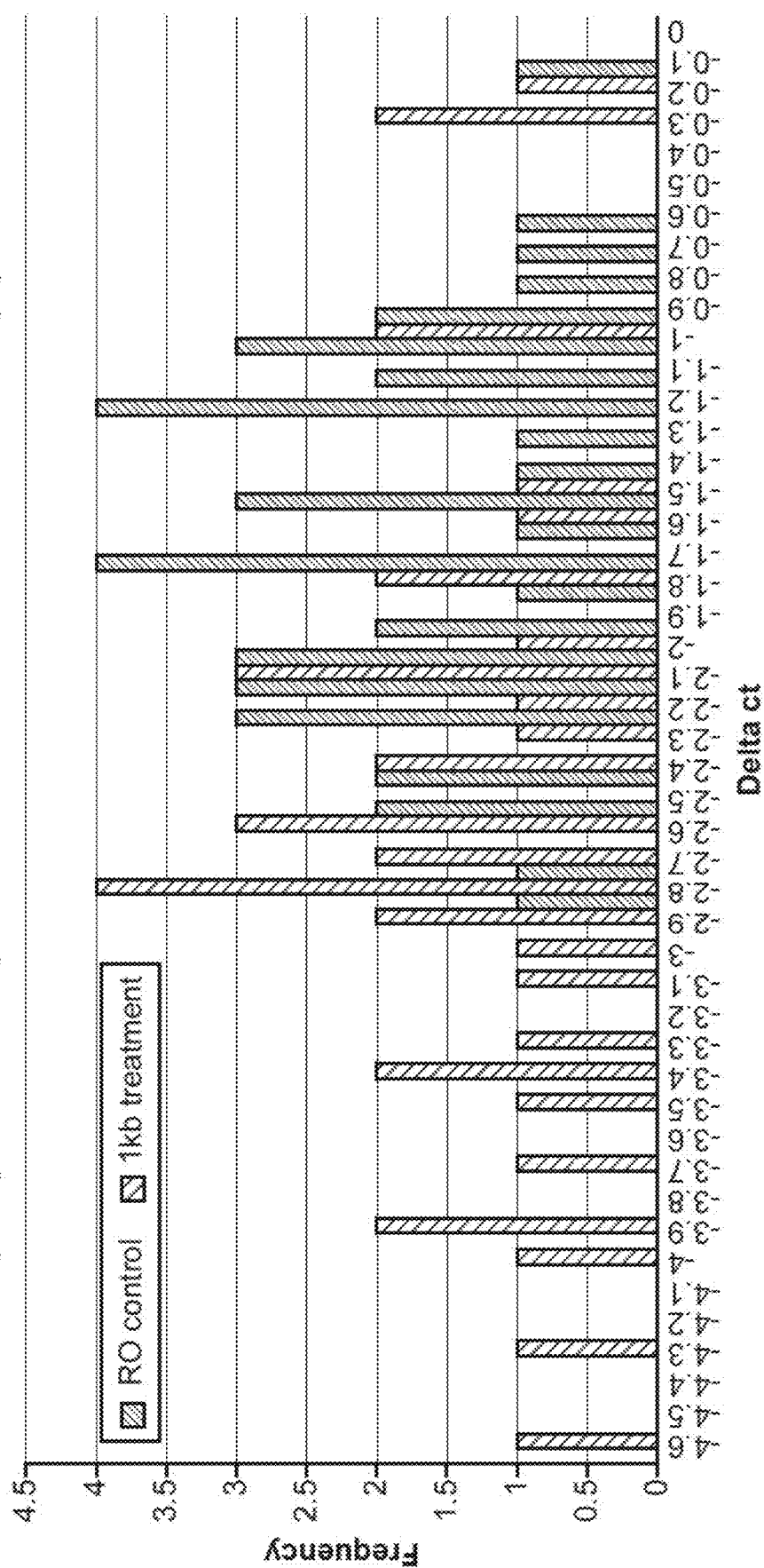
FIG. 10 depicts using CATS oligonucleotides to target the old gold gene in the tomato plant. The 1 kb treatment can decrease the gene expression in individual plants compared to the RO control.

Threshold cycle (Ct) values were averaged from 3 technical replicates of each sample during RT-qPCR and used to calculate the ΔCt value (Old Gold target–GAPDH housekeeping reference). Changes in gene expression for treated (Old Gold) vs untreated (random oligo) populations are displayed as frequency histograms (FIG. 10). ΔCt values for each sample were rounded to 2 d.p. and sorted into groups with a class width of 0.1, ranging from 0 to −4.5 ΔCt (log 2), with more negative ΔCt values indicating greater downregulation of Old Gold target gene compared to GAPDH reference gene.

Example 8—Examples of Sequence Modifications for Oligonucleotides

Figure 9:
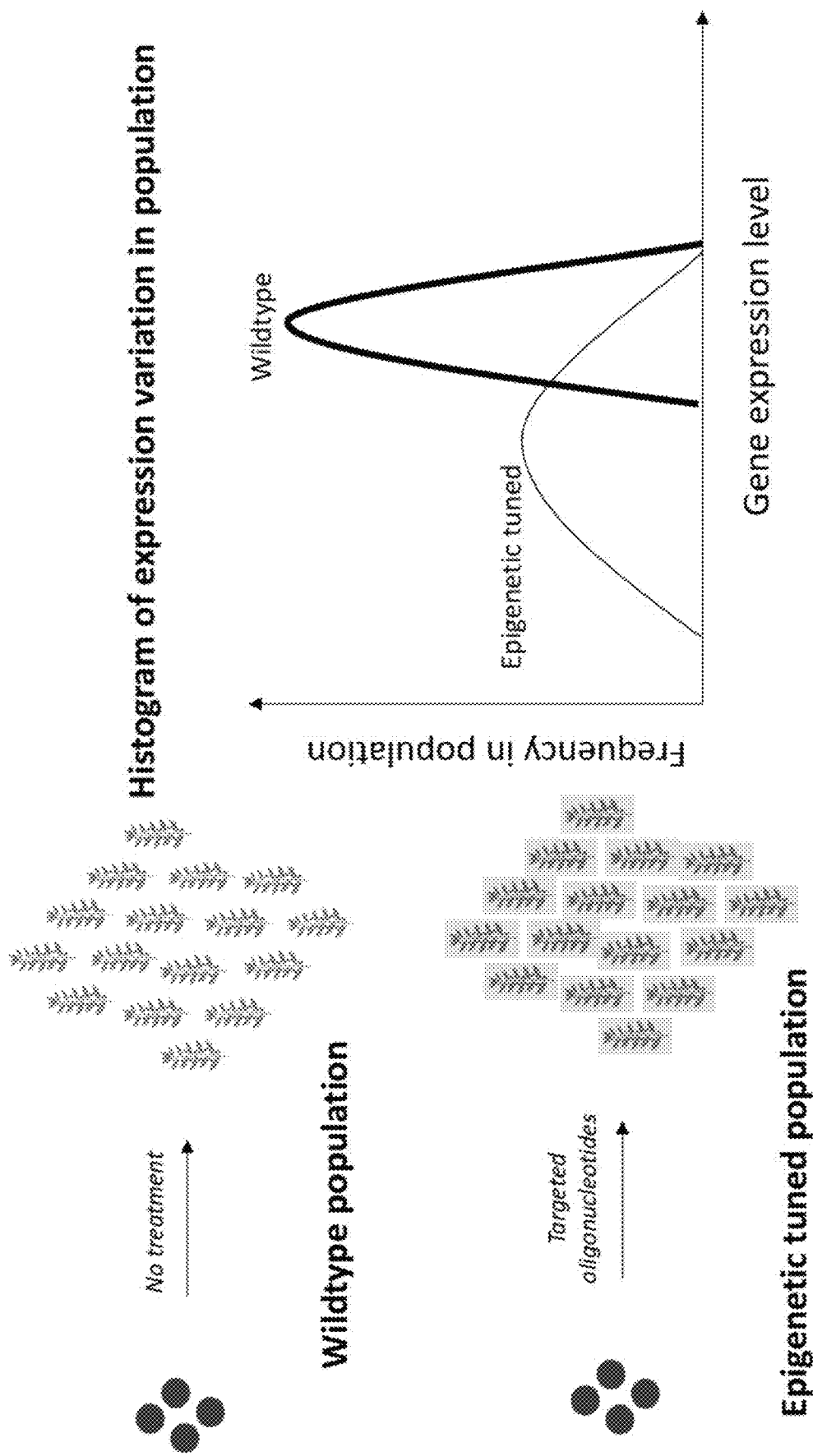
FIG. 9 depicts using epigenetic methods to create variable populations compared to wildtype populations. The population treated with the epigenetic method can have decreased gene expression compared to the wildtype population.

Nucleic acid constructs disclosed herein for example CATs oligonucleotides can have various modifications in individual or multiple locations. These modifications can include but are not limited to phosphorothioate modifications, 2'O-Methyl modifications, 2'Fluoro modifications, or any combination thereof. An example is shown in FIG. 11. An epigenetic modification using constructs herein such as CATs oligonucleotides can create populations with variable gene expression levels (FIG. 9).

| Sequences |
|---|
| CATS oligonucleotide sequences for silencing PDS1 gene (mC = 2'-O-methyl cytosine, mG = 2'-O-methyl guanine, mA = 2'-O-methyl adenine, mT = 2'-O-methylt hymine, mU = 2'-O-methyl uracil) |

| | |
|---|---|
| SEQ ID NO: 1 | TGGCTACTATGTATTGATGTTAAmC |
| SEQ ID NO: 2 | TTAACATCAATACATAGTAGCCAmG |
| SEQ ID NO: 3 | CCATTAAGATGTACTCGCTCTGTmA |
| SEQ ID NO: 4 | ACAGAGCGAGTACATCTTAATGGmA |
| SEQ ID NO: 5 | TAATCATTTTTGTCTGTTATTTTmU |
| SEQ ID NO: 6 | AAAATAACAGACAAAAATGATTAmC |
| SEQ ID NO: 7 | GTCTATATTCAGACAGATGATAAmU |
| SEQ ID NO: 8 | TTATCATCTGTCTGAATATAGACmA |
| SEQ ID NO: 9 | CTAGACACATATACCAAGTAATGmA |
| SEQ ID NO: 10 | CATTACTTGGTATATGTGTCTAGmA |
| SEQ ID NO: 11 | GGATATAGGGAGTATGAACAACTmG |
| SEQ ID NO: 12 | AGTTGTTCATACTCCCTATATCCmU |
| SEQ ID NO: 13 | CAATTAGTTCCGTATTGATAATAmU |
| SEQ ID NO: 14 | TATTATCAATACGGAACTAATTGmU |
| SEQ ID NO: 15 | GGATCGACGTATTTATAATAATAmC |
| SEQ ID NO: 16 | TATTATTATAAATACGTCGATCCmA |
| SEQ ID NO: 17 | TGTTCTATATCTATATTTAATTAmU |
| SEQ ID NO: 18 | TAATTAAATATAGATATAGAACAmG |
| SEQ ID NO: 19 | GCGGAGGTCTCCACTCTTCTCTCmU |
| SEQ ID NO: 20 | GAGAGAAGAGTGGAGACCTCCGCmA |
| SEQ ID NO: 21 | CCATCTTATCATCGCCCACGTACmA |
| SEQ ID NO: 22 | GTACGTGGGCGATGATAAGATGGmA |
| SEQ ID NO: 23 | CCCAATTCCTCGCAACTGGGCTCmC |
| SEQ ID NO: 24 | GAGCCCAGTTGCGAGGAATTGGGmU |
| SEQ ID NO: 25 | CGCCTCCACGACACTGCCCCCCGmC |
| SEQ ID NO: 26 | CGGGGGGCAGTGTCGTGGAGGCGmG |
| SEQ ID NO: 27 | CAAGTCCGCCGCCTCCATTCTTCmA |
| SEQ ID NO: 28 | GAAGAATGGAGGCGGCGGACTTGmA |
| SEQ ID NO: 29 | GTGCGTTGGTGGGTCTGAAACAATmA |
| SEQ ID NO: 30 | ATTGTTTCAGACCCACCAACGCACmA |
| SEQ ID NO: 31 | GTCTCAAAAGGAGGTGAGCTGGGmA |
| SEQ ID NO: 32 | CCCAGCTCACCTCCTTTTGAGACmG |
| SEQ ID NO: 33 | TTTAGCCGACTAATTTTAGATGAmG |

| Sequences | |
|---|---|
| SEQ ID NO: 34 | TCATCTAAAATTAGTCGGCTAAAmU |
| SEQ ID NO: 35 | TAATCTTTAGTTCCGTGCCCCGmC |
| SEQ ID NO: 36 | CGGGGGCACGGAACTAAAGATTAmU |
| SEQ ID NO: 37 | TGCAGGCTCACCCCGACGTGCCCmC |
| SEQ ID NO: 38 | GGGCACGTCGGGGTGAGCCTGCAmC |
| SEQ ID NO: 39 | GCCCTCCGCGCGCGATGCCCCCAmU |
| SEQ ID NO: 40 | TGGGGGCATCGCGCGCGGAGGGCmA |
| SEQ ID NO: 41 | CACCGACGCAGAGCTCGCCCATGmC |
| SEQ ID NO: 42 | CATGGGCGAGCTCTGCGTCGGTGmU |
| SEQ ID NO: 43 | CACGTGCCCCGGCGGCGTCGCGAmU |
| SEQ ID NO: 44 | TCGCGACGCCGCCGGGGCACGTGmC |
| SEQ ID NO: 45 | TATCCCCGCCGTCGCGCGCCTACmG |
| SEQ ID NO: 46 | GTAGGCGCGCGACGGCGGGGATAmC |
| SEQ ID NO: 47 | GTACCTGGAGCAGAAGCGATTTCmG |
| SEQ ID NO: 48 | GAAATCGCTTCTGCTCCAGGTACmA |
| SEQ ID NO: 49 | TGCCGAGGAGCTCACCGCTGTGAmA |
| SEQ ID NO: 50 | TCACAGCGGTGAGCTCCTCGGCAmA |
| SEQ ID NO: 51 | TAGTCCCGTCCCCTCCAGGTCCTmG |
| SEQ ID NO: 52 | AGGACCTGGAGGGGACGGGACTAmA |
| SEQ ID NO: 53 | AATTCACTTGTGTATTCCCCCGAmA |
| SEQ ID NO: 54 | TCGGGGAATACACAAGTGAATTmG |
| SEQ ID NO: 55 | GAGACAGTCTGCACGGCTCCTATmC |
| SEQ ID NO: 56 | ATAGGAGCCGTGCAGACTGTCTCmG |
| SEQ ID NO: 57 | GCATGTACCCAATACCCTGTTTTmG |
| SEQ ID NO: 58 | AAAACAGGGTATTGGGTACATGCmU |
| SEQ ID NO: 59 | TGACCTTGGGTACTATTATAGCAmC |
| SEQ ID NO: 60 | TGCTATAATAGTACCCAAGGTCAmA |
| SEQ ID NO: 61 | TTTCAGTTCGAGTGTTAGACCCTmG |
| SEQ ID NO: 62 | AGGGTCTAACACTCGAACTGAAAmC |
| CATS oligonucleotide sequences for silencing LZY1 gene (mC = 2'-O-methyl cytosine, mG = 2'-O-methyl guanine, mA = 2'-O-methyl adenine, mT = 2'-O-methyl thymine, mU = 2'-O-methyl uracil) | |
| SEQ ID NO: 63 | CTTTTTGGAATTCTTCTGACCAGmG |
| SEQ ID NO: 64 | CTGGTCAGAAGAATTCCAAAAAGmA |
| SEQ ID NO: 65 | CAAGAAAATTAAGGATATATAGCmG |
| SEQ ID NO: 66 | GCTATATATCCTTAATTTTCTTGmG |
| SEQ ID NO: 67 | TAAGGCATGTCGATAATAAAGACmU |
| SEQ ID NO: 68 | GTCTTTATTATCGACATGCCTTAmG |
| SEQ ID NO: 69 | ATAGGACCGAGCAACTCGGATTCmG |
| SEQ ID NO: 70 | GAATCCGAGTTGCTCGGTCCTATmU |
| SEQ ID NO: 71 | GACTCGGACTTGGACTGTGCAACmU |
| SEQ ID NO: 72 | GTTGCACAGTCCAAGTCCGAGTCmA |
| SEQ ID NO: 73 | AGCCGGGATACTCAAAATCGAAAmU |
| SEQ ID NO: 74 | TTTCGATTTTGAGTATCCCGGCTmG |
| SEQ ID NO: 75 | ACTCGGTCCATAGGTTAATACTCmA |
| SEQ ID NO: 76 | GAGTATTAACCTATGGACCGAGTmC |
| SEQ ID NO: 77 | TCATATTTTACATCTAAACGTTCmG |
| SEQ ID NO: 78 | GAACGTTTAGATGTAAAATATGAmG |
| SEQ ID NO: 79 | TGGAAGCAAACACCCCCTTAGACmG |
| SEQ ID NO: 80 | GTCTAAGGGGTGTTTGCTTCCAmC |
| SEQ ID NO: 81 | CCACCTCTTGTCGACCATTTGTAmG |
| SEQ ID NO: 82 | TACAAATGGTCGACAAGAGGTGGmU |
| SEQ ID NO: 83 | CATGTTCCGTTCTGCCGACTGATmG |
| SEQ ID NO: 84 | ATCAGTCGGCAGAACGGAACATGmA |
| SEQ ID NO: 85 | CCTGCAGCTGCAGCTGCAGTGCGmU |
| SEQ ID NO: 86 | CGCACTGCAGCTGCAGCTGCAGGmA |
| SEQ ID NO: 87 | ACTCCATCGTCTATTAATGGCTCmG |
| SEQ ID NO: 88 | GAGCCATTAATAGACGATGGAGTmA |
| SEQ ID NO: 89 | CCAGCGCTCGGCTTAGACAAGCCmU |
| SEQ ID NO: 90 | GGCTTGTCTAAGCCGAGCGCTGGmA |
| SEQ ID NO: 91 | ATGAAGGTCAGTCAGTAGTCCCAmC |
| SEQ ID NO: 92 | TGGGACTACTGACTGACCTTCATmG |
| SEQ ID NO: 93 | AGCTTTTAGTCTAGCTCGACAGTmC |
| SEQ ID NO: 94 | ACTGTCGAGCTAGACTAAAAGCTmG |
| SEQ ID NO: 95 | TTCTTTCTAATCCACCTATTTTCmU |
| SEQ ID NO: 96 | GAAAATAGGTGGATTAGAAAGAAmC |
| SEQ ID NO: 97 | GCGACTCACTCTCGTAGTTGGTGmU |
| SEQ ID NO: 98 | CACCAACTACGAGAGTGAGTCGCmC |
| SEQ ID NO: 99 | TCATGACCTCCTCCTCAAGCTCGmG |
| SEQ ID NO: 100 | CGAGCTTGAGGAGGAGGTCATGAmA |
| SEQ ID NO: 101 | CTCATATTTGAAGCCTCCTTGTTmC |
| SEQ ID NO: 102 | AACAAGGAGGCTTCAAATATGAGmA |
| SEQ ID NO: 103 | AGAAAGCATCGACCTTAGCAAGGmU |
| SEQ ID NO: 104 | CCTTGCTAAGGTCGATGCTTTCTmU |
| SEQ ID NO: 105 | TTGTCCATGCGCTTGGTGAGGTCmG |
| SEQ ID NO: 106 | GACCTCACCAAGCGCATGGACAAmG |
| SEQ ID NO: 107 | AATCTAACCTTTGAGTACCAAATmG |

| SEQ ID NO: | Sequences |
|---|---|
| SEQ ID NO: 108 | ATTTGGTACTCAAAGGTTAGATTmG |
| SEQ ID NO: 109 | TGGAGACACATACACAGAGAAGAmA |
| SEQ ID NO: 110 | TCTTCTCTGTGTATGTGTCTCCAmU |
| SEQ ID NO: 111 | CTTGTTTGGATTGAAACCATTACmA |
| SEQ ID NO: 112 | GTAATGGTTTCAATCCAAACAAGmA |
| SEQ ID NO: 113 | ATATATTGGACTTGTATTCCAAGmC |
| SEQ ID NO: 114 | CTTGGAATACAAGTCCAATATATmA |
| SEQ ID NO: 115 | GTCCTTATAGATTTGGACACTTAmU |
| SEQ ID NO: 116 | TAAGTGTCCAAATCTATAAGGACmU |
| SEQ ID NO: 117 | CAAATCTTCTTGCCTAAGCAAATmU |
| SEQ ID NO: 118 | ATTTGCTTAGGCAAGAAGATTTGmU |
| SEQ ID NO: 119 | CTAAACTCTATTTTATACTCCCTmC |
| SEQ ID NO: 120 | AGGGAGTATAAAATAGAGTTTAGmU |
| SEQ ID NO: 121 | AGTGTTCATTTTGGCTCCTCATTmU |
| SEQ ID NO: 122 | AATGAGGAGCCAAAATGAACACTmA |
| SEQ ID NO: 123 | TCAGATGGATGAAAATGAATCAmG |
| SEQ ID NO: 124 | TAGATTCATTTTCATCCATCTGAmA |
| SEQ ID NO: 125 | TGAATCCACTGATATGTTAAAACmG |
| SEQ ID NO: 126 | GTTTTAACATATCAGTGGATTCAmU |
| SEQ ID NO: 127 | GGGACGGAGAGAGTATATTCCAmG |
| SEQ ID NO: 128 | TTGGAATATACTCTCTCCGTCCCmA |
| SEQ ID NO: 129 | CTATCTTTGGGTTTTCATCTTTTmU |
| SEQ ID NO: 130 | AAAAGATGAAAACCCAAAGATAGmC |
| SEQ ID NO: 131 | GACCAGGAGGGACTCTATTTATAmU |
| SEQ ID NO: 132 | TATAAATAGAGTCCCTCCTGGTCmA |
| SEQ ID NO: 133 | GATAATAAAGACTCTGACTAATAmG |
| SEQ ID NO: 134 | TATTAGTCAGAGTCTTTATTATCmG |
| SEQ ID NO: 135 | AGACTCTGACTAATAGGACCGAGmC |
| SEQ ID NO: 136 | CTCGGTCCTATTAGTCAGAGTCTmU |
| SEQ ID NO: 137 | ACTAATAGGACCGAGCAACTCGGmA |
| SEQ ID NO: 138 | CCGAGTTGCTCGGTCCTATTAGTmC |
| SEQ ID NO: 139 | GACCGAGCAACTCGGATTCGGTGmG |
| SEQ ID NO: 140 | CACCGAATCCGAGTTGCTCGGTCmC |
| SEQ ID NO: 141 | AACTCGGATTCGGTGGAGTGACTmC |
| SEQ ID NO: 142 | AGTCACTCCACCGAATCCGAGTTmG |
| SEQ ID NO: 143 | TTCGGTGGAGTGACTCGGACTTGmG |
| SEQ ID NO: 144 | CAAGTCCGAGTCACTCCACCGAAmU |
| SEQ ID NO: 145 | AGTGACTCGGACTTGGACTGTGCmA |
| SEQ ID NO: 146 | GCACAGTCCAAGTCCGAGTCACTmC |
| SEQ ID NO: 147 | GGACTTGGACTGTGCAACTCGGAmU |
| SEQ ID NO: 148 | TCCGAGTTGCACAGTCCAAGTCCmG |
| SEQ ID NO: 149 | ACTGTGCAACTCGGATTCAGCCGmG |
| SEQ ID NO: 150 | CGGCTGAATCCGAGTTGCACAGTmC |
| SEQ ID NO: 151 | ACTCGGATTCAGCCGGGATACTCmA |
| SEQ ID NO: 152 | GAGTATCCCGGCTGAATCCGAGTmU |
| SEQ ID NO: 153 | TCAGCCGGGATACTCAAAATCGAmA |
| SEQ ID NO: 154 | TCGATTTTGAGTATCCCGGCTGAmA |
| SEQ ID NO: 155 | GATACTCAAAATCGAAATCCAAGmG |
| SEQ ID NO: 156 | CTTGGATTTCGATTTTGAGTATCmC |
| SEQ ID NO: 157 | AAATCGAAATCCAAGGGACTCGGmU |
| SEQ ID NO: 158 | CCGAGTCCCTTGGATTTCGATTTmU |
| SEQ ID NO: 159 | ATCCAAGGGACTCGGTCCATAGGmU |
| SEQ ID NO: 160 | CCTATGGACCGAGTCCCTTGGATmU |
| SEQ ID NO: 161 | GACTCGGTCCATAGGTTAATACTmC |
| SEQ ID NO: 162 | AGTATTAACCTATGGACCGAGTCmC |
| SEQ ID NO: 163 | TCATATTTACATCTAAACGTTCmG |
| SEQ ID NO: 164 | GAACGTTTAGATGTAAAATATGAmG |
| SEQ ID NO: 165 | TACATCTAAACGTTCGATGTGCGmU |
| SEQ ID NO: 166 | CGCACATCGAACGTTTAGATGTAmA |
| SEQ ID NO: 167 | AACGTTCGATGTGCGTGGAAGCAmA |
| SEQ ID NO: 168 | TGCTTCCACGCACATCGAACGTTmU |
| SEQ ID NO: 169 | ATGTGCGTGGAAGCAAACACCCCmC |
| SEQ ID NO: 170 | GGGGTGTTTGCTTCCACGCACATmC |
| SEQ ID NO: 171 | GGAAGCAAACACCCCCTTAGACGmU |
| SEQ ID NO: 172 | CGTCTAAGGGGTGTTTGCTTCCAmA |
| SEQ ID NO: 173 | ACACCCCCTTAGACGTGGGACACmC |
| SEQ ID NO: 174 | GTGTCCCACGTCTAAGGGGTGTmU |
| SEQ ID NO: 175 | TTAGACGTGGGACACCACCTCTTmG |
| SEQ ID NO: 176 | AAGAGGTGGTGTCCCACGTCTAAmG |
| SEQ ID NO: 177 | GGGACACCACCTCTTGTCGACCAmU |
| SEQ ID NO: 178 | TGGTCGACAAGAGGTGGTGTCCCmA |
| SEQ ID NO: 179 | ACCTCTTGTCGACCATTTGTAGCmC |
| SEQ ID NO: 180 | GCTACAAATGGTCGACAAGAGGTmG |
| SEQ ID NO: 181 | TCGACCATTTGTAGCCTTCTTCAmU |
| SEQ ID NO: 182 | TGAAGAAGGCTACAAATGGTCGAmC |
| SEQ ID NO: 183 | TTGTAGCCTTCTTCATGTTCCGTmU |
| SEQ ID NO: 184 | ACGGAACATGAAGAAGGCTACAAmA |

| | Sequences |
|---|---|
| SEQ ID NO: 185 | TTCTTCATGTTCCGTTCTGCCGAmC |
| SEQ ID NO: 186 | TCGGCAGAACGGAACATGAAGAAmG |
| SEQ ID NO: 187 | GTTCCGTTCTGCCGACTGATGGAmU |
| SEQ ID NO: 188 | TCCATCAGTCGGCAGAACGGAACmA |
| SEQ ID NO: 189 | CTGCCGACTGATGGATCACTCCTmG |
| SEQ ID NO: 190 | AGGAGTGATCCATCAGTCGGCAGmA |
| SEQ ID NO: 191 | TGATGGATCACTCCTGCAGCTGCmA |
| SEQ ID NO: 192 | GCAGCTGCAGGAGTGATCCATCAmG |
| SEQ ID NO: 193 | CACTCCTGCAGCTGCAGCTGCAGmU |
| SEQ ID NO: 194 | CTGCAGCTGCAGCTGCAGGAGTGmA |

CATS oligonucleotide sequences for silencing PPO gene (mC = 2'-O-methyl cytosine, mG = 2'-O-methyl guanine, mA = 2'-O-methyl adenine, mT = 2'-O-methyl thymine, mU = 2'-O-methyl uracil)

| | Sequences |
|---|---|
| SEQ ID NO: 195 | ATGAAGCAAAACTCTAAAGTTGAmC |
| SEQ ID NO: 196 | TCAACTTTAGAGTTTTGCTTCATmA |
| SEQ ID NO: 197 | AACCCAGTTTTTCAGCTCTCACTmA |
| SEQ ID NO: 198 | AGTGAGAGCTGAAAAACTGGGTTmG |
| SEQ ID NO: 199 | ATTACCAATTGATCATCATCTTGmC |
| SEQ ID NO: 200 | CAAGATGATGATCAATTGGTAATmU |
| SEQ ID NO: 201 | ATTACAACTTTCCAGCTATTTTGmC |
| SEQ ID NO: 202 | CAAAATAGCTGGAAAGTTGTAATmA |
| SEQ ID NO: 203 | CACTTTATAATCCTAATCCTACmC |
| SEQ ID NO: 204 | TGTAGGATTAGGATTATAAAGTGmU |
| SEQ ID NO: 205 | AAGCTCATTCAACAACACAATTAmG |
| SEQ ID NO: 206 | TAATTGTGTTGTTGAATGAGCTTmU |
| SEQ ID NO: 207 | TCAAACACAAAATAGAGTTATGGmC |
| SEQ ID NO: 208 | CCATAACTCTATTTTGTGTTTGAmU |
| SEQ ID NO: 209 | TTAACTTCATGTACTACCATTTCmC |
| SEQ ID NO: 210 | GAAATGGTAGTACATGAAGTTAAmA |
| SEQ ID NO: 211 | CATCCAAAATTTTCGTCCGTCCAmA |
| SEQ ID NO: 212 | TGGACGGACGAAAATTTTGGATGmG |
| SEQ ID NO: 213 | CGATAACTTAAGGTGAATTGTGmA |
| SEQ ID NO: 214 | CACAATTCACCTTAAAGTTATCGmA |
| SEQ ID NO: 215 | TAATGAAGGAAAATCTTTTCCAGmG |
| SEQ ID NO: 216 | CTGGAAAAGATTTTCCTTCATTAmU |
| SEQ ID NO: 217 | GATAGACGAAATGTCCTCCTTGGmU |
| SEQ ID NO: 218 | CCAAGGAGGACATTTCGTCTATCmA |
| SEQ ID NO: 219 | GGCTCTATGGAGCATCTAATCTTmA |
| SEQ ID NO: 220 | AAGATTAGATGCTCCATAGAGCCmC |
| SEQ ID NO: 221 | AACCAACGAGCCATTTGCCCTAGmG |
| SEQ ID NO: 222 | CTAGGGCAAATGGCTCGTTGGTTmA |
| SEQ ID NO: 223 | GTACCACCCCAGACTTCTCAACmA |
| SEQ ID NO: 224 | GTTGAGAAGTCTGGGGGTGGTACmC |
| SEQ ID NO: 225 | TCTGTCAACCGACCCAACCGACCmC |
| SEQ ID NO: 226 | GGTCGGTTGGGTCGGTTGACAGAmA |
| SEQ ID NO: 227 | TCCAGACTGTAAGTTATTTTCTmG |
| SEQ ID NO: 228 | AGAAAAATAACTTACAGTCTGGAmU |
| SEQ ID NO: 229 | CAGAGCTTCTAAGAACAAAAACTmU |
| SEQ ID NO: 230 | AGTTTTGTTCTTAGAAGCTCTGmU |
| SEQ ID NO: 231 | GTATGGCTGCTATACAAAATTCCmC |
| SEQ ID NO: 232 | GGAATTTTGTATAGCAGCCATACmA |
| SEQ ID NO: 233 | CGCTTCCTGGAATAATTGATATGmG |
| SEQ ID NO: 234 | CATATCAATTATTCCAGGAAGCGmG |
| SEQ ID NO: 235 | TATTATATAAGGCAAGGTATAGCmC |
| SEQ ID NO: 236 | GCTATACCTTGCCTTATATAATAmA |
| SEQ ID NO: 237 | TCATTCAAAACCTAGCAATAATGmG |
| SEQ ID NO: 238 | CATTATTGCTAGGTTTTGAATGAmA |
| SEQ ID NO: 239 | GTAGTAATACATCTCTCAAAACTmC |
| SEQ ID NO: 240 | AGTTTTGAGAGATGTATTACTACmU |
| SEQ ID NO: 241 | TTCTTCCTCCACTTCTTTATCTTmC |
| SEQ ID NO: 242 | AAGATAAAGAAGTGGAGGAAGAAmG |
| SEQ ID NO: 243 | AAGCCCTCTTCAACTTTTCATCCmA |
| SEQ ID NO: 244 | GGATGAAAAGTTGAAGAGGGCTTmA |
| SEQ ID NO: 245 | CGTACCAAATGTTCAAAGTTTCAmU |
| SEQ ID NO: 246 | TGAAACTTTGAACATTTGGTACGmU |
| SEQ ID NO: 247 | TACCAATAATAACGGTGACCAAAmA |
| SEQ ID NO: 248 | TTTGGTCACCGTTATTATTGGTAmA |
| SEQ ID NO: 249 | GTTGAAACGAATTCTGTTGATCGmA |
| SEQ ID NO: 250 | CGATCAACAGAATTCGTTTCAACmG |
| SEQ ID NO: 251 | TTCTTCTTGGCTTAGGTGGTCTTmU |
| SEQ ID NO: 252 | AAGACCACCTAAGCCAAGAAGAAmC |
| SEQ ID NO: 253 | TGCTAATGCTATACCATTAGCTGmC |
| SEQ ID NO: 254 | CAGCTAATGGTATAGCATTAGCAmA |
| SEQ ID NO: 255 | AATTATCAATGCTTGTGAATCTCmG |
| SEQ ID NO: 256 | GAGATTCACAAGCATTGATAATTmU |
| SEQ ID NO: 257 | TGTTAAAAATTTCCTCACCTACmC |
| SEQ ID NO: 258 | GTAGGTGAGGAAATTTTTTAACAmA |

| | Sequences |
|---|---|
| SEQ ID NO: 259 | GAATTGTTCGATATGAGATCGAGmC |
| SEQ ID NO: 260 | CTCGATCTCATATCGAACAATTCmG |
| SEQ ID NO: 261 | TGGAGTAATATTTTATTTGGCTCmC |
| SEQ ID NO: 262 | GAGCCAAATAAAATATTACTCCAmU |
| SEQ ID NO: 263 | TATATAAGGCAATGTATAGCCCTmA |
| SEQ ID NO: 264 | AGGGCTATACATTGCCTTATATAmA |
| SEQ ID NO: 265 | TCATCCAAAAACTAGCAATGGCAmA |
| SEQ ID NO: 266 | TGCCATTGCTAGTTTTTGGATGAmA |
| SEQ ID NO: 267 | TAATAGTAGTAGTACCACTCTCAmA |
| SEQ ID NO: 268 | TGAGAGTGGTACTACTACTATTAmC |
| SEQ ID NO: 269 | TTTACTTCTTCCTCCACTTCTTTmA |
| SEQ ID NO: 270 | AAAGAAGTGGAGGAAGAAGTAAAmA |
| SEQ ID NO: 271 | CTCCTAAGCCCTCTCAACTTTTCmC |
| SEQ ID NO: 272 | GAAAAGTTGAGAGGGCTTAGGAGmU |
| SEQ ID NO: 273 | ACGTAACAAAACGTTCAAAGTTTmC |
| SEQ ID NO: 274 | AAACTTTGAACGTTTTGTTACGTmU |
| SEQ ID NO: 275 | GTTACCAATAATAACGGTGACCAmA |
| SEQ ID NO: 276 | TGGTCACCGTTATTATTGGTAACmC |
| SEQ ID NO: 277 | ACGTTGAAACGAATTCTGTTGATmC |
| SEQ ID NO: 278 | ATCAACAGAATTCGTTTCAACGTmU |
| SEQ ID NO: 279 | TGTTCTTCTTGGTTTAGGAGGTCmU |
| SEQ ID NO: 280 | GACCTCCTAAACCAAGAAGAACAmU |
| SEQ ID NO: 281 | GTTGCTAATGCTATACCATTAGCmU |
| SEQ ID NO: 282 | GCTAATGGTATAGCATTAGCAACmA |
| SEQ ID NO: 283 | CTTCTCCAACTCCACCTCCTGATmC |
| SEQ ID NO: 284 | ATCAGGAGGTGGAGTTGGAGAAGmC |
| SEQ ID NO: 285 | CCAAACAATCTGTTCAGCTATTCmA |
| SEQ ID NO: 286 | GAATAGCTGAACAGATTGTTTGGmU |
| SEQ ID NO: 287 | AAATGTGTAAAAGATTTCCCACAmC |
| SEQ ID NO: 288 | TGTGGGAAATCTTTTACACATTTmU |
| SEQ ID NO: 289 | TCAAAAACCTCCCACCTACCGCGmU |
| SEQ ID NO: 290 | CGCGGTAGGTGGGAGGTTTTTGAmA |
| SEQ ID NO: 291 | TGTTGGAGTGGTAGGTGAGCCTCmU |
| SEQ ID NO: 292 | GAGGCTCACCTACCACTCCAACAmU |
| SEQ ID NO: 293 | AGCAACATACTATATAATGCAAGmG |
| SEQ ID NO: 294 | CTTGCATTATATAGTATGTTGCTmA |
| SEQ ID NO: 295 | TATGAATCTTCATCAACCAAAAGmC |
| SEQ ID NO: 296 | CTTTTGGTTGATGAAGATTCATAmU |
| SEQ ID NO: 297 | AATGGCAAGTGTGTGCAATAGTAmG |
| SEQ ID NO: 298 | TACTATTGCACACACTTGCCATTmG |
| SEQ ID NO: 299 | ACTACAACTCTCAAAACTCCTTTmC |
| SEQ ID NO: 300 | AAAGGAGTTTTGAGAGTTGTAGTmA |
| SEQ ID NO: 301 | CCAATACTTCTTTATCTTCAACTmC |
| SEQ ID NO: 302 | AGTTGAAGATAAAGAAGTATTGGmA |
| SEQ ID NO: 303 | CTCTCAACTTTTCCTCCATGGAAmA |
| SEQ ID NO: 304 | TTCCATGGAGGAAAAGTTGAGAGmG |
| SEQ ID NO: 305 | CAAATGTTCAAAGTTTCATGCAAmG |
| SEQ ID NO: 306 | TTGCATGAAACTTTGAACATTTGmG |
| SEQ ID NO: 307 | ATAATAACGGTGACCAAAACGTTmG |
| SEQ ID NO: 308 | AACGTTTTGGTCACCGTTATTATmU |
| SEQ ID NO: 309 | TTCTGTTGATCGAAGAAATGTTCmU |
| SEQ ID NO: 310 | GAACATTTCTTCGATCAACAGAAmU |
| SEQ ID NO: 311 | TTAGGAGGTCTATATGGTGTTGCmU |
| SEQ ID NO: 312 | GCAACACCATATAGACCTCCTAAmA |
| SEQ ID NO: 313 | TACCATTAGCTGCATCCGCTGCTmC |
| SEQ ID NO: 314 | AGCAGCGGATGCAGCTAATGGTAmU |
| SEQ ID NO: 315 | GATCAAAGGATGGCTAAATTTTTmC |
| SEQ ID NO: 316 | AAAAATTTAGCCATCCTTTGATCmA |
| SEQ ID NO: 317 | TTGAACTTGAGGATCAATATTTCmC |
| SEQ ID NO: 318 | GAAATATTGATCCTCAAGTTCAAmA |
| SEQ ID NO: 319 | GAGAGTGAGTAATTACTCCAAGAmU |
| SEQ ID NO: 320 | TCTTGGAGTAATTACTCACTCTCmU |
| SEQ ID NO: 321 | ACAATTATCACCAACGTGTTACAmC |
| SEQ ID NO: 322 | TGTAACACGTTGGTGATAATTGTmA |
| SEQ ID NO: 323 | GCTACATATACCTTCACCATTTTmG |
| SEQ ID NO: 324 | AAAATGGTGAAGGTATATGTAGCmA |
| SEQ ID NO: 325 | GCAACTCTTCTAACAAAAAATCAmC |
| SEQ ID NO: 326 | TGATTTTTGTTAGAAGAGTTGCmA |
| SEQ ID NO: 327 | AACACAATGTCTTCTTCTAGTACmU |
| SEQ ID NO: 328 | GTACTAGAAGAAGACATTGTGTTmG |
| SEQ ID NO: 329 | TTCCATTATGCACCAACAAATCCmC |
| SEQ ID NO: 330 | GGATTTGTTGGTGCATAATGGAAmG |
| SEQ ID NO: 331 | TTCCTTCACCACCAACAACTCATmC |
| SEQ ID NO: 332 | ATGAGTTGTTGGTGGTGAAGGAAmG |
| SEQ ID NO: 333 | TCAAACCCTCTCAACTTTTCCTmC |
| SEQ ID NO: 334 | AGGAAAAGTTGAGAGGGTTTTGAmU |
| SEQ ID NO: 335 | GACGTAATCAAAGTTTCAAGGTTmU |

| | Sequences |
|---|---|
| SEQ ID NO: 336 | AACCTTGAAACTTTGATTACGTCmU |
| SEQ ID NO: 337 | CGTCAACAATAATGTTGGCGAGCmA |
| SEQ ID NO: 338 | GCTCGCCAACATTATTGTTGACGmU |
| SEQ ID NO: 339 | AACCTTGACGCTGTTGATAGGCGmA |
| SEQ ID NO: 340 | CGCCTATCAACAGCGTCAAGGTTmU |
| SEQ ID NO: 341 | TTTTAGGGTTAGGAGGTCTTTATmG |
| SEQ ID NO: 342 | ATAAAGACCTCCTAACCCTAAAAmG |
| SEQ ID NO: 343 | TAATCTTGCACCATTAGCCTCTGmC |
| SEQ ID NO: 344 | CAGAGGCTAATGGTGCAAGATTAmG |
| SEQ ID NO: 345 | TGCAAAAGAAAATAGGATCTGCAmU |
| SEQ ID NO: 346 | TGCAGATCCTATTTTCTTTTGCAmU |
| SEQ ID NO: 347 | ATACAAAACCATTTCAAAACTGCmG |
| SEQ ID NO: 348 | GCAGTTTTGAAATGGTTTTGTATmU |
| SEQ ID NO: 349 | CGTTTGTACTAGGTACATGAATTmU |
| SEQ ID NO: 350 | AATTCATGTACCTAGTACAAACGmU |
| SEQ ID NO: 351 | AAATACTGATGAAACGCTGCAAAmG |
| SEQ ID NO: 352 | TTTGCAGCGTTTCATCAGTATTTmA |
| SEQ ID NO: 353 | ACTCATCCCAGCAATGGCTTCTTmC |
| SEQ ID NO: 354 | AAGAAGCCATTGCTGGGATGAGTmG |
| SEQ ID NO: 355 | CCTTTGTGCACTACCAATATTCCmC |
| SEQ ID NO: 356 | GGAATATTGGTAGTGCACAAAGGmU |
| SEQ ID NO: 357 | TCTCCAATAATACCAACTCATCTmU |
| SEQ ID NO: 358 | AGATGAGTTGGTATTATTGGAGAmA |
| SEQ ID NO: 359 | AAAACCCTCTCAGCTTTTCCTCCmA |
| SEQ ID NO: 360 | GGAGGAAAAGCTGAGAGGGTTTTmG |
| SEQ ID NO: 361 | CGTAGTCAAAGTTTCAAGGTTTCmA |
| SEQ ID NO: 362 | GAAACCTTGAAACTTTGACTACGmC |
| SEQ ID NO: 363 | ATAGCGAGCATGACAAAAATAACmC |
| SEQ ID NO: 364 | GTTATTTTTGTCATGCTCGCTATmA |
| SEQ ID NO: 365 | CGATGCTGTTGATAGGAGAAATGmU |
| SEQ ID NO: 366 | CATTTCTCCTATCAACAGCATCGmU |
| SEQ ID NO: 367 | GGGTTAGGAGGTCTTTATGGTGCmU |
| SEQ ID NO: 368 | GCACCATAAAGACCTCCTAACCCmU |
| SEQ ID NO: 369 | TTGCACCATTAGCCACTGCTGCTmC |
| SEQ ID NO: 370 | AGCAGCAGTGGCTAATGGTGCAAmG |
| SEQ ID NO: 371 | ACCACCTGATTTGAAAACTTGTAmG |
| SEQ ID NO: 372 | TACAAGTTTTCAAATCAGGTGGTmG |
| SEQ ID NO: 373 | ACTGTAACTCCTGGTGGTCCAGCmA |
| SEQ ID NO: 374 | GCTGGACCACCAGGAGTTACAGTmG |
| SEQ ID NO: 375 | TATGTGCTCACGTGGACACATTAmC |
| SEQ ID NO: 376 | TAATGTGTCCACGTGAGCACATAmG |
| SEQ ID NO: 377 | GATGCAATATTTATGATGTTCACmG |
| SEQ ID NO: 378 | GTGAACATCATAAATATTGCATCmA |
| SEQ ID NO: 379 | ATTATATTCTCGACAAGTTGAACmG |
| SEQ ID NO: 380 | GTTCAACTTGTCGAGAATATAATmU |
| SEQ ID NO: 381 | GGAAATGATGGAGATTATTATGGmU |
| SEQ ID NO: 382 | CCATAATAATCTCCATCATTTCCmA |
| SEQ ID NO: 383 | TCTTCCTCACAAGGTAATTACAAmA |
| SEQ ID NO: 384 | TTGTAATTACCTTGTGAGGAAGAmA |
| SEQ ID NO: 385 | CCTTAGCTTGCTCCATATTATTCmU |
| SEQ ID NO: 386 | GAATAATATGGAGCAAGCTAAGGmA |
| SEQ ID NO: 387 | TGCTAGCCCTAGATGTTCATGAAmU |
| SEQ ID NO: 388 | TTCATGAACATCTAGGGCTAGCAmU |
| SEQ ID NO: 389 | CAAGCAAAAAATGTCTTCCATTmC |
| SEQ ID NO: 390 | AATGGAAGACATTTTTTGCTTGmU |
| SEQ ID NO: 391 | CACTACCAATACTCTCTCTTCTTmC |
| SEQ ID NO: 392 | AAGAAGAGAGAGTATTGGTAGTGmG |
| SEQ ID NO: 393 | ACCACTTTTTCCAACTTGCATTCmU |
| SEQ ID NO: 394 | GAATGCAAGTTGGAAAAAGTGGTmG |
| SEQ ID NO: 395 | GCAAAACATCAAAAATTTCCTCmC |
| SEQ ID NO: 396 | GAGGAAATTTTTGATGTTTTGCmA |
| SEQ ID NO: 397 | AGCATAATGTCCATCGTAATTTCmC |
| SEQ ID NO: 398 | GAAATTACGATGGACATTATGCTmU |
| SEQ ID NO: 399 | GCAAACCATAGATGATAATAGTmC |
| SEQ ID NO: 400 | ACTATTATCATCTATGGTTTTGCmA |
| SEQ ID NO: 401 | CAATAACTCACCCATCGACATTTmC |
| SEQ ID NO: 402 | AAATGTCGATGGGTGAGTTATTGmU |
| SEQ ID NO: 403 | ACAATATGATCGATAGAAGAAACmG |
| SEQ ID NO: 404 | GTTTCTTCTATCGATCATATTGTmU |
| CATS oligonucleotide sequences for silencing DWF1 and BR2 genes (mC = 2'-O-methyl cytosine, mG = 2'-O-methyl guanine, mA = 2'-O-methyl adenine, mT = 2'-O-methyl thymine, mU = 2'-O-methyl uracil) | |
| SEQ ID NO: 405 | TCGGCCTGCCGAGCCTAGACAATmA |
| SEQ ID NO: 406 | ATTGTCTAGGCTCGGCAGGCCGAmC |
| SEQ ID NO: 407 | TCTCCTCTCGATGGGGTCTCTCCmC |
| SEQ ID NO: 408 | GGAGAGACCCCATCGAGAGGAGAmG |
| SEQ ID NO: 409 | ATCCAGGCGCCGCCGGTGACCTTmC |

| Sequences | |
|---|---|
| SEQ ID NO: 410 | AAGGTCACCGGCGGCGCCTGGATmC |
| SEQ ID NO: 411 | GCGCACGCGCGGATCATTCGTCCmC |
| SEQ ID NO: 412 | GGACGAATGATCCGCGCGTGCGCmA |
| SEQ ID NO: 413 | ACAGTCTGACACGTTAGATAGAGmA |
| SEQ ID NO: 414 | CTCTATCTAACGTGTCAGACTGTmC |
| SEQ ID NO: 415 | ATGCGCCAGGTCGTGGACCGTCCmC |
| SEQ ID NO: 416 | GGACGGTCCACGACCTGGCGCATmG |
| SEQ ID NO: 417 | AGAGAACACTGCCGTCGGTTTTTmA |
| SEQ ID NO: 418 | AAAAACCGACGGCAGTGTTCTCTmG |
| SEQ ID NO: 419 | TTGACGTTCGAAAAGATGTCAACmA |
| SEQ ID NO: 420 | GTTGACATCTTTTCGAACGTCAAmU |
| SEQ ID NO: 421 | AGTTTTTTTATACAACTGAGAGAmG |
| SEQ ID NO: 422 | TCTCTCAGTTGTATAAAAAACTmC |
| SEQ ID NO: 423 | GAGTGAGTTAAATGGCAACAAACmA |
| SEQ ID NO: 424 | GTTTGTTGCCATTTAACTCACTCmG |
| SEQ ID NO: 425 | GGAAAAAAACTATGAGATGTCATmC |
| SEQ ID NO: 426 | ATGACATCTCATAGTTTTTTTCCmU |
| SEQ ID NO: 427 | ATGACGGTAAATAAATATGGATGmG |
| SEQ ID NO: 428 | CATCCATATTTATTTACCGTCATmA |
| SEQ ID NO: 429 | CTAAAACGAAAAGTGGCAAAACCmU |
| SEQ ID NO: 430 | GGTTTTGCCACTTTTCGTTTTAGmU |
| SEQ ID NO: 431 | GACGGGTGTCGCCGAGTGCAGCCmG |
| SEQ ID NO: 432 | GGCTGCACTCGGCGACACCCGTCmC |
| SEQ ID NO: 433 | ACCCCCACCGATGTCCTGAGATTmG |
| SEQ ID NO: 434 | AATCTCAGGACATCGGTGGGGGTmU |
| SEQ ID NO: 435 | AAGCCGCAGGCAGCATCTGCATCmU |
| SEQ ID NO: 436 | GATGCAGATGCTGCCTGCGGCTTmC |
| SEQ ID NO: 437 | CTCCGCTCCGCCTACTGCTGCTGmG |
| SEQ ID NO: 438 | CAGCAGCAGTAGGCGGAGCGGAGmG |
| SEQ ID NO: 439 | GGCGGAGAAGGAGGCCCTTGCGCmC |
| SEQ ID NO: 440 | GCGCAAGGGCCTCCTTCTCCGCCmU |
| SEQ ID NO: 441 | GCCGGATCAGAGCCGGTAAGACCmA |
| SEQ ID NO: 442 | GGTCTTACCGGCTCTGATCCGGCmC |
| SEQ ID NO: 443 | CGCTCCTCCTCGCTGGTTGCTTTmC |
| SEQ ID NO: 444 | AAAGCAACCAGCGAGGAGGAGCGmU |
| SEQ ID NO: 445 | CGCCGGTATTCCCAGTCCGTGTGmC |
| SEQ ID NO: 446 | CACACGGACTGGGAATACCGGCGmG |
| SEQ ID NO: 447 | GTCTGCTCCCGTCGCTGCCTAGAmU |
| SEQ ID NO: 448 | TCTAGGCAGCGACGGGAGCAGACmA |
| SEQ ID NO: 449 | GGATCTTTCGTGCATGGCGGCAGmA |
| SEQ ID NO: 450 | CTGCCGCCATGCACGAAAGATCCmU |
| SEQ ID NO: 451 | CCCCCCCCCCCCCCCCCCCCCCCmC |
| SEQ ID NO: 452 | GGGGGGGGGGGGGGGGGGGGGGGmG |
| SEQ ID NO: 453 | CGTGTATACGAGTTTTCTCTAGGmC |
| SEQ ID NO: 454 | CCTAGAGAAAACTCGTATACACGmG |
| SEQ ID NO: 455 | CATGTTGGATTGGATTGCGCTAGmU |
| SEQ ID NO: 456 | CTAGCGCAATCCAATCCAACATGmC |
| SEQ ID NO: 457 | GAGGTGCCGGCCGTACCCATCCTmC |
| SEQ ID NO: 458 | AGGATGGGTACGGCCGGCACCTCmU |
| SEQ ID NO: 459 | AGAAAAAGGCCCAGTCATTTTTmG |
| SEQ ID NO: 460 | AAAAATGACTGGGCCTTTTTCTmG |
| SEQ ID NO: 461 | ATTTATTTTACAGCTGCCACATmG |
| SEQ ID NO: 462 | ATGTGGCAGCTGTAAAAATAAATmA |
| SEQ ID NO: 463 | TTTTTGTTGGGGTTTTACTACTAmC |
| SEQ ID NO: 464 | TAGTAGTAAAACCCCAACAAAAAmC |
| SEQ ID NO: 465 | AACTGTTTTGTCAAATACTGTAAmC |
| SEQ ID NO: 466 | TTACAGTATTTGACAAAACAGTTmC |
| SEQ ID NO: 467 | AAAGCTGTTTGTAGGAGTGAAGCmU |
| SEQ ID NO: 468 | GCTTCACTCCTACAAACAGCTTTmA |
| SEQ ID NO: 469 | AAACAGAACTTCATATTGTTCCAmG |
| SEQ ID NO: 470 | TGGAACAATATGAAGTTCTGTTTmA |
| SEQ ID NO: 471 | TTCCAACAAAAAAATTGCAATTCmG |
| SEQ ID NO: 472 | GAATTGCAATTTTTTTGTTGGAAmC |
| SEQ ID NO: 473 | GCTACCAGTACAGCGCTAGATGGmA |
| SEQ ID NO: 474 | CCATCTAGCGCTGTACTGGTAGCmC |
| SEQ ID NO: 475 | CGAACATGAAACGTTTACTTTTTmC |
| SEQ ID NO: 476 | AAAAAGTAAACGTTTCATGTTCGmC |
| SEQ ID NO: 477 | TGTTTGATGGATCACATTTATCTmC |
| SEQ ID NO: 478 | AGATAAATGTGATCCATCAAACAmU |
| SEQ ID NO: 479 | TGTTGGATACCGGTACTTTTTACmG |
| SEQ ID NO: 480 | GTAAAAGTACCGGTATCCAACAmC |
| SEQ ID NO: 481 | GTACAGGGGCCACTGGCTATATAmU |
| SEQ ID NO: 482 | TATATAGCCAGTGGCCCCTGTACmA |
| SEQ ID NO: 483 | CACTCCATTAATTTCCAGGGATGmC |
| SEQ ID NO: 484 | CATCCCTGGAAATTAATGGAGTGmA |
| SEQ ID NO: 485 | CTCTCTCTGCTACATACATCCATmU |
| SEQ ID NO: 486 | ATGGATGTATGTAGCAGAGAGAGmA |

| | |
|---|---|
| SEQ ID NO: 487 | TTTTTTGTGGAATTTTGCACTTGmG |
| SEQ ID NO: 488 | CAAGTGCAAAATTCCACAAAAAmA |
| SEQ ID NO: 489 | TCTCAGTTTAATTTGGAGGATCAmA |
| SEQ ID NO: 490 | TGATCCTCCAAATTAAACTGAGAmA |
| SEQ ID NO: 491 | AGACATACATGGCGGATCCTCTGmG |
| SEQ ID NO: 492 | CAGAGGATCCGCCATGTATGTCTmC |
| SEQ ID NO: 493 | AAGGTCTTAGCGGACTACTTGGTmG |
| SEQ ID NO: 494 | ACCAAGTAGTCCGCTAAGACCTTmC |
| SEQ ID NO: 495 | CTTCGTGGCCCTTCCAATATCTGmC |
| SEQ ID NO: 496 | CAGATATTGGAAGGGCCACGAAGmA |
| SEQ ID NO: 497 | TGGTGAACACGTGGTCCGCCATGmA |
| SEQ ID NO: 498 | CATGGCGGACCACGTGTTCACCAmG |
| SEQ ID NO: 499 | GAACACCAGGAGAACGTAGAGGGmU |
| SEQ ID NO: 500 | CCCTCTACGTTCTCCTGGTGTTCmC |
| SEQ ID NO: 501 | ATCCGAAGAGGGACGGCCTCGTCmU |
| SEQ ID NO: 502 | GACGAGGCCGTCCCTCTTCGGATmC |
| SEQ ID NO: 503 | GTCGTGGGCATGCGCAACGTGGAmC |
| SEQ ID NO: 504 | TCCACGTTGCGCATGCCCACGACmC |
| SEQ ID NO: 505 | GGTCGACCTCTCCGCGTTGAGGAmA |
| SEQ ID NO: 506 | TCCTCAACGCGGAGAGGTCGACCmU |
| SEQ ID NO: 507 | GGATGGTCGCCAGGGTGGAGCCTmC |
| SEQ ID NO: 508 | AGGCTCCACCCTGGCGACCATCCmU |
| SEQ ID NO: 509 | AAGGCTACCTGCCCCATGAACCTmC |
| SEQ ID NO: 510 | AGGTTCATGGGGCAGGTAGCCTTmG |
| SEQ ID NO: 511 | GGACGACCTTACCGTCGGTGGTCmU |
| SEQ ID NO: 512 | GACCACCGACGGTAAGGTCGTCCmA |
| SEQ ID NO: 513 | GGAGCTCTCACGTCTACGGCCTCmU |
| SEQ ID NO: 514 | GAGGCCGTAGACGTGAGAGCTCCmC |
| SEQ ID NO: 515 | GAGGTCGTTCTTGCGGATGGGCAmG |
| SEQ ID NO: 516 | TGCCCATCCGCAAGAACGACCTCmC |
| SEQ ID NO: 517 | CGAGCACTCCGACCTCTTCTATGmG |
| SEQ ID NO: 518 | CATAGAAGAGGTCGGAGTGCTCGmU |
| SEQ ID NO: 519 | TCGGGCTCCTGGTTTCGGCTGAGmA |
| SEQ ID NO: 520 | CTCAGCCGAAACCAGGAGCCCGAmU |
| SEQ ID NO: 521 | TACATGAGGCTCACGTACACTCCmU |
| SEQ ID NO: 522 | GGAGTGTACGTGAGCCTCATGTAmC |
| SEQ ID NO: 523 | CGCGGAGGCTTATGCTGATTCGTmU |
| SEQ ID NO: 524 | ACGAATCAGCATAAGCCTCCGCGmA |
| SEQ ID NO: 525 | CACATGAACCCGTATCGCGAGATmG |
| SEQ ID NO: 526 | ATCTCGCGATACGGGTTCATGTGmU |
| SEQ ID NO: 527 | TCTTTATCACAGTGGATGCATATmG |
| SEQ ID NO: 528 | ATATGCATCCACTGTGATAAAGAmA |
| SEQ ID NO: 529 | ACAGATGGTTAGCGAGTGACAGTmA |
| SEQ ID NO: 530 | ACTGTCACTCGCTAACCATCTGTmU |
| SEQ ID NO: 531 | AGTTGTCCGACACTTCATCGGTAmA |
| SEQ ID NO: 532 | TACCGATGAAGTGTCGGACAACTmU |
| SEQ ID NO: 533 | ACCGAGTGAATGGAAGAAAAACGmA |
| SEQ ID NO: 534 | CGTTTTCTTCCATTCACTCGGTmU |
| SEQ ID NO: 535 | ACAGCAGGTTTTCTTAAAAAACGmU |
| SEQ ID NO: 536 | CGTTTTTTAAGAAAACCTGCTGTmG |
| SEQ ID NO: 537 | TTAAGAAGAGACCAAAATATGGTmC |
| SEQ ID NO: 538 | ACCATATTTTGGTCTCTTCTTAAmU |
| SEQ ID NO: 539 | TTCTAAACATTAGTTCTCATCACmC |
| SEQ ID NO: 540 | GTGATGAGAACTAATGTTTAGAAmA |
| SEQ ID NO: 541 | CATCTAGTTTGCAACGGTCCAGTmU |
| SEQ ID NO: 542 | ACTGGACCGTTGCAAACTAGATGmG |
| SEQ ID NO: 543 | GACTCGCAGCGAGAGAATTTTTmU |
| SEQ ID NO: 544 | AAAAAATTCTCTCGCTGCGAGTCmC |
| SEQ ID NO: 545 | ATTCACTTTCGGACAAATCGAACmU |
| SEQ ID NO: 546 | GTTCGATTTGTCCGAAAGTGAATmU |
| SEQ ID NO: 547 | AACCATGAGACCTTTTCGCCGCAmG |
| SEQ ID NO: 548 | TGCGGCGAAAAGGTCTCATGGTTmA |
| SEQ ID NO: 549 | GGCCGTTAGATTTTAGTGACGATmG |
| SEQ ID NO: 550 | ATCGTCACTAAAATCTAACGGCCmG |
| SEQ ID NO: 551 | GCAACGTGCCGCATGCATCCATTmC |
| SEQ ID NO: 552 | AATGGATGCATGCGGCACGTTGCmG |
| SEQ ID NO: 553 | ACAGTACATGTAGGAGTACTGTGmC |
| SEQ ID NO: 554 | CACAGTACTCCTACATGTACTGTmG |
| SEQ ID NO: 555 | ACATTCAGTCTCTCACTAGTTmG |
| SEQ ID NO: 556 | AACTAGTGAGAGACTGAATGTmA |
| SEQ ID NO: 557 | CTACAAAGACATGAGCTGCCGGGmA |
| SEQ ID NO: 558 | CCCGGCAGCTCATGTCTTTGTAGmC |
| SEQ ID NO: 559 | GAGCGAGCGAGCCTGACGGTCTCmA |
| SEQ ID NO: 560 | GAGACCGTCAGGCTCGCTCGCTCmC |
| SEQ ID NO: 561 | ACTCCCAAGCCAATTATTATAAGmA |
| SEQ ID NO: 562 | CTTATAATAATTGGCTTGGGAGTmG |
| SEQ ID NO: 563 | ACTCCAGCTCTTAACCAATCCACmU |

| | Sequences |
|---|---|
| SEQ ID NO: 564 | GTGGATTGGTTAAGAGCTGGAGTmU |
| SEQ ID NO: 565 | CACCTCCTCTGCTTTGCTCTGCCmA |
| SEQ ID NO: 566 | GGCAGAGCAAAGCAGAGGAGGTGmG |
| SEQ ID NO: 567 | GGGGGCAGAGGAGCTCCCCCTCCmC |
| SEQ ID NO: 568 | GGAGGGGGAGCTCCTCTGCCCCCmC |
| SEQ ID NO: 569 | TCGCCATGTCTAGCAGCGACCCGmG |
| SEQ ID NO: 570 | CGGGTCGCTGCTAGACATGGCGAmG |
| SEQ ID NO: 571 | GCGCGTCGTCGTTCTCGGTTCGCmC |
| SEQ ID NO: 572 | GCGAACCGAGAACGACGACGCGCmG |
| SEQ ID NO: 573 | GGCGACGAGTGGGCCCGGCCCGAmG |
| SEQ ID NO: 574 | TCGGGCCGGGCCCACTCGTCGCCmG |
| SEQ ID NO: 575 | ATCTGCCGTCTCCCGCCCACCAGmC |
| SEQ ID NO: 576 | CTGGTGGGCGGGAGACGGCAGATmG |
| SEQ ID NO: 577 | AGCCGGGCAACCGGAAGCAGCAGmA |
| SEQ ID NO: 578 | CTGCTGCTTCCGGTTGCCCGGCTmA |
| SEQ ID NO: 579 | CCTGCTCCTGCTGGCCGCAGCAGmC |
| SEQ ID NO: 580 | CTGCTGCGGCCAGCAGGAGCAGGmG |
| SEQ ID NO: 581 | CGCCTACTACATCTGCCGGTGGCmG |
| SEQ ID NO: 582 | GCCACCGGCAGATGTAGTAGGCGmU |
| SEQ ID NO: 583 | TCCTCCTTCTTCGCCTCCCCCTCmC |
| SEQ ID NO: 584 | GAGGGGGAGGCGAAGAAGGAGGAmG |

| CATS oligonucleotide sequences for silencing Old Gold gene (mC = 2'-O-methyl cytosine, mG = 2'-O-methyl guanine, mA = 2'-O-methyl adenine, mT = 2'-O-methyl thymine, mU = 2'-O-methyl uracil) | |
|---|---|
| SEQ ID NO: 585 | GGTTTAAAAAAGATTTCTTTTTTmU |
| SEQ ID NO: 586 | AAAAAAGAAATCTTTTTTAAACCmU |
| SEQ ID NO: 587 | GTAATCGACACACTAATGCAAAGmA |
| SEQ ID NO: 588 | CTTTGCATTAGTGTGTCGATTACmU |
| SEQ ID NO: 589 | AACATCTTGGACCTAAATAATTGmU |
| SEQ ID NO: 590 | CAATTATTTAGGTCCAAGATGTTmU |
| SEQ ID NO: 591 | CTTTCCATTTTCATCTTTAAATAmU |
| SEQ ID NO: 592 | TATTTAAAGATGAAAATGGAAAGmG |
| SEQ ID NO: 593 | ACAATTTTTTTTGGGCTAAAATmG |
| SEQ ID NO: 594 | ATTTTAGCCCAAAAAAAAATTGTmG |
| SEQ ID NO: 595 | TGGTGGAGTTATGACCACATATTmG |
| SEQ ID NO: 596 | AATATGTGGTCATAACTCCACCAmU |
| SEQ ID NO: 597 | AGTGCTCAAAAGGAGAGTCTACTmG |
| SEQ ID NO: 598 | AGTAGACTCTCCTTTTGAGCACTmU |
| SEQ ID NO: 599 | CCACCACAAGTACTATGCAACAAmA |
| SEQ ID NO: 600 | TTGTTGCATAGTACTTGTGGTGGmA |
| SEQ ID NO: 601 | AAGAAAATGGAAACTTTTCTCTCmU |
| SEQ ID NO: 602 | GAGAGAAAAGTTTCCATTTTCTTmG |
| SEQ ID NO: 603 | CACTAGCTGTTTACATGGTGAGCmA |
| SEQ ID NO: 604 | GCTCACCATGTAAACAGCTAGTGmA |
| SEQ ID NO: 605 | AGAAATACTTAGTATATATCTATmA |
| SEQ ID NO: 606 | ATAGATATATACTAAGTATTTCTmA |
| SEQ ID NO: 607 | ACTTTTCATTCTGTAATTCTTTAmA |
| SEQ ID NO: 608 | TAAAGAATTACAGAATGAAAAGTmG |
| SEQ ID NO: 609 | CTGTTTAAAGCTTGATTTTTTTmA |
| SEQ ID NO: 610 | AAAAAAATCAAGCTTTAAACAGmU |
| SEQ ID NO: 611 | ATGTTCTGCTTCATTTGTGTTGAmA |
| SEQ ID NO: 612 | TCAACACAAATGAAGCAGAACATmG |
| SEQ ID NO: 613 | ATTGGGGAACTTTCTTGAATCCAmG |
| SEQ ID NO: 614 | TGGATTCAAGAAAGTTCCCCAATmU |
| SEQ ID NO: 615 | CATTTGAAGTTTTCTTGAAACAAmA |
| SEQ ID NO: 616 | TTGTTTCAAGAAAACTTCAAATGmG |
| SEQ ID NO: 617 | CATTACCCTGTTGGAAAAAGATGmG |
| SEQ ID NO: 618 | CATCTTTTTCCAACAGGGTAATGmA |
| SEQ ID NO: 619 | TACTTTGTTGAAAACCCCAAATAmA |
| SEQ ID NO: 620 | TATTTGGGGTTTTCAACAAAGTAmU |
| SEQ ID NO: 621 | CTTGAATTTCTGAACCCACATCAmU |
| SEQ ID NO: 622 | TGATGTGGGTTCAGAAATTCAAGmG |
| SEQ ID NO: 623 | GTTTTGCTGTTAAAGCTAGTACCmU |
| SEQ ID NO: 624 | GGTACTAGCTTTAACAGCAAAACmC |
| SEQ ID NO: 625 | GGTTCTAGGAAGTTTTGTGAAACmU |
| SEQ ID NO: 626 | GTTTCACAAAACTTCCTAGAACCmA |
| SEQ ID NO: 627 | TGGGTAGAAGTGTTTGTGTTAAGmG |
| SEQ ID NO: 628 | CTTAACACAAACACTTCTACCCAmA |
| SEQ ID NO: 629 | TAGTAGTAGTGCTCTTTTAGAGCmU |
| SEQ ID NO: 630 | GCTCTAAAAGAGCACTACTACTAmC |
| SEQ ID NO: 631 | GTACCTGAGACCAAAAGGAGAAmU |
| SEQ ID NO: 632 | TTCTCCTTTTGGTCTCAGGTACmA |
| SEQ ID NO: 633 | TTGATTTTGAGCTTCCTATGTATmG |
| SEQ ID NO: 634 | ATACATAGGAAGCTCAAAATCAAmG |
| SEQ ID NO: 635 | CTTGCTGTGGTTGGTGGTGGCCCmU |
| SEQ ID NO: 636 | GGGCCACCACCAACCACAGCAAGmA |
| SEQ ID NO: 637 | CAGGACTTGCTGTTGCACAGCAAmG |

-continued

| Sequences | |
|---|---|
| SEQ ID NO: 638 | TTGCTGTGCAACAGCAAGTCCTGmC |
| SEQ ID NO: 639 | TTCTGAAGCAGGACTCTCTGTTTmG |
| SEQ ID NO: 640 | AAACAGAGAGTCCTGCTTCAGAAmA |
| SEQ ID NO: 641 | TCAATTGATCCGAATCCTAAATTmG |
| SEQ ID NO: 642 | AATTTAGGATTCGGATCAATTGAmA |
| SEQ ID NO: 643 | TATGGCCTAATAACTATGGTGTTmU |
| SEQ ID NO: 644 | AACACCATAGTTATTAGGCCATAmU |
| SEQ ID NO: 645 | TTGTTAGATTGTCTAGATGCTACmC |
| SEQ ID NO: 646 | GTAGCATCTAGACAATCTAACAAmG |
| SEQ ID NO: 647 | GGTCTGGTGCAGCAGTGTACATTmG |
| SEQ ID NO: 648 | AATGTACACTGCTGCACCAGACCmA |
| SEQ ID NO: 649 | TGATAATACGGCTAAAGATCTTCmA |
| SEQ ID NO: 650 | GAAGATCTTTAGCCGTATTATCAmU |
| SEQ ID NO: 651 | AGACCTTATGGAAGGGTTAACCGmG |

-continued

| Sequences | |
|---|---|
| SEQ ID NO: 652 | CGGTTAACCCTTCCATAAGGTCTmA |
| SEQ ID NO: 653 | AACAGCTGAAATCGAAAATGATGmC |
| SEQ ID NO: 654 | CATCATTTTCGATTTCAGCTGTTmU |
| SEQ ID NO: 655 | TTCCACCAAGCCAAAGTTATAAAmG |
| SEQ ID NO: 656 | TTTATAACTTTGGCTTGGTGGAAmU |
| SEQ ID NO: 657 | TGATTCATGAGGAATCGAAATCCmA |
| SEQ ID NO: 658 | GGATTTCGATTCCTCATGAATCAmC |
| SEQ ID NO: 659 | GTTGATATGCAATGATGGTATTAmC |
| SEQ ID NO: 660 | TAATACCATCATTGCATATCAACmA |
| SEQ ID NO: 661 | ATTCAGGCAACGGTGGTGCTCGAmU |
| SEQ ID NO: 662 | TCGAGCACCACCGTTGCCTGAATmA |
| SEQ ID NO: 663 | CAACTGGCTTCTCTAGATCTCTTmG |
| SEQ ID NO: 664 | AAGAGATCTAGAGAAGCCAGTTGmC |

What is claimed is:

1. A double stranded artificial nucleic acid construct comprising (a) a first strand and a second strand each having a length of 20 to 30 nucleotides or nucleosides or a combination thereof; and (b) a terminal end overhang at one or both of a 3' end of the first strand or a 3' end of the second strand; wherein one or both of the 3' terminal end overhangs comprise a ribose unit having a methoxy group (—O-Me) at a 2' position; and
   wherein at least 80% of the sugars in the double stranded artificial nucleic acid construct comprises a deoxyribose, and wherein the nucleic acid construct does not comprise a regulatory element.

2. The construct of claim 1, wherein both the 3' end of the first strand and the 3' end of the second strand comprise terminal end overhangs.

3. The construct of claim 1, wherein one strand of the double stranded artificial nucleic acid construct comprises at least 80% sequence identity to a portion of a transcription regulatory region of a gene of an agricultural object.

4. The construct of claim 2, wherein both of the 3' terminal end overhangs comprise a ribose unit having a methoxy group (—O-Me) at a 2' position.

5. The construct of claim 3, wherein the transcription regulatory region is a transcription start site, a TATA box, or an upstream activating sequence.

6. The construct of claim 1, wherein one or both of the terminal end overhangs is one nucleotide long.

7. The construct of claim 5, wherein the portion of the transcription regulatory region comprises at least 30% guanine cytosine (GC) content.

8. The construct of claim 4, wherein both terminal end overhangs are one nucleotide long.

9. The construct of claim 1, wherein every sugar in the double stranded artificial nucleic construct is a deoxyribose except for the terminal 3' sugar of the first strand and the second strand.

10. The construct of claim 4, wherein every sugar in the double stranded artificial nucleic construct is a deoxyribose except for the terminal 3' sugar of the first strand and the second strand.

11. The construct of claim 10, wherein the first strand and the second strand each have a length of 24 nucleotides.

12. A formulation comprising the double-stranded artificial nucleic acid construct of claim 1 and an excipient.

13. The formulation of claim 12, wherein the formulation comprises an excipient and a plurality of double stranded artificial nucleic acid constructs.

14. The formulation of claim 12, wherein the excipient is water.

* * * * *

SEQUENCE LISTING

```
Sequence total quantity: 674
SEQ ID NO: 1              moltype = DNA   length = 24
FEATURE                   Location/Qualifiers
source                    1..24
                          mol_type = other DNA
                          organism = Synthetic construct
SEQUENCE: 1
tggctactat gtattgatgt taac                                                24

SEQ ID NO: 2              moltype = DNA   length = 24
FEATURE                   Location/Qualifiers
source                    1..24
                          mol_type = other DNA
                          organism = Synthetic construct
SEQUENCE: 2
ttaacatcaa tacatagtag ccag                                                24

SEQ ID NO: 3              moltype = DNA   length = 24
FEATURE                   Location/Qualifiers
source                    1..24
                          mol_type = other DNA
                          organism = Synthetic construct
SEQUENCE: 3
ccattaagat gtactcgctc tgta                                                24

SEQ ID NO: 4              moltype = DNA   length = 24
FEATURE                   Location/Qualifiers
source                    1..24
                          mol_type = other DNA
                          organism = Synthetic construct
SEQUENCE: 4
acagagcgag tacatcttaa tgga                                                24

SEQ ID NO: 5              moltype = DNA   length = 24
FEATURE                   Location/Qualifiers
source                    1..24
                          mol_type = other DNA
                          organism = Synthetic construct
SEQUENCE: 5
taatcatttt tgtctgttat tttt                                                24

SEQ ID NO: 6              moltype = DNA   length = 24
FEATURE                   Location/Qualifiers
source                    1..24
```

```
                            mol_type = other DNA
                            organism = Synthetic construct
SEQUENCE: 6
aaaataacag acaaaaatga ttac                                              24

SEQ ID NO: 7               moltype = DNA   length = 24
FEATURE                    Location/Qualifiers
source                     1..24
                           mol_type = other DNA
                           organism = Synthetic construct
SEQUENCE: 7
gtctatattc agacagatga taat                                              24

SEQ ID NO: 8               moltype = DNA   length = 24
FEATURE                    Location/Qualifiers
source                     1..24
                           mol_type = other DNA
                           organism = Synthetic construct
SEQUENCE: 8
ttatcatctg tctgaatata gaca                                              24

SEQ ID NO: 9               moltype = DNA   length = 24
FEATURE                    Location/Qualifiers
source                     1..24
                           mol_type = other DNA
                           organism = Synthetic construct
SEQUENCE: 9
ctagacacat ataccaagta atga                                              24

SEQ ID NO: 10              moltype = DNA   length = 24
FEATURE                    Location/Qualifiers
source                     1..24
                           mol_type = other DNA
                           organism = Synthetic construct
SEQUENCE: 10
cattacttgg tatatgtgtc taga                                              24

SEQ ID NO: 11              moltype = DNA   length = 24
FEATURE                    Location/Qualifiers
source                     1..24
                           mol_type = other DNA
                           organism = Synthetic construct
SEQUENCE: 11
ggatataggg agtatgaaca actg                                              24

SEQ ID NO: 12              moltype = DNA   length = 24
FEATURE                    Location/Qualifiers
source                     1..24
                           mol_type = other DNA
                           organism = Synthetic construct
SEQUENCE: 12
agttgttcat actccctata tcct                                              24

SEQ ID NO: 13              moltype = DNA   length = 24
FEATURE                    Location/Qualifiers
source                     1..24
                           mol_type = other DNA
                           organism = Synthetic construct
SEQUENCE: 13
caattagttc cgtattgata atat                                              24

SEQ ID NO: 14              moltype = DNA   length = 24
FEATURE                    Location/Qualifiers
source                     1..24
                           mol_type = other DNA
                           organism = Synthetic construct
SEQUENCE: 14
tattatcaat acggaactaa ttgt                                              24

SEQ ID NO: 15              moltype = DNA   length = 24
FEATURE                    Location/Qualifiers
source                     1..24
                           mol_type = other DNA
                           organism = Synthetic construct
SEQUENCE: 15
ggatcgacgt atttataata atac                                              24

SEQ ID NO: 16              moltype = DNA   length = 24
FEATURE                    Location/Qualifiers
```

```
source                  1..24
                        mol_type = other DNA
                        organism = Synthetic construct
SEQUENCE: 16
tattattata aatacgtcga tcca                                              24

SEQ ID NO: 17           moltype = DNA  length = 24
FEATURE                 Location/Qualifiers
source                  1..24
                        mol_type = other DNA
                        organism = Synthetic construct
SEQUENCE: 17
tgttctatat ctatatttaa ttat                                              24

SEQ ID NO: 18           moltype = DNA  length = 24
FEATURE                 Location/Qualifiers
source                  1..24
                        mol_type = other DNA
                        organism = Synthetic construct
SEQUENCE: 18
taattaaata tagatataga acag                                              24

SEQ ID NO: 19           moltype = DNA  length = 24
FEATURE                 Location/Qualifiers
source                  1..24
                        mol_type = other DNA
                        organism = Synthetic construct
SEQUENCE: 19
gcggaggtct ccactcttct ctct                                              24

SEQ ID NO: 20           moltype = DNA  length = 24
FEATURE                 Location/Qualifiers
source                  1..24
                        mol_type = other DNA
                        organism = Synthetic construct
SEQUENCE: 20
gagagaagag tggagacctc cgca                                              24

SEQ ID NO: 21           moltype = DNA  length = 24
FEATURE                 Location/Qualifiers
source                  1..24
                        mol_type = other DNA
                        organism = Synthetic construct
SEQUENCE: 21
ccatctttatc atcgcccacg taca                                             24

SEQ ID NO: 22           moltype = DNA  length = 24
FEATURE                 Location/Qualifiers
source                  1..24
                        mol_type = other DNA
                        organism = Synthetic construct
SEQUENCE: 22
gtacgtgggc gatgataaga tgga                                              24

SEQ ID NO: 23           moltype = DNA  length = 24
FEATURE                 Location/Qualifiers
source                  1..24
                        mol_type = other DNA
                        organism = Synthetic construct
SEQUENCE: 23
cccaattcct cgcaactggg ctcc                                              24

SEQ ID NO: 24           moltype = DNA  length = 24
FEATURE                 Location/Qualifiers
source                  1..24
                        mol_type = other DNA
                        organism = Synthetic construct
SEQUENCE: 24
gagcccagtt gcgaggaatt gggt                                              24

SEQ ID NO: 25           moltype = DNA  length = 24
FEATURE                 Location/Qualifiers
source                  1..24
                        mol_type = other DNA
                        organism = Synthetic construct
SEQUENCE: 25
cgcctccacg acactgcccc ccgc                                              24

SEQ ID NO: 26           moltype = DNA  length = 24
```

```
FEATURE                 Location/Qualifiers
source                  1..24
                        mol_type = other DNA
                        organism = Synthetic construct
SEQUENCE: 26
cgggggcag tgtcgtggag gcgg                                               24

SEQ ID NO: 27           moltype = DNA  length = 24
FEATURE                 Location/Qualifiers
source                  1..24
                        mol_type = other DNA
                        organism = Synthetic construct
SEQUENCE: 27
caagtccgcc gcctccattc ttca                                              24

SEQ ID NO: 28           moltype = DNA  length = 24
FEATURE                 Location/Qualifiers
source                  1..24
                        mol_type = other DNA
                        organism = Synthetic construct
SEQUENCE: 28
gaagaatgga ggcggcggac ttga                                              24

SEQ ID NO: 29           moltype = DNA  length = 25
FEATURE                 Location/Qualifiers
source                  1..25
                        mol_type = other DNA
                        organism = Synthetic construct
SEQUENCE: 29
gtgcgttggt gggtctgaaa caata                                             25

SEQ ID NO: 30           moltype = DNA  length = 25
FEATURE                 Location/Qualifiers
source                  1..25
                        mol_type = other DNA
                        organism = Synthetic construct
SEQUENCE: 30
attgtttcag acccaccaac gcaca                                             25

SEQ ID NO: 31           moltype = DNA  length = 24
FEATURE                 Location/Qualifiers
source                  1..24
                        mol_type = other DNA
                        organism = Synthetic construct
SEQUENCE: 31
gtctcaaaag gaggtgagct ggga                                              24

SEQ ID NO: 32           moltype = DNA  length = 24
FEATURE                 Location/Qualifiers
source                  1..24
                        mol_type = other DNA
                        organism = Synthetic construct
SEQUENCE: 32
cccagctcac ctcctttga gacg                                               24

SEQ ID NO: 33           moltype = DNA  length = 24
FEATURE                 Location/Qualifiers
source                  1..24
                        mol_type = other DNA
                        organism = Synthetic construct
SEQUENCE: 33
tttagccgac taattttaga tgag                                              24

SEQ ID NO: 34           moltype = DNA  length = 24
FEATURE                 Location/Qualifiers
source                  1..24
                        mol_type = other DNA
                        organism = Synthetic construct
SEQUENCE: 34
tcatctaaaa ttagtcggct aaat                                              24

SEQ ID NO: 35           moltype = DNA  length = 24
FEATURE                 Location/Qualifiers
source                  1..24
                        mol_type = other DNA
                        organism = Synthetic construct
SEQUENCE: 35
taatctttag ttccgtgccc ccgc                                              24
```

```
SEQ ID NO: 36              moltype = DNA   length = 24
FEATURE                    Location/Qualifiers
source                     1..24
                           mol_type = other DNA
                           organism = Synthetic construct
SEQUENCE: 36
cgggggcacg gaactaaaga ttat                                              24

SEQ ID NO: 37              moltype = DNA   length = 24
FEATURE                    Location/Qualifiers
source                     1..24
                           mol_type = other DNA
                           organism = Synthetic construct
SEQUENCE: 37
tgcaggctca ccccgacgtg cccc                                              24

SEQ ID NO: 38              moltype = DNA   length = 24
FEATURE                    Location/Qualifiers
source                     1..24
                           mol_type = other DNA
                           organism = Synthetic construct
SEQUENCE: 38
gggcacgtcg gggtgagcct gcac                                              24

SEQ ID NO: 39              moltype = DNA   length = 24
FEATURE                    Location/Qualifiers
source                     1..24
                           mol_type = other DNA
                           organism = Synthetic construct
SEQUENCE: 39
gccctccgcg cgcgatgccc ccat                                              24

SEQ ID NO: 40              moltype = DNA   length = 24
FEATURE                    Location/Qualifiers
source                     1..24
                           mol_type = other DNA
                           organism = Synthetic construct
SEQUENCE: 40
tgggggcatc gcgcgcggag ggca                                              24

SEQ ID NO: 41              moltype = DNA   length = 24
FEATURE                    Location/Qualifiers
source                     1..24
                           mol_type = other DNA
                           organism = Synthetic construct
SEQUENCE: 41
caccgacgca gagctcgccc atgc                                              24

SEQ ID NO: 42              moltype = DNA   length = 24
FEATURE                    Location/Qualifiers
source                     1..24
                           mol_type = other DNA
                           organism = Synthetic construct
SEQUENCE: 42
catgggcgag ctctgcgtcg gtgt                                              24

SEQ ID NO: 43              moltype = DNA   length = 24
FEATURE                    Location/Qualifiers
source                     1..24
                           mol_type = other DNA
                           organism = Synthetic construct
SEQUENCE: 43
cacgtgcccc ggcggcgtcg cgat                                              24

SEQ ID NO: 44              moltype = DNA   length = 24
FEATURE                    Location/Qualifiers
source                     1..24
                           mol_type = other DNA
                           organism = Synthetic construct
SEQUENCE: 44
tcgcgacgcc gccggggcac gtgc                                              24

SEQ ID NO: 45              moltype = DNA   length = 24
FEATURE                    Location/Qualifiers
source                     1..24
                           mol_type = other DNA
                           organism = Synthetic construct
SEQUENCE: 45
tatccccgcc gtcgcgcgcc tacg                                              24
```

```
SEQ ID NO: 46          moltype = DNA   length = 24
FEATURE                Location/Qualifiers
source                 1..24
                       mol_type = other DNA
                       organism = Synthetic construct
SEQUENCE: 46
gtaggcgcgc gacggcgggg atac                                              24

SEQ ID NO: 47          moltype = DNA   length = 24
FEATURE                Location/Qualifiers
source                 1..24
                       mol_type = other DNA
                       organism = Synthetic construct
SEQUENCE: 47
gtacctggag cagaagcgat ttcg                                              24

SEQ ID NO: 48          moltype = DNA   length = 24
FEATURE                Location/Qualifiers
source                 1..24
                       mol_type = other DNA
                       organism = Synthetic construct
SEQUENCE: 48
gaaatcgctt ctgctccagg taca                                              24

SEQ ID NO: 49          moltype = DNA   length = 24
FEATURE                Location/Qualifiers
source                 1..24
                       mol_type = other DNA
                       organism = Synthetic construct
SEQUENCE: 49
tgccgaggag ctcaccgctg tgaa                                              24

SEQ ID NO: 50          moltype = DNA   length = 24
FEATURE                Location/Qualifiers
source                 1..24
                       mol_type = other DNA
                       organism = Synthetic construct
SEQUENCE: 50
tcacagcggt gagctcctcg gcaa                                              24

SEQ ID NO: 51          moltype = DNA   length = 24
FEATURE                Location/Qualifiers
source                 1..24
                       mol_type = other DNA
                       organism = Synthetic construct
SEQUENCE: 51
tagtcccgtc ccctccaggt cctg                                              24

SEQ ID NO: 52          moltype = DNA   length = 24
FEATURE                Location/Qualifiers
source                 1..24
                       mol_type = other DNA
                       organism = Synthetic construct
SEQUENCE: 52
aggacctgga ggggacggga ctaa                                              24

SEQ ID NO: 53          moltype = DNA   length = 24
FEATURE                Location/Qualifiers
source                 1..24
                       mol_type = other DNA
                       organism = Synthetic construct
SEQUENCE: 53
aattcacttg tgtattcccc cgaa                                              24

SEQ ID NO: 54          moltype = DNA   length = 24
FEATURE                Location/Qualifiers
source                 1..24
                       mol_type = other DNA
                       organism = Synthetic construct
SEQUENCE: 54
tcggggaat acacaagtga attg                                               24

SEQ ID NO: 55          moltype = DNA   length = 24
FEATURE                Location/Qualifiers
source                 1..24
                       mol_type = other DNA
                       organism = Synthetic construct
SEQUENCE: 55
```

```
gagacagtct gcacggctcc tatc                                              24

SEQ ID NO: 56           moltype = DNA   length = 24
FEATURE                 Location/Qualifiers
source                  1..24
                        mol_type = other DNA
                        organism = Synthetic construct
SEQUENCE: 56
ataggagccg tgcagactgt ctcg                                              24

SEQ ID NO: 57           moltype = DNA   length = 24
FEATURE                 Location/Qualifiers
source                  1..24
                        mol_type = other DNA
                        organism = Synthetic construct
SEQUENCE: 57
gcatgtaccc aataccctgt tttg                                              24

SEQ ID NO: 58           moltype = DNA   length = 24
FEATURE                 Location/Qualifiers
source                  1..24
                        mol_type = other DNA
                        organism = Synthetic construct
SEQUENCE: 58
aaaacagggt attgggtaca tgct                                              24

SEQ ID NO: 59           moltype = DNA   length = 24
FEATURE                 Location/Qualifiers
source                  1..24
                        mol_type = other DNA
                        organism = Synthetic construct
SEQUENCE: 59
tgaccttggg tactattata gcac                                              24

SEQ ID NO: 60           moltype = DNA   length = 24
FEATURE                 Location/Qualifiers
source                  1..24
                        mol_type = other DNA
                        organism = Synthetic construct
SEQUENCE: 60
tgctataata gtacccaagg tcaa                                              24

SEQ ID NO: 61           moltype = DNA   length = 24
FEATURE                 Location/Qualifiers
source                  1..24
                        mol_type = other DNA
                        organism = Synthetic construct
SEQUENCE: 61
tttcagttcg agtgttagac cctg                                              24

SEQ ID NO: 62           moltype = DNA   length = 24
FEATURE                 Location/Qualifiers
source                  1..24
                        mol_type = other DNA
                        organism = Synthetic construct
SEQUENCE: 62
agggtctaac actcgaactg aaac                                              24

SEQ ID NO: 63           moltype = DNA   length = 24
FEATURE                 Location/Qualifiers
source                  1..24
                        mol_type = other DNA
                        organism = Synthetic construct
SEQUENCE: 63
cttttttggaa ttcttctgac cagg                                             24

SEQ ID NO: 64           moltype = DNA   length = 24
FEATURE                 Location/Qualifiers
source                  1..24
                        mol_type = other DNA
                        organism = Synthetic construct
SEQUENCE: 64
ctggtcagaa gaattccaaa aaga                                              24

SEQ ID NO: 65           moltype = DNA   length = 24
FEATURE                 Location/Qualifiers
source                  1..24
                        mol_type = other DNA
                        organism = Synthetic construct
```

-continued

```
SEQUENCE: 65
caagaaaatt aaggatatat agcg                                              24

SEQ ID NO: 66           moltype = DNA  length = 24
FEATURE                 Location/Qualifiers
source                  1..24
                        mol_type = other DNA
                        organism = Synthetic construct
SEQUENCE: 66
gctatatatc cttaattttc ttgg                                              24

SEQ ID NO: 67           moltype = DNA  length = 24
FEATURE                 Location/Qualifiers
source                  1..24
                        mol_type = other DNA
                        organism = Synthetic construct
SEQUENCE: 67
taaggcatgt cgataataaa gact                                              24

SEQ ID NO: 68           moltype = DNA  length = 24
FEATURE                 Location/Qualifiers
source                  1..24
                        mol_type = other DNA
                        organism = Synthetic construct
SEQUENCE: 68
gtctttatta tcgacatgcc ttag                                              24

SEQ ID NO: 69           moltype = DNA  length = 24
FEATURE                 Location/Qualifiers
source                  1..24
                        mol_type = other DNA
                        organism = Synthetic construct
SEQUENCE: 69
ataggaccga gcaactcgga ttcg                                              24

SEQ ID NO: 70           moltype = DNA  length = 24
FEATURE                 Location/Qualifiers
source                  1..24
                        mol_type = other DNA
                        organism = Synthetic construct
SEQUENCE: 70
gaatccgagt tgctcggtcc tatt                                              24

SEQ ID NO: 71           moltype = DNA  length = 24
FEATURE                 Location/Qualifiers
source                  1..24
                        mol_type = other DNA
                        organism = Synthetic construct
SEQUENCE: 71
gactcggact tggactgtgc aact                                              24

SEQ ID NO: 72           moltype = DNA  length = 24
FEATURE                 Location/Qualifiers
source                  1..24
                        mol_type = other DNA
                        organism = Synthetic construct
SEQUENCE: 72
gttgcacagt ccaagtccga gtca                                              24

SEQ ID NO: 73           moltype = DNA  length = 24
FEATURE                 Location/Qualifiers
source                  1..24
                        mol_type = other DNA
                        organism = Synthetic construct
SEQUENCE: 73
agccgggata ctcaaaatcg aaat                                              24

SEQ ID NO: 74           moltype = DNA  length = 24
FEATURE                 Location/Qualifiers
source                  1..24
                        mol_type = other DNA
                        organism = Synthetic construct
SEQUENCE: 74
tttcgatttt gagtatcccg gctg                                              24

SEQ ID NO: 75           moltype = DNA  length = 24
FEATURE                 Location/Qualifiers
source                  1..24
                        mol_type = other DNA
```

```
                          organism = Synthetic construct
SEQUENCE: 75
actcggtcca taggttaata ctca                                              24

SEQ ID NO: 76           moltype = DNA   length = 24
FEATURE                 Location/Qualifiers
source                  1..24
                        mol_type = other DNA
                        organism = Synthetic construct
SEQUENCE: 76
gagtattaac ctatggaccg agtc                                              24

SEQ ID NO: 77           moltype = DNA   length = 24
FEATURE                 Location/Qualifiers
source                  1..24
                        mol_type = other DNA
                        organism = Synthetic construct
SEQUENCE: 77
tcatattttaa catctaaacg ttcg                                             24

SEQ ID NO: 78           moltype = DNA   length = 24
FEATURE                 Location/Qualifiers
source                  1..24
                        mol_type = other DNA
                        organism = Synthetic construct
SEQUENCE: 78
gaacgtttag atgtaaaata tgag                                              24

SEQ ID NO: 79           moltype = DNA   length = 24
FEATURE                 Location/Qualifiers
source                  1..24
                        mol_type = other DNA
                        organism = Synthetic construct
SEQUENCE: 79
tggaagcaaa cacccccttaa gacg                                             24

SEQ ID NO: 80           moltype = DNA   length = 24
FEATURE                 Location/Qualifiers
source                  1..24
                        mol_type = other DNA
                        organism = Synthetic construct
SEQUENCE: 80
gtctaagggg gtgtttgctt ccac                                              24

SEQ ID NO: 81           moltype = DNA   length = 24
FEATURE                 Location/Qualifiers
source                  1..24
                        mol_type = other DNA
                        organism = Synthetic construct
SEQUENCE: 81
ccacctcttg tcgaccattt gtag                                              24

SEQ ID NO: 82           moltype = DNA   length = 24
FEATURE                 Location/Qualifiers
source                  1..24
                        mol_type = other DNA
                        organism = Synthetic construct
SEQUENCE: 82
tacaaatggt cgacaagagg tggt                                              24

SEQ ID NO: 83           moltype = DNA   length = 24
FEATURE                 Location/Qualifiers
source                  1..24
                        mol_type = other DNA
                        organism = Synthetic construct
SEQUENCE: 83
catgttccgt tctgccgact gatg                                              24

SEQ ID NO: 84           moltype = DNA   length = 24
FEATURE                 Location/Qualifiers
source                  1..24
                        mol_type = other DNA
                        organism = Synthetic construct
SEQUENCE: 84
atcagtcggc agaacggaac atga                                              24

SEQ ID NO: 85           moltype = DNA   length = 24
FEATURE                 Location/Qualifiers
source                  1..24
```

```
                              mol_type = other DNA
                              organism = Synthetic construct
SEQUENCE: 85
cctgcagctg cagctgcagt gcgt                                        24

SEQ ID NO: 86                 moltype = DNA  length = 24
FEATURE                       Location/Qualifiers
source                        1..24
                              mol_type = other DNA
                              organism = Synthetic construct
SEQUENCE: 86
cgcactgcag ctgcagctgc agga                                        24

SEQ ID NO: 87                 moltype = DNA  length = 24
FEATURE                       Location/Qualifiers
source                        1..24
                              mol_type = other DNA
                              organism = Synthetic construct
SEQUENCE: 87
actccatcgt ctattaatgg ctcg                                        24

SEQ ID NO: 88                 moltype = DNA  length = 24
FEATURE                       Location/Qualifiers
source                        1..24
                              mol_type = other DNA
                              organism = Synthetic construct
SEQUENCE: 88
gagccattaa tagacgatgg agta                                        24

SEQ ID NO: 89                 moltype = DNA  length = 24
FEATURE                       Location/Qualifiers
source                        1..24
                              mol_type = other DNA
                              organism = Synthetic construct
SEQUENCE: 89
ccagcgctcg gcttagacaa gcct                                        24

SEQ ID NO: 90                 moltype = DNA  length = 24
FEATURE                       Location/Qualifiers
source                        1..24
                              mol_type = other DNA
                              organism = Synthetic construct
SEQUENCE: 90
ggcttgtcta agccgagcgc tgga                                        24

SEQ ID NO: 91                 moltype = DNA  length = 24
FEATURE                       Location/Qualifiers
source                        1..24
                              mol_type = other DNA
                              organism = Synthetic construct
SEQUENCE: 91
atgaaggtca gtcagtagtc ccac                                        24

SEQ ID NO: 92                 moltype = DNA  length = 24
FEATURE                       Location/Qualifiers
source                        1..24
                              mol_type = other DNA
                              organism = Synthetic construct
SEQUENCE: 92
tgggactact gactgacctt catg                                        24

SEQ ID NO: 93                 moltype = DNA  length = 24
FEATURE                       Location/Qualifiers
source                        1..24
                              mol_type = other DNA
                              organism = Synthetic construct
SEQUENCE: 93
agcttttagt ctagctcgac agtc                                        24

SEQ ID NO: 94                 moltype = DNA  length = 24
FEATURE                       Location/Qualifiers
source                        1..24
                              mol_type = other DNA
                              organism = Synthetic construct
SEQUENCE: 94
actgtcgagc tagactaaaa gctg                                        24

SEQ ID NO: 95                 moltype = DNA  length = 24
FEATURE                       Location/Qualifiers
```

```
source                      1..24
                            mol_type = other DNA
                            organism = Synthetic construct
SEQUENCE: 95
ttctttctaa tccacctatt ttct                                          24

SEQ ID NO: 96               moltype = DNA   length = 24
FEATURE                     Location/Qualifiers
source                      1..24
                            mol_type = other DNA
                            organism = Synthetic construct
SEQUENCE: 96
gaaaataggt ggattagaaa gaac                                          24

SEQ ID NO: 97               moltype = DNA   length = 24
FEATURE                     Location/Qualifiers
source                      1..24
                            mol_type = other DNA
                            organism = Synthetic construct
SEQUENCE: 97
gcgactcact ctcgtagttg gtgt                                          24

SEQ ID NO: 98               moltype = DNA   length = 24
FEATURE                     Location/Qualifiers
source                      1..24
                            mol_type = other DNA
                            organism = Synthetic construct
SEQUENCE: 98
caccaactac gagagtgagt cgcc                                          24

SEQ ID NO: 99               moltype = DNA   length = 24
FEATURE                     Location/Qualifiers
source                      1..24
                            mol_type = other DNA
                            organism = Synthetic construct
SEQUENCE: 99
tcatgacctc ctcctcaagc tcgg                                          24

SEQ ID NO: 100              moltype = DNA   length = 24
FEATURE                     Location/Qualifiers
source                      1..24
                            mol_type = other DNA
                            organism = Synthetic construct
SEQUENCE: 100
cgagcttgag gaggaggtca tgaa                                          24

SEQ ID NO: 101              moltype = DNA   length = 24
FEATURE                     Location/Qualifiers
source                      1..24
                            mol_type = other DNA
                            organism = Synthetic construct
SEQUENCE: 101
ctcatatttg aagcctcctt gttc                                          24

SEQ ID NO: 102              moltype = DNA   length = 24
FEATURE                     Location/Qualifiers
source                      1..24
                            mol_type = other DNA
                            organism = Synthetic construct
SEQUENCE: 102
aacaaggagg cttcaaatat gaga                                          24

SEQ ID NO: 103              moltype = DNA   length = 24
FEATURE                     Location/Qualifiers
source                      1..24
                            mol_type = other DNA
                            organism = Synthetic construct
SEQUENCE: 103
agaaagcatc gaccttagca aggt                                          24

SEQ ID NO: 104              moltype = DNA   length = 24
FEATURE                     Location/Qualifiers
source                      1..24
                            mol_type = other DNA
                            organism = Synthetic construct
SEQUENCE: 104
ccttgctaag gtcgatgctt tctt                                          24

SEQ ID NO: 105              moltype = DNA   length = 24
```

```
FEATURE                 Location/Qualifiers
source                  1..24
                        mol_type = other DNA
                        organism = Synthetic construct
SEQUENCE: 105
ttgtccatgc gcttggtgag gtcg                                              24

SEQ ID NO: 106          moltype = DNA   length = 24
FEATURE                 Location/Qualifiers
source                  1..24
                        mol_type = other DNA
                        organism = Synthetic construct
SEQUENCE: 106
gacctcacca agcgcatgga caag                                              24

SEQ ID NO: 107          moltype = DNA   length = 24
FEATURE                 Location/Qualifiers
source                  1..24
                        mol_type = other DNA
                        organism = Synthetic construct
SEQUENCE: 107
aatctaacct ttgagtacca aatg                                              24

SEQ ID NO: 108          moltype = DNA   length = 24
FEATURE                 Location/Qualifiers
source                  1..24
                        mol_type = other DNA
                        organism = Synthetic construct
SEQUENCE: 108
atttggtact caaaggttag attg                                              24

SEQ ID NO: 109          moltype = DNA   length = 24
FEATURE                 Location/Qualifiers
source                  1..24
                        mol_type = other DNA
                        organism = Synthetic construct
SEQUENCE: 109
tggagacaca tacacagaga agaa                                              24

SEQ ID NO: 110          moltype = DNA   length = 24
FEATURE                 Location/Qualifiers
source                  1..24
                        mol_type = other DNA
                        organism = Synthetic construct
SEQUENCE: 110
tcttctctgt gtatgtgtct ccat                                              24

SEQ ID NO: 111          moltype = DNA   length = 24
FEATURE                 Location/Qualifiers
source                  1..24
                        mol_type = other DNA
                        organism = Synthetic construct
SEQUENCE: 111
cttgtttgga ttgaaaccat taca                                              24

SEQ ID NO: 112          moltype = DNA   length = 24
FEATURE                 Location/Qualifiers
source                  1..24
                        mol_type = other DNA
                        organism = Synthetic construct
SEQUENCE: 112
gtaatggttt caatccaaac aaga                                              24

SEQ ID NO: 113          moltype = DNA   length = 24
FEATURE                 Location/Qualifiers
source                  1..24
                        mol_type = other DNA
                        organism = Synthetic construct
SEQUENCE: 113
atatattgga cttgtattcc aagc                                              24

SEQ ID NO: 114          moltype = DNA   length = 24
FEATURE                 Location/Qualifiers
source                  1..24
                        mol_type = other DNA
                        organism = Synthetic construct
SEQUENCE: 114
cttggaatac aagtccaata tata                                              24
```

```
SEQ ID NO: 115         moltype = DNA  length = 24
FEATURE                Location/Qualifiers
source                 1..24
                       mol_type = other DNA
                       organism = Synthetic construct
SEQUENCE: 115
gtccttatag atttggacac ttat                                            24

SEQ ID NO: 116         moltype = DNA  length = 24
FEATURE                Location/Qualifiers
source                 1..24
                       mol_type = other DNA
                       organism = Synthetic construct
SEQUENCE: 116
taagtgtcca aatctataag gact                                            24

SEQ ID NO: 117         moltype = DNA  length = 24
FEATURE                Location/Qualifiers
source                 1..24
                       mol_type = other DNA
                       organism = Synthetic construct
SEQUENCE: 117
caaatcttct tgcctaagca aatt                                            24

SEQ ID NO: 118         moltype = DNA  length = 24
FEATURE                Location/Qualifiers
source                 1..24
                       mol_type = other DNA
                       organism = Synthetic construct
SEQUENCE: 118
atttgcttag gcaagaagat ttgt                                            24

SEQ ID NO: 119         moltype = DNA  length = 24
FEATURE                Location/Qualifiers
source                 1..24
                       mol_type = other DNA
                       organism = Synthetic construct
SEQUENCE: 119
ctaaactcta ttttatactc cctc                                            24

SEQ ID NO: 120         moltype = DNA  length = 24
FEATURE                Location/Qualifiers
source                 1..24
                       mol_type = other DNA
                       organism = Synthetic construct
SEQUENCE: 120
agggagtata aaatagagtt tagt                                            24

SEQ ID NO: 121         moltype = DNA  length = 24
FEATURE                Location/Qualifiers
source                 1..24
                       mol_type = other DNA
                       organism = Synthetic construct
SEQUENCE: 121
agtgttcatt ttggctcctc attt                                            24

SEQ ID NO: 122         moltype = DNA  length = 24
FEATURE                Location/Qualifiers
source                 1..24
                       mol_type = other DNA
                       organism = Synthetic construct
SEQUENCE: 122
aatgaggagc caaaatgaac acta                                            24

SEQ ID NO: 123         moltype = DNA  length = 24
FEATURE                Location/Qualifiers
source                 1..24
                       mol_type = other DNA
                       organism = Synthetic construct
SEQUENCE: 123
tcagatggat gaaaatgaat ctag                                            24

SEQ ID NO: 124         moltype = DNA  length = 24
FEATURE                Location/Qualifiers
source                 1..24
                       mol_type = other DNA
                       organism = Synthetic construct
SEQUENCE: 124
tagattcatt ttcatccatc tgaa                                            24
```

```
SEQ ID NO: 125            moltype = DNA  length = 24
FEATURE                   Location/Qualifiers
source                    1..24
                          mol_type = other DNA
                          organism = Synthetic construct
SEQUENCE: 125
tgaatccact gatatgttaa aacg                                              24

SEQ ID NO: 126            moltype = DNA  length = 24
FEATURE                   Location/Qualifiers
source                    1..24
                          mol_type = other DNA
                          organism = Synthetic construct
SEQUENCE: 126
gttttaacat atcagtggat tcat                                              24

SEQ ID NO: 127            moltype = DNA  length = 24
FEATURE                   Location/Qualifiers
source                    1..24
                          mol_type = other DNA
                          organism = Synthetic construct
SEQUENCE: 127
gggacggaga gagtatattc caag                                              24

SEQ ID NO: 128            moltype = DNA  length = 24
FEATURE                   Location/Qualifiers
source                    1..24
                          mol_type = other DNA
                          organism = Synthetic construct
SEQUENCE: 128
ttggaatata ctctctccgt ccca                                              24

SEQ ID NO: 129            moltype = DNA  length = 24
FEATURE                   Location/Qualifiers
source                    1..24
                          mol_type = other DNA
                          organism = Synthetic construct
SEQUENCE: 129
ctatctttgg gttttcatct tttt                                              24

SEQ ID NO: 130            moltype = DNA  length = 24
FEATURE                   Location/Qualifiers
source                    1..24
                          mol_type = other DNA
                          organism = Synthetic construct
SEQUENCE: 130
aaaagatgaa aacccaaaga tagc                                              24

SEQ ID NO: 131            moltype = DNA  length = 24
FEATURE                   Location/Qualifiers
source                    1..24
                          mol_type = other DNA
                          organism = Synthetic construct
SEQUENCE: 131
gaccaggagg gactctattt atat                                              24

SEQ ID NO: 132            moltype = DNA  length = 24
FEATURE                   Location/Qualifiers
source                    1..24
                          mol_type = other DNA
                          organism = Synthetic construct
SEQUENCE: 132
tataaataga gtccctcctg gtca                                              24

SEQ ID NO: 133            moltype = DNA  length = 24
FEATURE                   Location/Qualifiers
source                    1..24
                          mol_type = other DNA
                          organism = Synthetic construct
SEQUENCE: 133
gataataaag actctgacta atag                                              24

SEQ ID NO: 134            moltype = DNA  length = 24
FEATURE                   Location/Qualifiers
source                    1..24
                          mol_type = other DNA
                          organism = Synthetic construct
SEQUENCE: 134
```

```
tattagtcag agtctttatt atcg                                             24

SEQ ID NO: 135         moltype = DNA   length = 24
FEATURE                Location/Qualifiers
source                 1..24
                       mol_type = other DNA
                       organism = Synthetic construct SEQUENCE: 135
agactctgac taataggacc gagc                                             24

SEQ ID NO: 136         moltype = DNA   length = 24
FEATURE                Location/Qualifiers
source                 1..24
                       mol_type = other DNA
                       organism = Synthetic construct SEQUENCE: 136
ctcggtccta ttagtcagag tctt                                             24

SEQ ID NO: 137         moltype = DNA   length = 24
FEATURE                Location/Qualifiers
source                 1..24
                       mol_type = other DNA
                       organism = Synthetic construct SEQUENCE: 137
actaatagga ccgagcaact cgga                                             24

SEQ ID NO: 138         moltype = DNA   length = 24
FEATURE                Location/Qualifiers
source                 1..24
                       mol_type = other DNA
                       organism = Synthetic construct SEQUENCE: 138
ccgagttgct cggtcctatt agtc                                             24

SEQ ID NO: 139         moltype = DNA   length = 24
FEATURE                Location/Qualifiers
source                 1..24
                       mol_type = other DNA
                       organism = Synthetic construct SEQUENCE: 139
gaccgagcaa ctcggattcg gtgg                                             24

SEQ ID NO: 140         moltype = DNA   length = 24
FEATURE                Location/Qualifiers
source                 1..24
                       mol_type = other DNA
                       organism = Synthetic construct SEQUENCE: 140
caccgaatcc gagttgctcg gtcc                                             24

SEQ ID NO: 141         moltype = DNA   length = 24
FEATURE                Location/Qualifiers
source                 1..24
                       mol_type = other DNA
                       organism = Synthetic construct SEQUENCE: 141
aactcggatt cggtggagtg actc                                             24

SEQ ID NO: 142         moltype = DNA   length = 24
FEATURE                Location/Qualifiers
source                 1..24
                       mol_type = other DNA
                       organism = Synthetic construct SEQUENCE: 142
agtcactcca ccgaatccga gttg                                             24

SEQ ID NO: 143         moltype = DNA   length = 24
FEATURE                Location/Qualifiers
source                 1..24
                       mol_type = other DNA
                       organism = Synthetic construct SEQUENCE: 143
ttcggtggag tgactcggac ttgg                                             24

SEQ ID NO: 144         moltype = DNA   length = 24
FEATURE                Location/Qualifiers
source                 1..24
                       mol_type = other DNA
                       organism = Synthetic construct
```

```
SEQUENCE: 144
caagtccgag tcactccacc gaat                                              24

SEQ ID NO: 145          moltype = DNA   length = 24
FEATURE                 Location/Qualifiers
source                  1..24
                        mol_type = other DNA
                        organism = Synthetic construct
SEQUENCE: 145
agtgactcgg acttggactg tgca                                              24

SEQ ID NO: 146          moltype = DNA   length = 24
FEATURE                 Location/Qualifiers
source                  1..24
                        mol_type = other DNA
                        organism = Synthetic construct
SEQUENCE: 146
gcacagtcca agtccgagtc actc                                              24

SEQ ID NO: 147          moltype = DNA   length = 24
FEATURE                 Location/Qualifiers
source                  1..24
                        mol_type = other DNA
                        organism = Synthetic construct
SEQUENCE: 147
ggacttggac tgtgcaactc ggat                                              24

SEQ ID NO: 148          moltype = DNA   length = 24
FEATURE                 Location/Qualifiers
source                  1..24
                        mol_type = other DNA
                        organism = Synthetic construct
SEQUENCE: 148
tccgagttgc acagtccaag tccg                                              24

SEQ ID NO: 149          moltype = DNA   length = 24
FEATURE                 Location/Qualifiers
source                  1..24
                        mol_type = other DNA
                        organism = Synthetic construct
SEQUENCE: 149
actgtgcaac tcggattcag ccgg                                              24

SEQ ID NO: 150          moltype = DNA   length = 24
FEATURE                 Location/Qualifiers
source                  1..24
                        mol_type = other DNA
                        organism = Synthetic construct
SEQUENCE: 150
cggctgaatc cgagttgcac agtc                                              24

SEQ ID NO: 151          moltype = DNA   length = 24
FEATURE                 Location/Qualifiers
source                  1..24
                        mol_type = other DNA
                        organism = Synthetic construct
SEQUENCE: 151
actcggattc agccgggata ctca                                              24

SEQ ID NO: 152          moltype = DNA   length = 24
FEATURE                 Location/Qualifiers
source                  1..24
                        mol_type = other DNA
                        organism = Synthetic construct
SEQUENCE: 152
gagtatcccg gctgaatccg agtt                                              24

SEQ ID NO: 153          moltype = DNA   length = 24
FEATURE                 Location/Qualifiers
source                  1..24
                        mol_type = other DNA
                        organism = Synthetic construct
SEQUENCE: 153
tcagccggga tactcaaaat cgaa                                              24

SEQ ID NO: 154          moltype = DNA   length = 24
FEATURE                 Location/Qualifiers
source                  1..24
                        mol_type = other DNA
```

```
                        organism = Synthetic construct
SEQUENCE: 154
tcgattttga gtatcccggc tgaa                                              24

SEQ ID NO: 155          moltype = DNA   length = 24
FEATURE                 Location/Qualifiers
source                  1..24
                        mol_type = other DNA
                        organism = Synthetic construct
SEQUENCE: 155
gatactcaaa atcgaaatcc aagg                                              24

SEQ ID NO: 156          moltype = DNA   length = 24
FEATURE                 Location/Qualifiers
source                  1..24
                        mol_type = other DNA
                        organism = Synthetic construct
SEQUENCE: 156
cttggatttc gattttgagt atcc                                              24

SEQ ID NO: 157          moltype = DNA   length = 24
FEATURE                 Location/Qualifiers
source                  1..24
                        mol_type = other DNA
                        organism = Synthetic construct
SEQUENCE: 157
aaatcgaaat ccaagggact cggt                                              24

SEQ ID NO: 158          moltype = DNA   length = 24
FEATURE                 Location/Qualifiers
source                  1..24
                        mol_type = other DNA
                        organism = Synthetic construct
SEQUENCE: 158
ccgagtccct tggatttcga tttt                                              24

SEQ ID NO: 159          moltype = DNA   length = 24
FEATURE                 Location/Qualifiers
source                  1..24
                        mol_type = other DNA
                        organism = Synthetic construct
SEQUENCE: 159
atccaaggga ctcggtccat aggt                                              24

SEQ ID NO: 160          moltype = DNA   length = 24
FEATURE                 Location/Qualifiers
source                  1..24
                        mol_type = other DNA
                        organism = Synthetic construct
SEQUENCE: 160
cctatggacc gagtcccttg gatt                                              24

SEQ ID NO: 161          moltype = DNA   length = 24
FEATURE                 Location/Qualifiers
source                  1..24
                        mol_type = other DNA
                        organism = Synthetic construct
SEQUENCE: 161
gactcggtcc ataggttaat actc                                              24

SEQ ID NO: 162          moltype = DNA   length = 24
FEATURE                 Location/Qualifiers
source                  1..24
                        mol_type = other DNA
                        organism = Synthetic construct
SEQUENCE: 162
agtattaacc tatggaccga gtcc                                              24

SEQ ID NO: 163          moltype = DNA   length = 24
FEATURE                 Location/Qualifiers
source                  1..24
                        mol_type = other DNA
                        organism = Synthetic construct
SEQUENCE: 163
tcatatttta catctaaacg ttcg                                              24

SEQ ID NO: 164          moltype = DNA   length = 24
FEATURE                 Location/Qualifiers
source                  1..24
```

```
                        mol_type = other DNA
                        organism = Synthetic construct
SEQUENCE: 164
gaacgtttag atgtaaaata tgag                                              24

SEQ ID NO: 165          moltype = DNA  length = 24
FEATURE                 Location/Qualifiers
source                  1..24
                        mol_type = other DNA
                        organism = Synthetic construct
SEQUENCE: 165
tacatctaaa cgttcgatgt gcgt                                              24

SEQ ID NO: 166          moltype = DNA  length = 24
FEATURE                 Location/Qualifiers
source                  1..24
                        mol_type = other DNA
                        organism = Synthetic construct
SEQUENCE: 166
cgcacatcga acgtttagat gtaa                                              24

SEQ ID NO: 167          moltype = DNA  length = 24
FEATURE                 Location/Qualifiers
source                  1..24
                        mol_type = other DNA
                        organism = Synthetic construct
SEQUENCE: 167
aacgttcgat gtgcgtggaa gcaa                                              24

SEQ ID NO: 168          moltype = DNA  length = 24
FEATURE                 Location/Qualifiers
source                  1..24
                        mol_type = other DNA
                        organism = Synthetic construct
SEQUENCE: 168
tgcttccacg cacatcgaac gttt                                              24

SEQ ID NO: 169          moltype = DNA  length = 24
FEATURE                 Location/Qualifiers
source                  1..24
                        mol_type = other DNA
                        organism = Synthetic construct
SEQUENCE: 169
atgtgcgtgg aagcaaacac cccc                                              24

SEQ ID NO: 170          moltype = DNA  length = 24
FEATURE                 Location/Qualifiers
source                  1..24
                        mol_type = other DNA
                        organism = Synthetic construct
SEQUENCE: 170
ggggtgtttg cttccacgca catc                                              24

SEQ ID NO: 171          moltype = DNA  length = 24
FEATURE                 Location/Qualifiers
source                  1..24
                        mol_type = other DNA
                        organism = Synthetic construct
SEQUENCE: 171
ggaagcaaac accccttag acgt                                               24

SEQ ID NO: 172          moltype = DNA  length = 24
FEATURE                 Location/Qualifiers
source                  1..24
                        mol_type = other DNA
                        organism = Synthetic construct
SEQUENCE: 172
cgtctaaggg ggtgtttgct tcca                                              24

SEQ ID NO: 173          moltype = DNA  length = 24
FEATURE                 Location/Qualifiers
source                  1..24
                        mol_type = other DNA
                        organism = Synthetic construct
SEQUENCE: 173
acaccccctt agacgtggga cacc                                              24

SEQ ID NO: 174          moltype = DNA  length = 24
FEATURE                 Location/Qualifiers
```

```
source                       1..24
                             mol_type = other DNA
                             organism = Synthetic construct
SEQUENCE: 174
gtgtcccacg tctaaggggg tgtt                                              24

SEQ ID NO: 175               moltype = DNA   length = 24
FEATURE                      Location/Qualifiers
source                       1..24
                             mol_type = other DNA
                             organism = Synthetic construct
SEQUENCE: 175
ttagacgtgg gacaccacct cttg                                              24

SEQ ID NO: 176               moltype = DNA   length = 24
FEATURE                      Location/Qualifiers
source                       1..24
                             mol_type = other DNA
                             organism = Synthetic construct
SEQUENCE: 176
aagaggtggt gtcccacgtc taag                                              24

SEQ ID NO: 177               moltype = DNA   length = 24
FEATURE                      Location/Qualifiers
source                       1..24
                             mol_type = other DNA
                             organism = Synthetic construct
SEQUENCE: 177
gggacaccac ctcttgtcga ccat                                              24

SEQ ID NO: 178               moltype = DNA   length = 24
FEATURE                      Location/Qualifiers
source                       1..24
                             mol_type = other DNA
                             organism = Synthetic construct
SEQUENCE: 178
tggtcgacaa gaggtggtgt ccca                                              24

SEQ ID NO: 179               moltype = DNA   length = 24
FEATURE                      Location/Qualifiers
source                       1..24
                             mol_type = other DNA
                             organism = Synthetic construct
SEQUENCE: 179
acctcttgtc gaccatttgt agcc                                              24

SEQ ID NO: 180               moltype = DNA   length = 24
FEATURE                      Location/Qualifiers
source                       1..24
                             mol_type = other DNA
                             organism = Synthetic construct
SEQUENCE: 180
gctacaaatg gtcgacaaga ggtg                                              24

SEQ ID NO: 181               moltype = DNA   length = 24
FEATURE                      Location/Qualifiers
source                       1..24
                             mol_type = other DNA
                             organism = Synthetic construct
SEQUENCE: 181
tcgaccattt gtagccttct tcat                                              24

SEQ ID NO: 182               moltype = DNA   length = 24
FEATURE                      Location/Qualifiers
source                       1..24
                             mol_type = other DNA
                             organism = Synthetic construct
SEQUENCE: 182
tgaagaaggc tacaaatggt cgac                                              24

SEQ ID NO: 183               moltype = DNA   length = 24
FEATURE                      Location/Qualifiers
source                       1..24
                             mol_type = other DNA
                             organism = Synthetic construct
SEQUENCE: 183
ttgtagcctt cttcatgttc cgtt                                              24

SEQ ID NO: 184               moltype = DNA   length = 24
```

```
FEATURE                 Location/Qualifiers
source                  1..24
                        mol_type = other DNA
                        organism = Synthetic construct
SEQUENCE: 184
acggaacatg aagaaggcta caaa                                              24

SEQ ID NO: 185          moltype = DNA   length = 24
FEATURE                 Location/Qualifiers
source                  1..24
                        mol_type = other DNA
                        organism = Synthetic construct
SEQUENCE: 185
ttcttcatgt tccgttctgc cgac                                              24

SEQ ID NO: 186          moltype = DNA   length = 24
FEATURE                 Location/Qualifiers
source                  1..24
                        mol_type = other DNA
                        organism = Synthetic construct
SEQUENCE: 186
tcggcagaac ggaacatgaa gaag                                              24

SEQ ID NO: 187          moltype = DNA   length = 24
FEATURE                 Location/Qualifiers
source                  1..24
                        mol_type = other DNA
                        organism = Synthetic construct
SEQUENCE: 187
gttccgttct gccgactgat ggat                                              24

SEQ ID NO: 188          moltype = DNA   length = 24
FEATURE                 Location/Qualifiers
source                  1..24
                        mol_type = other DNA
                        organism = Synthetic construct
SEQUENCE: 188
tccatcagtc ggcagaacgg aaca                                              24

SEQ ID NO: 189          moltype = DNA   length = 24
FEATURE                 Location/Qualifiers
source                  1..24
                        mol_type = other DNA
                        organism = Synthetic construct
SEQUENCE: 189
ctgccgactg atggatcact cctg                                              24

SEQ ID NO: 190          moltype = DNA   length = 24
FEATURE                 Location/Qualifiers
source                  1..24
                        mol_type = other DNA
                        organism = Synthetic construct
SEQUENCE: 190
aggagtgatc catcagtcgg caga                                              24

SEQ ID NO: 191          moltype = DNA   length = 24
FEATURE                 Location/Qualifiers
source                  1..24
                        mol_type = other DNA
                        organism = Synthetic construct
SEQUENCE: 191
tgatggatca ctcctgcagc tgca                                              24

SEQ ID NO: 192          moltype = DNA   length = 24
FEATURE                 Location/Qualifiers
source                  1..24
                        mol_type = other DNA
                        organism = Synthetic construct
SEQUENCE: 192
gcagctgcag gagtgatcca tcag                                              24

SEQ ID NO: 193          moltype = DNA   length = 24
FEATURE                 Location/Qualifiers
source                  1..24
                        mol_type = other DNA
                        organism = Synthetic construct
SEQUENCE: 193
cactcctgca gctgcagctg cagt                                              24
```

```
SEQ ID NO: 194          moltype = DNA  length = 24
FEATURE                 Location/Qualifiers
source                  1..24
                        mol_type = other DNA
                        organism = Synthetic construct
SEQUENCE: 194
ctgcagctgc agctgcagga gtga                                              24

SEQ ID NO: 195          moltype = DNA  length = 24
FEATURE                 Location/Qualifiers
source                  1..24
                        mol_type = other DNA
                        organism = Synthetic construct
SEQUENCE: 195
atgaagcaaa actctaaagt tgac                                              24

SEQ ID NO: 196          moltype = DNA  length = 24
FEATURE                 Location/Qualifiers
source                  1..24
                        mol_type = other DNA
                        organism = Synthetic construct
SEQUENCE: 196
tcaactttag agttttgctt cata                                              24

SEQ ID NO: 197          moltype = DNA  length = 24
FEATURE                 Location/Qualifiers
source                  1..24
                        mol_type = other DNA
                        organism = Synthetic construct
SEQUENCE: 197
aacccagttt ttcagctctc acta                                              24

SEQ ID NO: 198          moltype = DNA  length = 24
FEATURE                 Location/Qualifiers
source                  1..24
                        mol_type = other DNA
                        organism = Synthetic construct
SEQUENCE: 198
agtgagagct gaaaaactgg gttg                                              24

SEQ ID NO: 199          moltype = DNA  length = 24
FEATURE                 Location/Qualifiers
source                  1..24
                        mol_type = other DNA
                        organism = Synthetic construct
SEQUENCE: 199
attaccaatt gatcatcatc ttgc                                              24

SEQ ID NO: 200          moltype = DNA  length = 24
FEATURE                 Location/Qualifiers
source                  1..24
                        mol_type = other DNA
                        organism = Synthetic construct
SEQUENCE: 200
caagatgatg atcaattggt aatt                                              24

SEQ ID NO: 201          moltype = DNA  length = 24
FEATURE                 Location/Qualifiers
source                  1..24
                        mol_type = other DNA
                        organism = Synthetic construct
SEQUENCE: 201
attacaactt tccagctatt ttgc                                              24

SEQ ID NO: 202          moltype = DNA  length = 24
FEATURE                 Location/Qualifiers
source                  1..24
                        mol_type = other DNA
                        organism = Synthetic construct
SEQUENCE: 202
caaaatagct ggaaagttgt aata                                              24

SEQ ID NO: 203          moltype = DNA  length = 24
FEATURE                 Location/Qualifiers
source                  1..24
                        mol_type = other DNA
                        organism = Synthetic construct
SEQUENCE: 203
cactttataa tcctaatcct acac                                              24
```

```
SEQ ID NO: 204          moltype = DNA  length = 24
FEATURE                 Location/Qualifiers
source                  1..24
                        mol_type = other DNA
                        organism = Synthetic construct
SEQUENCE: 204
tgtaggatta ggattataaa gtgt                                              24

SEQ ID NO: 205          moltype = DNA  length = 24
FEATURE                 Location/Qualifiers
source                  1..24
                        mol_type = other DNA
                        organism = Synthetic construct
SEQUENCE: 205
aagctcattc aacaacacaa ttag                                              24

SEQ ID NO: 206          moltype = DNA  length = 24
FEATURE                 Location/Qualifiers
source                  1..24
                        mol_type = other DNA
                        organism = Synthetic construct
SEQUENCE: 206
taattgtgtt gttgaatgag cttt                                              24

SEQ ID NO: 207          moltype = DNA  length = 24
FEATURE                 Location/Qualifiers
source                  1..24
                        mol_type = other DNA
                        organism = Synthetic construct
SEQUENCE: 207
tcaaacacaa aatagagtta tggc                                              24

SEQ ID NO: 208          moltype = DNA  length = 24
FEATURE                 Location/Qualifiers
source                  1..24
                        mol_type = other DNA
                        organism = Synthetic construct
SEQUENCE: 208
ccataactct attttgtgtt tgat                                              24

SEQ ID NO: 209          moltype = DNA  length = 24
FEATURE                 Location/Qualifiers
source                  1..24
                        mol_type = other DNA
                        organism = Synthetic construct
SEQUENCE: 209
ttaacttcat gtactaccat ttcc                                              24

SEQ ID NO: 210          moltype = DNA  length = 24
FEATURE                 Location/Qualifiers
source                  1..24
                        mol_type = other DNA
                        organism = Synthetic construct
SEQUENCE: 210
gaaatggtag tacatgaagt taaa                                              24

SEQ ID NO: 211          moltype = DNA  length = 24
FEATURE                 Location/Qualifiers
source                  1..24
                        mol_type = other DNA
                        organism = Synthetic construct
SEQUENCE: 211
catccaaaat tttcgtccgt ccaa                                              24

SEQ ID NO: 212          moltype = DNA  length = 24
FEATURE                 Location/Qualifiers
source                  1..24
                        mol_type = other DNA
                        organism = Synthetic construct
SEQUENCE: 212
tggacggacg aaaattttgg atgg                                              24

SEQ ID NO: 213          moltype = DNA  length = 24
FEATURE                 Location/Qualifiers
source                  1..24
                        mol_type = other DNA
                        organism = Synthetic construct
SEQUENCE: 213
```

```
cgataactttaaggtgaattgtga                                             24

SEQ ID NO: 214          moltype = DNA  length = 24
FEATURE                 Location/Qualifiers
source                  1..24
                        mol_type = other DNA
                        organism = Synthetic construct SEQUENCE: 214
cacaattcaccttaaagttatcga                                             24

SEQ ID NO: 215          moltype = DNA  length = 24
FEATURE                 Location/Qualifiers
source                  1..24
                        mol_type = other DNA
                        organism = Synthetic construct SEQUENCE: 215
taatgaaggaaaatctttcagg                                               24

SEQ ID NO: 216          moltype = DNA  length = 24
FEATURE                 Location/Qualifiers
source                  1..24
                        mol_type = other DNA
                        organism = Synthetic construct SEQUENCE: 216
ctggaaaagattttccttcattat                                             24

SEQ ID NO: 217          moltype = DNA  length = 24
FEATURE                 Location/Qualifiers
source                  1..24
                        mol_type = other DNA
                        organism = Synthetic construct SEQUENCE: 217
gatagacgaaatgtcctccttggt                                             24

SEQ ID NO: 218          moltype = DNA  length = 24
FEATURE                 Location/Qualifiers
source                  1..24
                        mol_type = other DNA
                        organism = Synthetic construct SEQUENCE: 218
ccaaggaggacatttcgtctatca                                             24

SEQ ID NO: 219          moltype = DNA  length = 24
FEATURE                 Location/Qualifiers
source                  1..24
                        mol_type = other DNA
                        organism = Synthetic construct SEQUENCE: 219
ggctctatggagcatctaatctta                                             24

SEQ ID NO: 220          moltype = DNA  length = 24
FEATURE                 Location/Qualifiers
source                  1..24
                        mol_type = other DNA
                        organism = Synthetic construct SEQUENCE: 220
aagattagatgctccatagagccc                                             24

SEQ ID NO: 221          moltype = DNA  length = 24
FEATURE                 Location/Qualifiers
source                  1..24
                        mol_type = other DNA
                        organism = Synthetic construct SEQUENCE: 221
aaccaacgagccatttgccctagg                                             24

SEQ ID NO: 222          moltype = DNA  length = 24
FEATURE                 Location/Qualifiers
source                  1..24
                        mol_type = other DNA
                        organism = Synthetic construct SEQUENCE: 222
ctagggcaaatggctcgttggtta                                             24

SEQ ID NO: 223          moltype = DNA  length = 24
FEATURE                 Location/Qualifiers
source                  1..24
                        mol_type = other DNA
                        organism = Synthetic construct
```

```
SEQUENCE: 223
gtaccacccc cagacttctc aaca                                        24

SEQ ID NO: 224         moltype = DNA   length = 24
FEATURE                Location/Qualifiers
source                 1..24
                       mol_type = other DNA
                       organism = Synthetic construct
SEQUENCE: 224
gttgagaagt ctggggtgg tacc                                         24

SEQ ID NO: 225         moltype = DNA   length = 24
FEATURE                Location/Qualifiers
source                 1..24
                       mol_type = other DNA
                       organism = Synthetic construct
SEQUENCE: 225
tctgtcaacc gacccaaccg accc                                        24

SEQ ID NO: 226         moltype = DNA   length = 24
FEATURE                Location/Qualifiers
source                 1..24
                       mol_type = other DNA
                       organism = Synthetic construct
SEQUENCE: 226
ggtcggttgg gtcggttgac agaa                                        24

SEQ ID NO: 227         moltype = DNA   length = 24
FEATURE                Location/Qualifiers
source                 1..24
                       mol_type = other DNA
                       organism = Synthetic construct
SEQUENCE: 227
tccagactgt aagttatttt tctg                                        24

SEQ ID NO: 228         moltype = DNA   length = 24
FEATURE                Location/Qualifiers
source                 1..24
                       mol_type = other DNA
                       organism = Synthetic construct
SEQUENCE: 228
agaaaaataa cttacagtct ggat                                        24

SEQ ID NO: 229         moltype = DNA   length = 24
FEATURE                Location/Qualifiers
source                 1..24
                       mol_type = other DNA
                       organism = Synthetic construct
SEQUENCE: 229
cagagcttct aagaacaaaa actt                                        24

SEQ ID NO: 230         moltype = DNA   length = 24
FEATURE                Location/Qualifiers
source                 1..24
                       mol_type = other DNA
                       organism = Synthetic construct
SEQUENCE: 230
agttttgtt cttagaagct ctgt                                         24

SEQ ID NO: 231         moltype = DNA   length = 24
FEATURE                Location/Qualifiers
source                 1..24
                       mol_type = other DNA
                       organism = Synthetic construct
SEQUENCE: 231
gtatggctgc tatacaaaat tccc                                        24

SEQ ID NO: 232         moltype = DNA   length = 24
FEATURE                Location/Qualifiers
source                 1..24
                       mol_type = other DNA
                       organism = Synthetic construct
SEQUENCE: 232
ggaattttgt atagcagcca taca                                        24

SEQ ID NO: 233         moltype = DNA   length = 24
FEATURE                Location/Qualifiers
source                 1..24
                       mol_type = other DNA
```

-continued

```
                        organism = Synthetic construct
SEQUENCE: 233
cgcttcctgg aataattgat atgg                                              24

SEQ ID NO: 234          moltype = DNA   length = 24
FEATURE                 Location/Qualifiers
source                  1..24
                        mol_type = other DNA
                        organism = Synthetic construct
SEQUENCE: 234
catatcaatt attccaggaa gcgg                                              24

SEQ ID NO: 235          moltype = DNA   length = 24
FEATURE                 Location/Qualifiers
source                  1..24
                        mol_type = other DNA
                        organism = Synthetic construct
SEQUENCE: 235
tattatataa ggcaaggtat agcc                                              24

SEQ ID NO: 236          moltype = DNA   length = 24
FEATURE                 Location/Qualifiers
source                  1..24
                        mol_type = other DNA
                        organism = Synthetic construct
SEQUENCE: 236
gctatacctt gccttatata ataa                                              24

SEQ ID NO: 237          moltype = DNA   length = 24
FEATURE                 Location/Qualifiers
source                  1..24
                        mol_type = other DNA
                        organism = Synthetic construct
SEQUENCE: 237
tcattcaaaa cctagcaata atgg                                              24

SEQ ID NO: 238          moltype = DNA   length = 24
FEATURE                 Location/Qualifiers
source                  1..24
                        mol_type = other DNA
                        organism = Synthetic construct
SEQUENCE: 238
cattattgct aggttttgaa tgaa                                              24

SEQ ID NO: 239          moltype = DNA   length = 24
FEATURE                 Location/Qualifiers
source                  1..24
                        mol_type = other DNA
                        organism = Synthetic construct
SEQUENCE: 239
gtagtaatac atctctcaaa actc                                              24

SEQ ID NO: 240          moltype = DNA   length = 24
FEATURE                 Location/Qualifiers
source                  1..24
                        mol_type = other DNA
                        organism = Synthetic construct
SEQUENCE: 240
agttttgaga gatgtattac tact                                              24

SEQ ID NO: 241          moltype = DNA   length = 24
FEATURE                 Location/Qualifiers
source                  1..24
                        mol_type = other DNA
                        organism = Synthetic construct
SEQUENCE: 241
ttcttcctcc acttctttat cttc                                              24

SEQ ID NO: 242          moltype = DNA   length = 24
FEATURE                 Location/Qualifiers
source                  1..24
                        mol_type = other DNA
                        organism = Synthetic construct
SEQUENCE: 242
aagataaaga agtggaggaa gaag                                              24

SEQ ID NO: 243          moltype = DNA   length = 24
FEATURE                 Location/Qualifiers
source                  1..24
```

```
                        mol_type = other DNA
                        organism = Synthetic construct
SEQUENCE: 243
aagccctctt caacttttca tcca                                              24

SEQ ID NO: 244          moltype = DNA   length = 24
FEATURE                 Location/Qualifiers
source                  1..24
                        mol_type = other DNA
                        organism = Synthetic construct
SEQUENCE: 244
ggatgaaaag ttgaagaggg ctta                                              24

SEQ ID NO: 245          moltype = DNA   length = 24
FEATURE                 Location/Qualifiers
source                  1..24
                        mol_type = other DNA
                        organism = Synthetic construct
SEQUENCE: 245
cgtaccaaat gttcaaagtt tcat                                              24

SEQ ID NO: 246          moltype = DNA   length = 24
FEATURE                 Location/Qualifiers
source                  1..24
                        mol_type = other DNA
                        organism = Synthetic construct
SEQUENCE: 246
tgaaactttg aacatttggt acgt                                              24

SEQ ID NO: 247          moltype = DNA   length = 24
FEATURE                 Location/Qualifiers
source                  1..24
                        mol_type = other DNA
                        organism = Synthetic construct
SEQUENCE: 247
taccaataat aacggtgacc aaaa                                              24

SEQ ID NO: 248          moltype = DNA   length = 24
FEATURE                 Location/Qualifiers
source                  1..24
                        mol_type = other DNA
                        organism = Synthetic construct
SEQUENCE: 248
tttggtcacc gttattattg gtaa                                              24

SEQ ID NO: 249          moltype = DNA   length = 24
FEATURE                 Location/Qualifiers
source                  1..24
                        mol_type = other DNA
                        organism = Synthetic construct
SEQUENCE: 249
gttgaaacga attctgttga tcga                                              24

SEQ ID NO: 250          moltype = DNA   length = 24
FEATURE                 Location/Qualifiers
source                  1..24
                        mol_type = other DNA
                        organism = Synthetic construct
SEQUENCE: 250
cgatcaacag aattcgtttc aacg                                              24

SEQ ID NO: 251          moltype = DNA   length = 24
FEATURE                 Location/Qualifiers
source                  1..24
                        mol_type = other DNA
                        organism = Synthetic construct
SEQUENCE: 251
ttcttcttgg cttaggtggt cttt                                              24

SEQ ID NO: 252          moltype = DNA   length = 24
FEATURE                 Location/Qualifiers
source                  1..24
                        mol_type = other DNA
                        organism = Synthetic construct
SEQUENCE: 252
aagaccacct aagccaagaa gaac                                              24

SEQ ID NO: 253          moltype = DNA   length = 24
FEATURE                 Location/Qualifiers
```

-continued

```
source                  1..24
                        mol_type = other DNA
                        organism = Synthetic construct
SEQUENCE: 253
tgctaatgct ataccattag ctgc                                              24

SEQ ID NO: 254          moltype = DNA   length = 24
FEATURE                 Location/Qualifiers
source                  1..24
                        mol_type = other DNA
                        organism = Synthetic construct
SEQUENCE: 254
cagctaatgg tatagcatta gcaa                                              24

SEQ ID NO: 255          moltype = DNA   length = 24
FEATURE                 Location/Qualifiers
source                  1..24
                        mol_type = other DNA
                        organism = Synthetic construct
SEQUENCE: 255
aattatcaat gcttgtgaat ctcg                                              24

SEQ ID NO: 256          moltype = DNA   length = 24
FEATURE                 Location/Qualifiers
source                  1..24
                        mol_type = other DNA
                        organism = Synthetic construct
SEQUENCE: 256
gagattcaca agcattgata attt                                              24

SEQ ID NO: 257          moltype = DNA   length = 24
FEATURE                 Location/Qualifiers
source                  1..24
                        mol_type = other DNA
                        organism = Synthetic construct
SEQUENCE: 257
tgttaaaaaa tttcctcacc tacc                                              24

SEQ ID NO: 258          moltype = DNA   length = 24
FEATURE                 Location/Qualifiers
source                  1..24
                        mol_type = other DNA
                        organism = Synthetic construct
SEQUENCE: 258
gtaggtgagg aaattttta acaa                                               24

SEQ ID NO: 259          moltype = DNA   length = 24
FEATURE                 Location/Qualifiers
source                  1..24
                        mol_type = other DNA
                        organism = Synthetic construct
SEQUENCE: 259
gaattgttcg atatgagatc gagc                                              24

SEQ ID NO: 260          moltype = DNA   length = 24
FEATURE                 Location/Qualifiers
source                  1..24
                        mol_type = other DNA
                        organism = Synthetic construct
SEQUENCE: 260
ctcgatctca tatcgaacaa ttcg                                              24

SEQ ID NO: 261          moltype = DNA   length = 24
FEATURE                 Location/Qualifiers
source                  1..24
                        mol_type = other DNA
                        organism = Synthetic construct
SEQUENCE: 261
tggagtaata ttttatttgg ctcc                                              24

SEQ ID NO: 262          moltype = DNA   length = 24
FEATURE                 Location/Qualifiers
source                  1..24
                        mol_type = other DNA
                        organism = Synthetic construct
SEQUENCE: 262
gagccaaata aaatattact ccat                                              24

SEQ ID NO: 263          moltype = DNA   length = 24
```

```
FEATURE                 Location/Qualifiers
source                  1..24
                        mol_type = other DNA
                        organism = Synthetic construct
SEQUENCE: 263
tatataaggc aatgtatagc ccta                                          24

SEQ ID NO: 264          moltype = DNA  length = 24
FEATURE                 Location/Qualifiers
source                  1..24
                        mol_type = other DNA
                        organism = Synthetic construct
SEQUENCE: 264
agggctatac attgccttat ataa                                          24

SEQ ID NO: 265          moltype = DNA  length = 24
FEATURE                 Location/Qualifiers
source                  1..24
                        mol_type = other DNA
                        organism = Synthetic construct
SEQUENCE: 265
tcatccaaaa actagcaatg gcaa                                          24

SEQ ID NO: 266          moltype = DNA  length = 24
FEATURE                 Location/Qualifiers
source                  1..24
                        mol_type = other DNA
                        organism = Synthetic construct
SEQUENCE: 266
tgccattgct agtttttgga tgaa                                          24

SEQ ID NO: 267          moltype = DNA  length = 24
FEATURE                 Location/Qualifiers
source                  1..24
                        mol_type = other DNA
                        organism = Synthetic construct
SEQUENCE: 267
taatagtagt agtaccactc tcaa                                          24

SEQ ID NO: 268          moltype = DNA  length = 24
FEATURE                 Location/Qualifiers
source                  1..24
                        mol_type = other DNA
                        organism = Synthetic construct
SEQUENCE: 268
tgagagtggt actactacta ttac                                          24

SEQ ID NO: 269          moltype = DNA  length = 24
FEATURE                 Location/Qualifiers
source                  1..24
                        mol_type = other DNA
                        organism = Synthetic construct
SEQUENCE: 269
tttacttctt cctccacttc ttta                                          24

SEQ ID NO: 270          moltype = DNA  length = 24
FEATURE                 Location/Qualifiers
source                  1..24
                        mol_type = other DNA
                        organism = Synthetic construct
SEQUENCE: 270
aaagaagtgg aggaagaagt aaaa                                          24

SEQ ID NO: 271          moltype = DNA  length = 24
FEATURE                 Location/Qualifiers
source                  1..24
                        mol_type = other DNA
                        organism = Synthetic construct
SEQUENCE: 271
ctcctaagcc ctctcaactt ttcc                                          24

SEQ ID NO: 272          moltype = DNA  length = 24
FEATURE                 Location/Qualifiers
source                  1..24
                        mol_type = other DNA
                        organism = Synthetic construct
SEQUENCE: 272
gaaaagttga gagggcttag gagt                                          24
```

```
SEQ ID NO: 273          moltype = DNA   length = 24
FEATURE                 Location/Qualifiers
source                  1..24
                        mol_type = other DNA
                        organism = Synthetic construct
SEQUENCE: 273
acgtaacaaa acgttcaaag tttc                                              24

SEQ ID NO: 274          moltype = DNA   length = 24
FEATURE                 Location/Qualifiers
source                  1..24
                        mol_type = other DNA
                        organism = Synthetic construct
SEQUENCE: 274
aaactttgaa cgttttgtta cgtt                                              24

SEQ ID NO: 275          moltype = DNA   length = 24
FEATURE                 Location/Qualifiers
source                  1..24
                        mol_type = other DNA
                        organism = Synthetic construct
SEQUENCE: 275
gttaccaata ataacggtga ccaa                                              24

SEQ ID NO: 276          moltype = DNA   length = 24
FEATURE                 Location/Qualifiers
source                  1..24
                        mol_type = other DNA
                        organism = Synthetic construct
SEQUENCE: 276
tggtcaccgt tattattggt aacc                                              24

SEQ ID NO: 277          moltype = DNA   length = 24
FEATURE                 Location/Qualifiers
source                  1..24
                        mol_type = other DNA
                        organism = Synthetic construct
SEQUENCE: 277
acgttgaaac gaattctgtt gatc                                              24

SEQ ID NO: 278          moltype = DNA   length = 24
FEATURE                 Location/Qualifiers
source                  1..24
                        mol_type = other DNA
                        organism = Synthetic construct
SEQUENCE: 278
atcaacagaa ttcgtttcaa cgtt                                              24

SEQ ID NO: 279          moltype = DNA   length = 24
FEATURE                 Location/Qualifiers
source                  1..24
                        mol_type = other DNA
                        organism = Synthetic construct
SEQUENCE: 279
tgttcttctt ggtttaggag gtct                                              24

SEQ ID NO: 280          moltype = DNA   length = 24
FEATURE                 Location/Qualifiers
source                  1..24
                        mol_type = other DNA
                        organism = Synthetic construct
SEQUENCE: 280
gacctcctaa accaagaaga acat                                              24

SEQ ID NO: 281          moltype = DNA   length = 24
FEATURE                 Location/Qualifiers
source                  1..24
                        mol_type = other DNA
                        organism = Synthetic construct
SEQUENCE: 281
gttgctaatg ctataccatt agct                                              24

SEQ ID NO: 282          moltype = DNA   length = 24
FEATURE                 Location/Qualifiers
source                  1..24
                        mol_type = other DNA
                        organism = Synthetic construct
SEQUENCE: 282
gctaatggta tagcattagc aaca                                              24
```

```
SEQ ID NO: 283          moltype = DNA  length = 24
FEATURE                 Location/Qualifiers
source                  1..24
                        mol_type = other DNA
                        organism = Synthetic construct
SEQUENCE: 283
cttctccaac tccacctcct gatc                                              24

SEQ ID NO: 284          moltype = DNA  length = 24
FEATURE                 Location/Qualifiers
source                  1..24
                        mol_type = other DNA
                        organism = Synthetic construct
SEQUENCE: 284
atcaggaggt ggagttggag aagc                                              24

SEQ ID NO: 285          moltype = DNA  length = 24
FEATURE                 Location/Qualifiers
source                  1..24
                        mol_type = other DNA
                        organism = Synthetic construct
SEQUENCE: 285
ccaaacaatc tgttcagcta ttca                                              24

SEQ ID NO: 286          moltype = DNA  length = 24
FEATURE                 Location/Qualifiers
source                  1..24
                        mol_type = other DNA
                        organism = Synthetic construct
SEQUENCE: 286
gaatagctga acagattgtt tggt                                              24

SEQ ID NO: 287          moltype = DNA  length = 24
FEATURE                 Location/Qualifiers
source                  1..24
                        mol_type = other DNA
                        organism = Synthetic construct
SEQUENCE: 287
aaatgtgtaa aagatttccc acac                                              24

SEQ ID NO: 288          moltype = DNA  length = 24
FEATURE                 Location/Qualifiers
source                  1..24
                        mol_type = other DNA
                        organism = Synthetic construct
SEQUENCE: 288
tgtgggaaat cttttacaca tttt                                              24

SEQ ID NO: 289          moltype = DNA  length = 24
FEATURE                 Location/Qualifiers
source                  1..24
                        mol_type = other DNA
                        organism = Synthetic construct
SEQUENCE: 289
tcaaaaacct cccacctacc gcgt                                              24

SEQ ID NO: 290          moltype = DNA  length = 24
FEATURE                 Location/Qualifiers
source                  1..24
                        mol_type = other DNA
                        organism = Synthetic construct
SEQUENCE: 290
cgcggtaggt gggaggtttt tgaa                                              24

SEQ ID NO: 291          moltype = DNA  length = 24
FEATURE                 Location/Qualifiers
source                  1..24
                        mol_type = other DNA
                        organism = Synthetic construct
SEQUENCE: 291
tgttggagtg gtaggtgagc ctct                                              24

SEQ ID NO: 292          moltype = DNA  length = 24
FEATURE                 Location/Qualifiers
source                  1..24
                        mol_type = other DNA
                        organism = Synthetic construct
SEQUENCE: 292
```

```
gaggctcacc taccactcca acat                                          24

SEQ ID NO: 293          moltype = DNA  length = 24
FEATURE                 Location/Qualifiers
source                  1..24
                        mol_type = other DNA
                        organism = Synthetic construct
SEQUENCE: 293
agcaacatac tatataatgc aagg                                          24

SEQ ID NO: 294          moltype = DNA  length = 24
FEATURE                 Location/Qualifiers
source                  1..24
                        mol_type = other DNA
                        organism = Synthetic construct
SEQUENCE: 294
cttgcattat atagtatgtt gcta                                          24

SEQ ID NO: 295          moltype = DNA  length = 24
FEATURE                 Location/Qualifiers
source                  1..24
                        mol_type = other DNA
                        organism = Synthetic construct
SEQUENCE: 295
tatgaatctt catcaaccaa aagc                                          24

SEQ ID NO: 296          moltype = DNA  length = 24
FEATURE                 Location/Qualifiers
source                  1..24
                        mol_type = other DNA
                        organism = Synthetic construct
SEQUENCE: 296
cttttggttg atgaagattc atat                                          24

SEQ ID NO: 297          moltype = DNA  length = 24
FEATURE                 Location/Qualifiers
source                  1..24
                        mol_type = other DNA
                        organism = Synthetic construct
SEQUENCE: 297
aatggcaagt gtgtgcaata gtag                                          24

SEQ ID NO: 298          moltype = DNA  length = 24
FEATURE                 Location/Qualifiers
source                  1..24
                        mol_type = other DNA
                        organism = Synthetic construct
SEQUENCE: 298
tactattgca cacacttgcc attg                                          24

SEQ ID NO: 299          moltype = DNA  length = 24
FEATURE                 Location/Qualifiers
source                  1..24
                        mol_type = other DNA
                        organism = Synthetic construct
SEQUENCE: 299
actacaactc tcaaaactcc tttc                                          24

SEQ ID NO: 300          moltype = DNA  length = 24
FEATURE                 Location/Qualifiers
source                  1..24
                        mol_type = other DNA
                        organism = Synthetic construct
SEQUENCE: 300
aaaggagttt tgagagttgt agta                                          24

SEQ ID NO: 301          moltype = DNA  length = 24
FEATURE                 Location/Qualifiers
source                  1..24
                        mol_type = other DNA
                        organism = Synthetic construct
SEQUENCE: 301
ccaatacttc tttatcttca actc                                          24

SEQ ID NO: 302          moltype = DNA  length = 24
FEATURE                 Location/Qualifiers
source                  1..24
                        mol_type = other DNA
                        organism = Synthetic construct
```

```
SEQUENCE: 302
agttgaagat aaagaagtat tgga                                              24

SEQ ID NO: 303          moltype = DNA  length = 24
FEATURE                 Location/Qualifiers
source                  1..24
                        mol_type = other DNA
                        organism = Synthetic construct
SEQUENCE: 303
ctctcaactt ttcctccatg gaaa                                              24

SEQ ID NO: 304          moltype = DNA  length = 24
FEATURE                 Location/Qualifiers
source                  1..24
                        mol_type = other DNA
                        organism = Synthetic construct
SEQUENCE: 304
ttccatggag gaaaagttga gagg                                              24

SEQ ID NO: 305          moltype = DNA  length = 24
FEATURE                 Location/Qualifiers
source                  1..24
                        mol_type = other DNA
                        organism = Synthetic construct
SEQUENCE: 305
caaatgttca aagtttcatg caag                                              24

SEQ ID NO: 306          moltype = DNA  length = 24
FEATURE                 Location/Qualifiers
source                  1..24
                        mol_type = other DNA
                        organism = Synthetic construct
SEQUENCE: 306
ttgcatgaaa ctttgaacat ttgg                                              24

SEQ ID NO: 307          moltype = DNA  length = 24
FEATURE                 Location/Qualifiers
source                  1..24
                        mol_type = other DNA
                        organism = Synthetic construct
SEQUENCE: 307
ataataacgg tgaccaaaac gttg                                              24

SEQ ID NO: 308          moltype = DNA  length = 24
FEATURE                 Location/Qualifiers
source                  1..24
                        mol_type = other DNA
                        organism = Synthetic construct
SEQUENCE: 308
aacgttttgg tcaccgttat tatt                                              24

SEQ ID NO: 309          moltype = DNA  length = 24
FEATURE                 Location/Qualifiers
source                  1..24
                        mol_type = other DNA
                        organism = Synthetic construct
SEQUENCE: 309
ttctgttgat cgaagaaatg ttct                                              24

SEQ ID NO: 310          moltype = DNA  length = 24
FEATURE                 Location/Qualifiers
source                  1..24
                        mol_type = other DNA
                        organism = Synthetic construct
SEQUENCE: 310
gaacatttct tcgatcaaca gaat                                              24

SEQ ID NO: 311          moltype = DNA  length = 24
FEATURE                 Location/Qualifiers
source                  1..24
                        mol_type = other DNA
                        organism = Synthetic construct
SEQUENCE: 311
ttaggaggtc tatatggtgt tgct                                              24

SEQ ID NO: 312          moltype = DNA  length = 24
FEATURE                 Location/Qualifiers
source                  1..24
                        mol_type = other DNA
```

```
                          organism = Synthetic construct
SEQUENCE: 312
gcaacaccat atagacctcc taaa                                              24

SEQ ID NO: 313            moltype = DNA   length = 24
FEATURE                   Location/Qualifiers
source                    1..24
                          mol_type = other DNA
                          organism = Synthetic construct
SEQUENCE: 313
taccattagc tgcatccgct gctc                                              24

SEQ ID NO: 314            moltype = DNA   length = 24
FEATURE                   Location/Qualifiers
source                    1..24
                          mol_type = other DNA
                          organism = Synthetic construct
SEQUENCE: 314
agcagcggat gcagctaatg gtat                                              24

SEQ ID NO: 315            moltype = DNA   length = 24
FEATURE                   Location/Qualifiers
source                    1..24
                          mol_type = other DNA
                          organism = Synthetic construct
SEQUENCE: 315
gatcaaagga tggctaaatt tttc                                              24

SEQ ID NO: 316            moltype = DNA   length = 24
FEATURE                   Location/Qualifiers
source                    1..24
                          mol_type = other DNA
                          organism = Synthetic construct
SEQUENCE: 316
aaaaatttag ccatcctttg atca                                              24

SEQ ID NO: 317            moltype = DNA   length = 24
FEATURE                   Location/Qualifiers
source                    1..24
                          mol_type = other DNA
                          organism = Synthetic construct
SEQUENCE: 317
ttgaacttga ggatcaatat ttcc                                              24

SEQ ID NO: 318            moltype = DNA   length = 24
FEATURE                   Location/Qualifiers
source                    1..24
                          mol_type = other DNA
                          organism = Synthetic construct
SEQUENCE: 318
gaaatattga tcctcaagtt caaa                                              24

SEQ ID NO: 319            moltype = DNA   length = 24
FEATURE                   Location/Qualifiers
source                    1..24
                          mol_type = other DNA
                          organism = Synthetic construct
SEQUENCE: 319
gagagtgagt aattactcca agat                                              24

SEQ ID NO: 320            moltype = DNA   length = 24
FEATURE                   Location/Qualifiers
source                    1..24
                          mol_type = other DNA
                          organism = Synthetic construct
SEQUENCE: 320
tcttggagta attactcact ctct                                              24

SEQ ID NO: 321            moltype = DNA   length = 24
FEATURE                   Location/Qualifiers
source                    1..24
                          mol_type = other DNA
                          organism = Synthetic construct
SEQUENCE: 321
acaattatca ccaacgtgtt acac                                              24

SEQ ID NO: 322            moltype = DNA   length = 24
FEATURE                   Location/Qualifiers
source                    1..24
```

```
                           mol_type = other DNA
                           organism = Synthetic construct
SEQUENCE: 322
tgtaacacgt tggtgataat tgta                                              24

SEQ ID NO: 323             moltype = DNA  length = 24
FEATURE                    Location/Qualifiers
source                     1..24
                           mol_type = other DNA
                           organism = Synthetic construct
SEQUENCE: 323
gctacatata ccttcaccat tttg                                              24

SEQ ID NO: 324             moltype = DNA  length = 24
FEATURE                    Location/Qualifiers
source                     1..24
                           mol_type = other DNA
                           organism = Synthetic construct
SEQUENCE: 324
aaaatggtga aggtatatgt agca                                              24

SEQ ID NO: 325             moltype = DNA  length = 24
FEATURE                    Location/Qualifiers
source                     1..24
                           mol_type = other DNA
                           organism = Synthetic construct
SEQUENCE: 325
gcaactcttc taacaaaaaa tcac                                              24

SEQ ID NO: 326             moltype = DNA  length = 24
FEATURE                    Location/Qualifiers
source                     1..24
                           mol_type = other DNA
                           organism = Synthetic construct
SEQUENCE: 326
tgatttttg ttagaagagt tgca                                               24

SEQ ID NO: 327             moltype = DNA  length = 24
FEATURE                    Location/Qualifiers
source                     1..24
                           mol_type = other DNA
                           organism = Synthetic construct
SEQUENCE: 327
aacacaatgt cttcttctag tact                                              24

SEQ ID NO: 328             moltype = DNA  length = 24
FEATURE                    Location/Qualifiers
source                     1..24
                           mol_type = other DNA
                           organism = Synthetic construct
SEQUENCE: 328
gtactagaag aagacattgt gttg                                              24

SEQ ID NO: 329             moltype = DNA  length = 24
FEATURE                    Location/Qualifiers
source                     1..24
                           mol_type = other DNA
                           organism = Synthetic construct
SEQUENCE: 329
ttccattatg caccaacaaa tccc                                              24

SEQ ID NO: 330             moltype = DNA  length = 24
FEATURE                    Location/Qualifiers
source                     1..24
                           mol_type = other DNA
                           organism = Synthetic construct
SEQUENCE: 330
ggatttgttg gtgcataatg gaag                                              24

SEQ ID NO: 331             moltype = DNA  length = 24
FEATURE                    Location/Qualifiers
source                     1..24
                           mol_type = other DNA
                           organism = Synthetic construct
SEQUENCE: 331
ttccttcacc accaacaact catc                                              24

SEQ ID NO: 332             moltype = DNA  length = 24
FEATURE                    Location/Qualifiers
```

```
source                  1..24
                        mol_type = other DNA
                        organism = Synthetic construct
SEQUENCE: 332
atgagttgtt ggtggtgaag gaag                                              24

SEQ ID NO: 333          moltype = DNA  length = 24
FEATURE                 Location/Qualifiers
source                  1..24
                        mol_type = other DNA
                        organism = Synthetic construct
SEQUENCE: 333
tcaaaccct ctcaactttt cctc                                               24

SEQ ID NO: 334          moltype = DNA  length = 24
FEATURE                 Location/Qualifiers
source                  1..24
                        mol_type = other DNA
                        organism = Synthetic construct
SEQUENCE: 334
aggaaaagtt gagagggttt tgat                                              24

SEQ ID NO: 335          moltype = DNA  length = 24
FEATURE                 Location/Qualifiers
source                  1..24
                        mol_type = other DNA
                        organism = Synthetic construct
SEQUENCE: 335
gacgtaatca aagtttcaag gttt                                              24

SEQ ID NO: 336          moltype = DNA  length = 24
FEATURE                 Location/Qualifiers
source                  1..24
                        mol_type = other DNA
                        organism = Synthetic construct
SEQUENCE: 336
aaccttgaaa ctttgattac gtct                                              24

SEQ ID NO: 337          moltype = DNA  length = 24
FEATURE                 Location/Qualifiers
source                  1..24
                        mol_type = other DNA
                        organism = Synthetic construct
SEQUENCE: 337
cgtcaacaat aatgttggcg agca                                              24

SEQ ID NO: 338          moltype = DNA  length = 24
FEATURE                 Location/Qualifiers
source                  1..24
                        mol_type = other DNA
                        organism = Synthetic construct
SEQUENCE: 338
gctcgccaac attattgttg acgt                                              24

SEQ ID NO: 339          moltype = DNA  length = 24
FEATURE                 Location/Qualifiers
source                  1..24
                        mol_type = other DNA
                        organism = Synthetic construct
SEQUENCE: 339
aaccttgacg ctgttgatag gcga                                              24

SEQ ID NO: 340          moltype = DNA  length = 24
FEATURE                 Location/Qualifiers
source                  1..24
                        mol_type = other DNA
                        organism = Synthetic construct
SEQUENCE: 340
cgcctatcaa cagcgtcaag gttt                                              24

SEQ ID NO: 341          moltype = DNA  length = 24
FEATURE                 Location/Qualifiers
source                  1..24
                        mol_type = other DNA
                        organism = Synthetic construct
SEQUENCE: 341
ttttagggtt aggaggtctt tatg                                              24

SEQ ID NO: 342          moltype = DNA  length = 24
```

```
FEATURE                 Location/Qualifiers
source                  1..24
                        mol_type = other DNA
                        organism = Synthetic construct
SEQUENCE: 342
ataaagacct cctaaccctr aaag                                              24

SEQ ID NO: 343          moltype = DNA   length = 24
FEATURE                 Location/Qualifiers
source                  1..24
                        mol_type = other DNA
                        organism = Synthetic construct
SEQUENCE: 343
taatcttgca ccattagcct ctgc                                              24

SEQ ID NO: 344          moltype = DNA   length = 24
FEATURE                 Location/Qualifiers
source                  1..24
                        mol_type = other DNA
                        organism = Synthetic construct
SEQUENCE: 344
cagaggctaa tggtgcaaga ttag                                              24

SEQ ID NO: 345          moltype = DNA   length = 24
FEATURE                 Location/Qualifiers
source                  1..24
                        mol_type = other DNA
                        organism = Synthetic construct
SEQUENCE: 345
tgcaaaagaa aataggatct gcat                                              24

SEQ ID NO: 346          moltype = DNA   length = 24
FEATURE                 Location/Qualifiers
source                  1..24
                        mol_type = other DNA
                        organism = Synthetic construct
SEQUENCE: 346
tgcagatcct attttctttt gcat                                              24

SEQ ID NO: 347          moltype = DNA   length = 24
FEATURE                 Location/Qualifiers
source                  1..24
                        mol_type = other DNA
                        organism = Synthetic construct
SEQUENCE: 347
atacaaaacc atttcaaaac tgcg                                              24

SEQ ID NO: 348          moltype = DNA   length = 24
FEATURE                 Location/Qualifiers
source                  1..24
                        mol_type = other DNA
                        organism = Synthetic construct
SEQUENCE: 348
gcagttttga aatggttttg tatt                                              24

SEQ ID NO: 349          moltype = DNA   length = 24
FEATURE                 Location/Qualifiers
source                  1..24
                        mol_type = other DNA
                        organism = Synthetic construct
SEQUENCE: 349
cgtttgtact aggtacatga attt                                              24

SEQ ID NO: 350          moltype = DNA   length = 24
FEATURE                 Location/Qualifiers
source                  1..24
                        mol_type = other DNA
                        organism = Synthetic construct
SEQUENCE: 350
aattcatgta cctagtacaa acgt                                              24

SEQ ID NO: 351          moltype = DNA   length = 24
FEATURE                 Location/Qualifiers
source                  1..24
                        mol_type = other DNA
                        organism = Synthetic construct
SEQUENCE: 351
aaatactgat gaaacgctgc aaag                                              24
```

```
SEQ ID NO: 352          moltype = DNA   length = 24
FEATURE                 Location/Qualifiers
source                  1..24
                        mol_type = other DNA
                        organism = Synthetic construct
SEQUENCE: 352
tttgcagcgt tcatcagta ttta                                                 24

SEQ ID NO: 353          moltype = DNA   length = 24
FEATURE                 Location/Qualifiers
source                  1..24
                        mol_type = other DNA
                        organism = Synthetic construct
SEQUENCE: 353
actcatccca gcaatggctt cttc                                                24

SEQ ID NO: 354          moltype = DNA   length = 24
FEATURE                 Location/Qualifiers
source                  1..24
                        mol_type = other DNA
                        organism = Synthetic construct
SEQUENCE: 354
aagaagccat tgctgggatg agtg                                                24

SEQ ID NO: 355          moltype = DNA   length = 24
FEATURE                 Location/Qualifiers
source                  1..24
                        mol_type = other DNA
                        organism = Synthetic construct
SEQUENCE: 355
cctttgtgca ctaccaatat tccc                                                24

SEQ ID NO: 356          moltype = DNA   length = 24
FEATURE                 Location/Qualifiers
source                  1..24
                        mol_type = other DNA
                        organism = Synthetic construct
SEQUENCE: 356
ggaatattgg tagtgcacaa aggt                                                24

SEQ ID NO: 357          moltype = DNA   length = 24
FEATURE                 Location/Qualifiers
source                  1..24
                        mol_type = other DNA
                        organism = Synthetic construct
SEQUENCE: 357
tctccaataa taccaactca tctt                                                24

SEQ ID NO: 358          moltype = DNA   length = 24
FEATURE                 Location/Qualifiers
source                  1..24
                        mol_type = other DNA
                        organism = Synthetic construct
SEQUENCE: 358
agatgagttg gtattattgg agaa                                                24

SEQ ID NO: 359          moltype = DNA   length = 24
FEATURE                 Location/Qualifiers
source                  1..24
                        mol_type = other DNA
                        organism = Synthetic construct
SEQUENCE: 359
aaaaccctct cagcttttcc tcca                                                24

SEQ ID NO: 360          moltype = DNA   length = 24
FEATURE                 Location/Qualifiers
source                  1..24
                        mol_type = other DNA
                        organism = Synthetic construct
SEQUENCE: 360
ggaggaaaag ctgagagggt tttg                                                24

SEQ ID NO: 361          moltype = DNA   length = 24
FEATURE                 Location/Qualifiers
source                  1..24
                        mol_type = other DNA
                        organism = Synthetic construct
SEQUENCE: 361
cgtagtcaaa gtttcaaggt ttca                                                24
```

```
SEQ ID NO: 362          moltype = DNA   length = 24
FEATURE                 Location/Qualifiers
source                  1..24
                        mol_type = other DNA
                        organism = Synthetic construct
SEQUENCE: 362
gaaaccttga aactttgact acgc                                              24

SEQ ID NO: 363          moltype = DNA   length = 24
FEATURE                 Location/Qualifiers
source                  1..24
                        mol_type = other DNA
                        organism = Synthetic construct
SEQUENCE: 363
atagcgagca tgacaaaaat aacc                                              24

SEQ ID NO: 364          moltype = DNA   length = 24
FEATURE                 Location/Qualifiers
source                  1..24
                        mol_type = other DNA
                        organism = Synthetic construct
SEQUENCE: 364
gttatttttg tcatgctcgc tata                                              24

SEQ ID NO: 365          moltype = DNA   length = 24
FEATURE                 Location/Qualifiers
source                  1..24
                        mol_type = other DNA
                        organism = Synthetic construct
SEQUENCE: 365
cgatgctgtt gataggagaa atgt                                              24

SEQ ID NO: 366          moltype = DNA   length = 24
FEATURE                 Location/Qualifiers
source                  1..24
                        mol_type = other DNA
                        organism = Synthetic construct
SEQUENCE: 366
catttctcct atcaacagca tcgt                                              24

SEQ ID NO: 367          moltype = DNA   length = 24
FEATURE                 Location/Qualifiers
source                  1..24
                        mol_type = other DNA
                        organism = Synthetic construct
SEQUENCE: 367
gggttaggag gtctttatgg tgct                                              24

SEQ ID NO: 368          moltype = DNA   length = 24
FEATURE                 Location/Qualifiers
source                  1..24
                        mol_type = other DNA
                        organism = Synthetic construct
SEQUENCE: 368
gcaccataaa gacctcctaa ccct                                              24

SEQ ID NO: 369          moltype = DNA   length = 24
FEATURE                 Location/Qualifiers
source                  1..24
                        mol_type = other DNA
                        organism = Synthetic construct
SEQUENCE: 369
ttgcaccatt agccactgct gctc                                              24

SEQ ID NO: 370          moltype = DNA   length = 24
FEATURE                 Location/Qualifiers
source                  1..24
                        mol_type = other DNA
                        organism = Synthetic construct
SEQUENCE: 370
agcagcagtg gctaatggtg caag                                              24

SEQ ID NO: 371          moltype = DNA   length = 24
FEATURE                 Location/Qualifiers
source                  1..24
                        mol_type = other DNA
                        organism = Synthetic construct
SEQUENCE: 371
```

```
accacctgat tgaaaactt gtag                                              24

SEQ ID NO: 372          moltype = DNA   length = 24
FEATURE                 Location/Qualifiers
source                  1..24
                        mol_type = other DNA
                        organism = Synthetic construct
SEQUENCE: 372
tacaagtttt caaatcaggt ggtg                                             24

SEQ ID NO: 373          moltype = DNA   length = 24
FEATURE                 Location/Qualifiers
source                  1..24
                        mol_type = other DNA
                        organism = Synthetic construct
SEQUENCE: 373
actgtaactc ctggtggtcc agca                                             24

SEQ ID NO: 374          moltype = DNA   length = 24
FEATURE                 Location/Qualifiers
source                  1..24
                        mol_type = other DNA
                        organism = Synthetic construct
SEQUENCE: 374
gctggaccac caggagttac agtg                                             24

SEQ ID NO: 375          moltype = DNA   length = 24
FEATURE                 Location/Qualifiers
source                  1..24
                        mol_type = other DNA
                        organism = Synthetic construct
SEQUENCE: 375
tatgtgctca cgtggacaca ttac                                             24

SEQ ID NO: 376          moltype = DNA   length = 24
FEATURE                 Location/Qualifiers
source                  1..24
                        mol_type = other DNA
                        organism = Synthetic construct
SEQUENCE: 376
taatgtgtcc acgtgagcac atag                                             24

SEQ ID NO: 377          moltype = DNA   length = 24
FEATURE                 Location/Qualifiers
source                  1..24
                        mol_type = other DNA
                        organism = Synthetic construct
SEQUENCE: 377
gatgcaatat ttatgatgtt cacg                                             24

SEQ ID NO: 378          moltype = DNA   length = 24
FEATURE                 Location/Qualifiers
source                  1..24
                        mol_type = other DNA
                        organism = Synthetic construct
SEQUENCE: 378
gtgaacatca taaatattgc atca                                             24

SEQ ID NO: 379          moltype = DNA   length = 24
FEATURE                 Location/Qualifiers
source                  1..24
                        mol_type = other DNA
                        organism = Synthetic construct
SEQUENCE: 379
attatattct cgacaagttg aacg                                             24

SEQ ID NO: 380          moltype = DNA   length = 24
FEATURE                 Location/Qualifiers
source                  1..24
                        mol_type = other DNA
                        organism = Synthetic construct
SEQUENCE: 380
gttcaacttg tcgagaatat aatt                                             24

SEQ ID NO: 381          moltype = DNA   length = 24
FEATURE                 Location/Qualifiers
source                  1..24
                        mol_type = other DNA
                        organism = Synthetic construct
```

-continued

```
SEQUENCE: 381
ggaaatgatg gagattatta tggt                                          24

SEQ ID NO: 382         moltype = DNA  length = 24
FEATURE                Location/Qualifiers
source                 1..24
                       mol_type = other DNA
                       organism = Synthetic construct
SEQUENCE: 382
ccataataat ctccatcatt tcca                                          24

SEQ ID NO: 383         moltype = DNA  length = 24
FEATURE                Location/Qualifiers
source                 1..24
                       mol_type = other DNA
                       organism = Synthetic construct
SEQUENCE: 383
tcttcctcac aagtaatta caaa                                           24

SEQ ID NO: 384         moltype = DNA  length = 24
FEATURE                Location/Qualifiers
source                 1..24
                       mol_type = other DNA
                       organism = Synthetic construct
SEQUENCE: 384
ttgtaattac cttgtgagga agaa                                          24

SEQ ID NO: 385         moltype = DNA  length = 24
FEATURE                Location/Qualifiers
source                 1..24
                       mol_type = other DNA
                       organism = Synthetic construct
SEQUENCE: 385
ccttagcttg ctccatatta ttct                                          24

SEQ ID NO: 386         moltype = DNA  length = 24
FEATURE                Location/Qualifiers
source                 1..24
                       mol_type = other DNA
                       organism = Synthetic construct
SEQUENCE: 386
gaataatatg gagcaagcta agga                                          24

SEQ ID NO: 387         moltype = DNA  length = 24
FEATURE                Location/Qualifiers
source                 1..24
                       mol_type = other DNA
                       organism = Synthetic construct
SEQUENCE: 387
tgctagccct agatgttcat gaat                                          24

SEQ ID NO: 388         moltype = DNA  length = 24
FEATURE                Location/Qualifiers
source                 1..24
                       mol_type = other DNA
                       organism = Synthetic construct
SEQUENCE: 388
ttcatgaaca tctagggcta gcat                                          24

SEQ ID NO: 389         moltype = DNA  length = 24
FEATURE                Location/Qualifiers
source                 1..24
                       mol_type = other DNA
                       organism = Synthetic construct
SEQUENCE: 389
caagcaaaaa aatgtcttcc attc                                          24

SEQ ID NO: 390         moltype = DNA  length = 24
FEATURE                Location/Qualifiers
source                 1..24
                       mol_type = other DNA
                       organism = Synthetic construct
SEQUENCE: 390
aatggaagac attttttttgc ttgt                                         24

SEQ ID NO: 391         moltype = DNA  length = 24
FEATURE                Location/Qualifiers
source                 1..24
                       mol_type = other DNA
```

-continued

```
                          organism = Synthetic construct
SEQUENCE: 391
cactaccaat actctctctt cttc                                              24

SEQ ID NO: 392           moltype = DNA  length = 24
FEATURE                  Location/Qualifiers
source                   1..24
                         mol_type = other DNA
                         organism = Synthetic construct
SEQUENCE: 392
aagaagagag agtattggta gtgg                                              24

SEQ ID NO: 393           moltype = DNA  length = 24
FEATURE                  Location/Qualifiers
source                   1..24
                         mol_type = other DNA
                         organism = Synthetic construct
SEQUENCE: 393
accactttt ccaacttgca ttct                                               24

SEQ ID NO: 394           moltype = DNA  length = 24
FEATURE                  Location/Qualifiers
source                   1..24
                         mol_type = other DNA
                         organism = Synthetic construct
SEQUENCE: 394
gaatgcaagt tggaaaaagt ggtg                                              24

SEQ ID NO: 395           moltype = DNA  length = 24
FEATURE                  Location/Qualifiers
source                   1..24
                         mol_type = other DNA
                         organism = Synthetic construct
SEQUENCE: 395
gcaaaaacat caaaaatttc ctcc                                              24

SEQ ID NO: 396           moltype = DNA  length = 24
FEATURE                  Location/Qualifiers
source                   1..24
                         mol_type = other DNA
                         organism = Synthetic construct
SEQUENCE: 396
gaggaaattt ttgatgtttt tgca                                              24

SEQ ID NO: 397           moltype = DNA  length = 24
FEATURE                  Location/Qualifiers
source                   1..24
                         mol_type = other DNA
                         organism = Synthetic construct
SEQUENCE: 397
agcataatgt ccatcgtaat ttcc                                              24

SEQ ID NO: 398           moltype = DNA  length = 24
FEATURE                  Location/Qualifiers
source                   1..24
                         mol_type = other DNA
                         organism = Synthetic construct
SEQUENCE: 398
gaaattacga tggacattat gctt                                              24

SEQ ID NO: 399           moltype = DNA  length = 24
FEATURE                  Location/Qualifiers
source                   1..24
                         mol_type = other DNA
                         organism = Synthetic construct
SEQUENCE: 399
gcaaaaccat agatgataat agtc                                              24

SEQ ID NO: 400           moltype = DNA  length = 24
FEATURE                  Location/Qualifiers
source                   1..24
                         mol_type = other DNA
                         organism = Synthetic construct
SEQUENCE: 400
actattatca tctatggttt tgca                                              24

SEQ ID NO: 401           moltype = DNA  length = 24
FEATURE                  Location/Qualifiers
source                   1..24
```

```
                        mol_type = other DNA
                        organism = Synthetic construct
SEQUENCE: 401
caataactca cccatcgaca tttc                                              24

SEQ ID NO: 402          moltype = DNA  length = 24
FEATURE                 Location/Qualifiers
source                  1..24
                        mol_type = other DNA
                        organism = Synthetic construct
SEQUENCE: 402
aaatgtcgat gggtgagtta ttgt                                              24

SEQ ID NO: 403          moltype = DNA  length = 24
FEATURE                 Location/Qualifiers
source                  1..24
                        mol_type = other DNA
                        organism = Synthetic construct
SEQUENCE: 403
acaatatgat cgatagaaga aacg                                              24

SEQ ID NO: 404          moltype = DNA  length = 24
FEATURE                 Location/Qualifiers
source                  1..24
                        mol_type = other DNA
                        organism = Synthetic construct
SEQUENCE: 404
gtttcttcta tcgatcatat tgtt                                              24

SEQ ID NO: 405          moltype = DNA  length = 24
FEATURE                 Location/Qualifiers
source                  1..24
                        mol_type = other DNA
                        organism = Synthetic construct
SEQUENCE: 405
tcggcctgcc gagcctagac aata                                              24

SEQ ID NO: 406          moltype = DNA  length = 24
FEATURE                 Location/Qualifiers
source                  1..24
                        mol_type = other DNA
                        organism = Synthetic construct
SEQUENCE: 406
attgtctagg ctcggcaggc cgac                                              24

SEQ ID NO: 407          moltype = DNA  length = 24
FEATURE                 Location/Qualifiers
source                  1..24
                        mol_type = other DNA
                        organism = Synthetic construct
SEQUENCE: 407
tctcctctcg atgggtctc tccc                                               24

SEQ ID NO: 408          moltype = DNA  length = 24
FEATURE                 Location/Qualifiers
source                  1..24
                        mol_type = other DNA
                        organism = Synthetic construct
SEQUENCE: 408
ggagagaccc catcgagagg agag                                              24

SEQ ID NO: 409          moltype = DNA  length = 24
FEATURE                 Location/Qualifiers
source                  1..24
                        mol_type = other DNA
                        organism = Synthetic construct
SEQUENCE: 409
atccaggcgc cgccggtgac cttc                                              24

SEQ ID NO: 410          moltype = DNA  length = 24
FEATURE                 Location/Qualifiers
source                  1..24
                        mol_type = other DNA
                        organism = Synthetic construct
SEQUENCE: 410
aaggtcaccg gcggcgcctg gatc                                              24

SEQ ID NO: 411          moltype = DNA  length = 24
FEATURE                 Location/Qualifiers
```

```
source                    1..24
                          mol_type = other DNA
                          organism = Synthetic construct
SEQUENCE: 411
gcgcacgcgc ggatcattcg tccc                                              24

SEQ ID NO: 412            moltype = DNA   length = 24
FEATURE                   Location/Qualifiers
source                    1..24
                          mol_type = other DNA
                          organism = Synthetic construct
SEQUENCE: 412
ggacgaatga tccgcgcgtg cgca                                              24

SEQ ID NO: 413            moltype = DNA   length = 24
FEATURE                   Location/Qualifiers
source                    1..24
                          mol_type = other DNA
                          organism = Synthetic construct
SEQUENCE: 413
acagtctgac acgttagata gaga                                              24

SEQ ID NO: 414            moltype = DNA   length = 24
FEATURE                   Location/Qualifiers
source                    1..24
                          mol_type = other DNA
                          organism = Synthetic construct
SEQUENCE: 414
ctctatctaa cgtgtcagac tgtc                                              24

SEQ ID NO: 415            moltype = DNA   length = 24
FEATURE                   Location/Qualifiers
source                    1..24
                          mol_type = other DNA
                          organism = Synthetic construct
SEQUENCE: 415
atgcgccagg tcgtggaccg tccc                                              24

SEQ ID NO: 416            moltype = DNA   length = 24
FEATURE                   Location/Qualifiers
source                    1..24
                          mol_type = other DNA
                          organism = Synthetic construct
SEQUENCE: 416
ggacggtcca cgacctggcg catg                                              24

SEQ ID NO: 417            moltype = DNA   length = 24
FEATURE                   Location/Qualifiers
source                    1..24
                          mol_type = other DNA
                          organism = Synthetic construct
SEQUENCE: 417
agagaacact gccgtcggtt ttta                                              24

SEQ ID NO: 418            moltype = DNA   length = 24
FEATURE                   Location/Qualifiers
source                    1..24
                          mol_type = other DNA
                          organism = Synthetic construct
SEQUENCE: 418
aaaaaccgac ggcagtgttc tctg                                              24

SEQ ID NO: 419            moltype = DNA   length = 24
FEATURE                   Location/Qualifiers
source                    1..24
                          mol_type = other DNA
                          organism = Synthetic construct
SEQUENCE: 419
ttgacgttcg aaaagatgtc aaca                                              24

SEQ ID NO: 420            moltype = DNA   length = 24
FEATURE                   Location/Qualifiers
source                    1..24
                          mol_type = other DNA
                          organism = Synthetic construct
SEQUENCE: 420
gttgacatct tttcgaacgt caat                                              24

SEQ ID NO: 421            moltype = DNA   length = 24
```

```
                        -continued

FEATURE                 Location/Qualifiers
source                  1..24
                        mol_type = other DNA
                        organism = Synthetic construct
SEQUENCE: 421
agttttttta tacaactgag agag                                              24

SEQ ID NO: 422          moltype = DNA   length = 24
FEATURE                 Location/Qualifiers
source                  1..24
                        mol_type = other DNA
                        organism = Synthetic construct
SEQUENCE: 422
tctctcagtt gtataaaaaa actc                                              24

SEQ ID NO: 423          moltype = DNA   length = 24
FEATURE                 Location/Qualifiers
source                  1..24
                        mol_type = other DNA
                        organism = Synthetic construct
SEQUENCE: 423
gagtgagtta aatggcaaca aaca                                              24

SEQ ID NO: 424          moltype = DNA   length = 24
FEATURE                 Location/Qualifiers
source                  1..24
                        mol_type = other DNA
                        organism = Synthetic construct
SEQUENCE: 424
gtttgttgcc atttaactca ctcg                                              24

SEQ ID NO: 425          moltype = DNA   length = 24
FEATURE                 Location/Qualifiers
source                  1..24
                        mol_type = other DNA
                        organism = Synthetic construct
SEQUENCE: 425
ggaaaaaaac tatgagatgt catc                                              24

SEQ ID NO: 426          moltype = DNA   length = 24
FEATURE                 Location/Qualifiers
source                  1..24
                        mol_type = other DNA
                        organism = Synthetic construct
SEQUENCE: 426
atgacatctc atagtttttt tcct                                              24

SEQ ID NO: 427          moltype = DNA   length = 24
FEATURE                 Location/Qualifiers
source                  1..24
                        mol_type = other DNA
                        organism = Synthetic construct
SEQUENCE: 427
atgacggtaa ataaatatgg atgg                                              24

SEQ ID NO: 428          moltype = DNA   length = 24
FEATURE                 Location/Qualifiers
source                  1..24
                        mol_type = other DNA
                        organism = Synthetic construct
SEQUENCE: 428
catccatatt tatttaccgt cata                                              24

SEQ ID NO: 429          moltype = DNA   length = 24
FEATURE                 Location/Qualifiers
source                  1..24
                        mol_type = other DNA
                        organism = Synthetic construct
SEQUENCE: 429
ctaaaacgaa aagtggcaaa acct                                              24

SEQ ID NO: 430          moltype = DNA   length = 24
FEATURE                 Location/Qualifiers
source                  1..24
                        mol_type = other DNA
                        organism = Synthetic construct
SEQUENCE: 430
ggttttgcca cttttcgttt tagt                                              24
```

```
SEQ ID NO: 431            moltype = DNA   length = 24
FEATURE                   Location/Qualifiers
source                    1..24
                          mol_type = other DNA
                          organism = Synthetic construct
SEQUENCE: 431
gacgggtgtc gccgagtgca gccg                                              24

SEQ ID NO: 432            moltype = DNA   length = 24
FEATURE                   Location/Qualifiers
source                    1..24
                          mol_type = other DNA
                          organism = Synthetic construct
SEQUENCE: 432
ggctgcactc ggcgacaccc gtcc                                              24

SEQ ID NO: 433            moltype = DNA   length = 24
FEATURE                   Location/Qualifiers
source                    1..24
                          mol_type = other DNA
                          organism = Synthetic construct
SEQUENCE: 433
accccaccg atgtcctgag attg                                               24

SEQ ID NO: 434            moltype = DNA   length = 24
FEATURE                   Location/Qualifiers
source                    1..24
                          mol_type = other DNA
                          organism = Synthetic construct
SEQUENCE: 434
aatctcagga catcggtggg ggtt                                              24

SEQ ID NO: 435            moltype = DNA   length = 24
FEATURE                   Location/Qualifiers
source                    1..24
                          mol_type = other DNA
                          organism = Synthetic construct
SEQUENCE: 435
aagccgcagg cagcatctgc atct                                              24

SEQ ID NO: 436            moltype = DNA   length = 24
FEATURE                   Location/Qualifiers
source                    1..24
                          mol_type = other DNA
                          organism = Synthetic construct
SEQUENCE: 436
gatgcagatg ctgcctgcgg cttc                                              24

SEQ ID NO: 437            moltype = DNA   length = 24
FEATURE                   Location/Qualifiers
source                    1..24
                          mol_type = other DNA
                          organism = Synthetic construct
SEQUENCE: 437
ctccgctccg cctactgctg ctgg                                              24

SEQ ID NO: 438            moltype = DNA   length = 24
FEATURE                   Location/Qualifiers
source                    1..24
                          mol_type = other DNA
                          organism = Synthetic construct
SEQUENCE: 438
cagcagcagt aggcggagcg gagg                                              24

SEQ ID NO: 439            moltype = DNA   length = 24
FEATURE                   Location/Qualifiers
source                    1..24
                          mol_type = other DNA
                          organism = Synthetic construct
SEQUENCE: 439
ggcggagaag gaggcccttg cgcc                                              24

SEQ ID NO: 440            moltype = DNA   length = 24
FEATURE                   Location/Qualifiers
source                    1..24
                          mol_type = other DNA
                          organism = Synthetic construct
SEQUENCE: 440
gcgcaagggc ctccttctcc gcct                                              24
```

```
SEQ ID NO: 441          moltype = DNA   length = 24
FEATURE                 Location/Qualifiers
source                  1..24
                        mol_type = other DNA
                        organism = Synthetic construct
SEQUENCE: 441
gccggatcag agccggtaag acca                                              24

SEQ ID NO: 442          moltype = DNA   length = 24
FEATURE                 Location/Qualifiers
source                  1..24
                        mol_type = other DNA
                        organism = Synthetic construct
SEQUENCE: 442
ggtcttaccg gctctgatcc ggcc                                              24

SEQ ID NO: 443          moltype = DNA   length = 24
FEATURE                 Location/Qualifiers
source                  1..24
                        mol_type = other DNA
                        organism = Synthetic construct
SEQUENCE: 443
cgctcctcct cgctggttgc tttc                                              24

SEQ ID NO: 444          moltype = DNA   length = 24
FEATURE                 Location/Qualifiers
source                  1..24
                        mol_type = other DNA
                        organism = Synthetic construct
SEQUENCE: 444
aaagcaacca gcgaggagga gcgt                                              24

SEQ ID NO: 445          moltype = DNA   length = 24
FEATURE                 Location/Qualifiers
source                  1..24
                        mol_type = other DNA
                        organism = Synthetic construct
SEQUENCE: 445
cgccggtatt cccagtccgt gtgc                                              24

SEQ ID NO: 446          moltype = DNA   length = 24
FEATURE                 Location/Qualifiers
source                  1..24
                        mol_type = other DNA
                        organism = Synthetic construct
SEQUENCE: 446
cacacggact gggataccg gcgg                                               24

SEQ ID NO: 447          moltype = DNA   length = 24
FEATURE                 Location/Qualifiers
source                  1..24
                        mol_type = other DNA
                        organism = Synthetic construct
SEQUENCE: 447
gtctgctccc gtcgctgcct agat                                              24

SEQ ID NO: 448          moltype = DNA   length = 24
FEATURE                 Location/Qualifiers
source                  1..24
                        mol_type = other DNA
                        organism = Synthetic construct
SEQUENCE: 448
tctaggcagc gacgggagca gaca                                              24

SEQ ID NO: 449          moltype = DNA   length = 24
FEATURE                 Location/Qualifiers
source                  1..24
                        mol_type = other DNA
                        organism = Synthetic construct
SEQUENCE: 449
ggatctttcg tgcatggcgg caga                                              24

SEQ ID NO: 450          moltype = DNA   length = 24
FEATURE                 Location/Qualifiers
source                  1..24
                        mol_type = other DNA
                        organism = Synthetic construct
SEQUENCE: 450
```
ctgccgccat gcacgaaaga tcct                                          24

SEQ ID NO: 451          moltype = DNA   length = 24
FEATURE                 Location/Qualifiers
source                  1..24
                        mol_type = other DNA
                        organism = Synthetic construct
SEQUENCE: 451
cccccccccc cccccccccc cccc                                          24

SEQ ID NO: 452          moltype = DNA   length = 24
FEATURE                 Location/Qualifiers
source                  1..24
                        mol_type = other DNA
                        organism = Synthetic construct
SEQUENCE: 452
gggggggggg gggggggggg gggg                                          24

SEQ ID NO: 453          moltype = DNA   length = 24
FEATURE                 Location/Qualifiers
source                  1..24
                        mol_type = other DNA
                        organism = Synthetic construct
SEQUENCE: 453
cgtgtatacg agttttctct aggc                                          24

SEQ ID NO: 454          moltype = DNA   length = 24
FEATURE                 Location/Qualifiers
source                  1..24
                        mol_type = other DNA
                        organism = Synthetic construct
SEQUENCE: 454
cctagagaaa actcgtatac acgg                                          24

SEQ ID NO: 455          moltype = DNA   length = 24
FEATURE                 Location/Qualifiers
source                  1..24
                        mol_type = other DNA
                        organism = Synthetic construct
SEQUENCE: 455
catgttggat tggattgcgc tagt                                          24

SEQ ID NO: 456          moltype = DNA   length = 24
FEATURE                 Location/Qualifiers
source                  1..24
                        mol_type = other DNA
                        organism = Synthetic construct
SEQUENCE: 456
ctagcgcaat ccaatccaac atgc                                          24

SEQ ID NO: 457          moltype = DNA   length = 24
FEATURE                 Location/Qualifiers
source                  1..24
                        mol_type = other DNA
                        organism = Synthetic construct
SEQUENCE: 457
gaggtgccgg ccgtacccat cctc                                          24

SEQ ID NO: 458          moltype = DNA   length = 24
FEATURE                 Location/Qualifiers
source                  1..24
                        mol_type = other DNA
                        organism = Synthetic construct
SEQUENCE: 458
aggatgggta cggccggcac ctct                                          24

SEQ ID NO: 459          moltype = DNA   length = 24
FEATURE                 Location/Qualifiers
source                  1..24
                        mol_type = other DNA
                        organism = Synthetic construct
SEQUENCE: 459
agaaaaaagg cccagtcatt tttg                                          24

SEQ ID NO: 460          moltype = DNA   length = 24
FEATURE                 Location/Qualifiers
source                  1..24
                        mol_type = other DNA
                        organism = Synthetic construct

```
SEQUENCE: 460
aaaaatgact gggccttttt tctg                                              24

SEQ ID NO: 461          moltype = DNA   length = 24
FEATURE                 Location/Qualifiers
source                  1..24
                        mol_type = other DNA
                        organism = Synthetic construct
SEQUENCE: 461
atttatttt acagctgcca catg                                               24

SEQ ID NO: 462          moltype = DNA   length = 24
FEATURE                 Location/Qualifiers
source                  1..24
                        mol_type = other DNA
                        organism = Synthetic construct
SEQUENCE: 462
atgtggcagc tgtaaaaata aata                                              24

SEQ ID NO: 463          moltype = DNA   length = 24
FEATURE                 Location/Qualifiers
source                  1..24
                        mol_type = other DNA
                        organism = Synthetic construct
SEQUENCE: 463
tttttgttgg ggttttacta ctac                                              24

SEQ ID NO: 464          moltype = DNA   length = 24
FEATURE                 Location/Qualifiers
source                  1..24
                        mol_type = other DNA
                        organism = Synthetic construct
SEQUENCE: 464
tagtagtaaa accccaacaa aaac                                              24

SEQ ID NO: 465          moltype = DNA   length = 24
FEATURE                 Location/Qualifiers
source                  1..24
                        mol_type = other DNA
                        organism = Synthetic construct
SEQUENCE: 465
aactgttttg tcaaatactg taac                                              24

SEQ ID NO: 466          moltype = DNA   length = 24
FEATURE                 Location/Qualifiers
source                  1..24
                        mol_type = other DNA
                        organism = Synthetic construct
SEQUENCE: 466
ttacagtatt tgacaaaaca gttc                                              24

SEQ ID NO: 467          moltype = DNA   length = 24
FEATURE                 Location/Qualifiers
source                  1..24
                        mol_type = other DNA
                        organism = Synthetic construct
SEQUENCE: 467
aaagctgttt gtaggagtga agct                                              24

SEQ ID NO: 468          moltype = DNA   length = 24
FEATURE                 Location/Qualifiers
source                  1..24
                        mol_type = other DNA
                        organism = Synthetic construct
SEQUENCE: 468
gcttcactcc tacaaacagc ttta                                              24

SEQ ID NO: 469          moltype = DNA   length = 24
FEATURE                 Location/Qualifiers
source                  1..24
                        mol_type = other DNA
                        organism = Synthetic construct
SEQUENCE: 469
aaacagaact tcatattgtt ccag                                              24

SEQ ID NO: 470          moltype = DNA   length = 24
FEATURE                 Location/Qualifiers
source                  1..24
                        mol_type = other DNA
```

-continued

```
                         organism = Synthetic construct
SEQUENCE: 470
tggaacaata tgaagttctg ttta                                              24

SEQ ID NO: 471           moltype = DNA  length = 24
FEATURE                  Location/Qualifiers
source                   1..24
                         mol_type = other DNA
                         organism = Synthetic construct
SEQUENCE: 471
ttccaacaaa aaaattgcaa ttcg                                              24

SEQ ID NO: 472           moltype = DNA  length = 24
FEATURE                  Location/Qualifiers
source                   1..24
                         mol_type = other DNA
                         organism = Synthetic construct
SEQUENCE: 472
gaattgcaat tttttgttg gaac                                               24

SEQ ID NO: 473           moltype = DNA  length = 24
FEATURE                  Location/Qualifiers
source                   1..24
                         mol_type = other DNA
                         organism = Synthetic construct
SEQUENCE: 473
gctaccagta cagcgctaga tgga                                              24

SEQ ID NO: 474           moltype = DNA  length = 24
FEATURE                  Location/Qualifiers
source                   1..24
                         mol_type = other DNA
                         organism = Synthetic construct
SEQUENCE: 474
ccatctagcg ctgtactggt agcc                                              24

SEQ ID NO: 475           moltype = DNA  length = 24
FEATURE                  Location/Qualifiers
source                   1..24
                         mol_type = other DNA
                         organism = Synthetic construct
SEQUENCE: 475
cgaacatgaa acgtttactt tttc                                              24

SEQ ID NO: 476           moltype = DNA  length = 24
FEATURE                  Location/Qualifiers
source                   1..24
                         mol_type = other DNA
                         organism = Synthetic construct
SEQUENCE: 476
aaaaagtaaa cgtttcatgt tcgc                                              24

SEQ ID NO: 477           moltype = DNA  length = 24
FEATURE                  Location/Qualifiers
source                   1..24
                         mol_type = other DNA
                         organism = Synthetic construct
SEQUENCE: 477
tgtttgatgg atcacattta tctc                                              24

SEQ ID NO: 478           moltype = DNA  length = 24
FEATURE                  Location/Qualifiers
source                   1..24
                         mol_type = other DNA
                         organism = Synthetic construct
SEQUENCE: 478
agataaatgt gatccatcaa acat                                              24

SEQ ID NO: 479           moltype = DNA  length = 24
FEATURE                  Location/Qualifiers
source                   1..24
                         mol_type = other DNA
                         organism = Synthetic construct
SEQUENCE: 479
tgttggatac cggtactttt tacg                                              24

SEQ ID NO: 480           moltype = DNA  length = 24
FEATURE                  Location/Qualifiers
source                   1..24
```

```
SEQ ID NO: 480 (continued)
                        mol_type = other DNA
                        organism = Synthetic construct
SEQUENCE: 480
gtaaaaagta ccggtatcca acac                                              24

SEQ ID NO: 481          moltype = DNA  length = 24
FEATURE                 Location/Qualifiers
source                  1..24
                        mol_type = other DNA
                        organism = Synthetic construct
SEQUENCE: 481
gtacaggggc cactggctat atat                                              24

SEQ ID NO: 482          moltype = DNA  length = 24
FEATURE                 Location/Qualifiers
source                  1..24
                        mol_type = other DNA
                        organism = Synthetic construct
SEQUENCE: 482
tatatagcca gtggcccctg taca                                              24

SEQ ID NO: 483          moltype = DNA  length = 24
FEATURE                 Location/Qualifiers
source                  1..24
                        mol_type = other DNA
                        organism = Synthetic construct
SEQUENCE: 483
cactccatta atttccaggg atgc                                              24

SEQ ID NO: 484          moltype = DNA  length = 24
FEATURE                 Location/Qualifiers
source                  1..24
                        mol_type = other DNA
                        organism = Synthetic construct
SEQUENCE: 484
catccctgga aattaatgga gtga                                              24

SEQ ID NO: 485          moltype = DNA  length = 24
FEATURE                 Location/Qualifiers
source                  1..24
                        mol_type = other DNA
                        organism = Synthetic construct
SEQUENCE: 485
ctctctctgc tacatacatc catt                                              24

SEQ ID NO: 486          moltype = DNA  length = 24
FEATURE                 Location/Qualifiers
source                  1..24
                        mol_type = other DNA
                        organism = Synthetic construct
SEQUENCE: 486
atggatgtat gtagcagaga gaga                                              24

SEQ ID NO: 487          moltype = DNA  length = 24
FEATURE                 Location/Qualifiers
source                  1..24
                        mol_type = other DNA
                        organism = Synthetic construct
SEQUENCE: 487
tttttttgtgg aattttgcac ttgg                                             24

SEQ ID NO: 488          moltype = DNA  length = 24
FEATURE                 Location/Qualifiers
source                  1..24
                        mol_type = other DNA
                        organism = Synthetic construct
SEQUENCE: 488
caagtgcaaa attccacaaa aaaa                                              24

SEQ ID NO: 489          moltype = DNA  length = 24
FEATURE                 Location/Qualifiers
source                  1..24
                        mol_type = other DNA
                        organism = Synthetic construct
SEQUENCE: 489
tctcagttta atttggagga tcaa                                              24

SEQ ID NO: 490          moltype = DNA  length = 24
FEATURE                 Location/Qualifiers
```

```
source                  1..24
                        mol_type = other DNA
                        organism = Synthetic construct
SEQUENCE: 490
tgatcctcca aattaaactg agaa                                                24

SEQ ID NO: 491          moltype = DNA  length = 24
FEATURE                 Location/Qualifiers
source                  1..24
                        mol_type = other DNA
                        organism = Synthetic construct
SEQUENCE: 491
agacatacat ggcggatcct ctgg                                                24

SEQ ID NO: 492          moltype = DNA  length = 24
FEATURE                 Location/Qualifiers
source                  1..24
                        mol_type = other DNA
                        organism = Synthetic construct
SEQUENCE: 492
cagaggatcc gccatgtatg tctc                                                24

SEQ ID NO: 493          moltype = DNA  length = 24
FEATURE                 Location/Qualifiers
source                  1..24
                        mol_type = other DNA
                        organism = Synthetic construct
SEQUENCE: 493
aaggtcttag cggactactt ggtg                                                24

SEQ ID NO: 494          moltype = DNA  length = 24
FEATURE                 Location/Qualifiers
source                  1..24
                        mol_type = other DNA
                        organism = Synthetic construct
SEQUENCE: 494
accaagtagt ccgctaagac cttc                                                24

SEQ ID NO: 495          moltype = DNA  length = 24
FEATURE                 Location/Qualifiers
source                  1..24
                        mol_type = other DNA
                        organism = Synthetic construct
SEQUENCE: 495
cttcgtggcc cttccaatat ctgc                                                24

SEQ ID NO: 496          moltype = DNA  length = 24
FEATURE                 Location/Qualifiers
source                  1..24
                        mol_type = other DNA
                        organism = Synthetic construct
SEQUENCE: 496
cagatattgg aagggccacg aaga                                                24

SEQ ID NO: 497          moltype = DNA  length = 24
FEATURE                 Location/Qualifiers
source                  1..24
                        mol_type = other DNA
                        organism = Synthetic construct
SEQUENCE: 497
tggtgaacac gtggtccgcc atga                                                24

SEQ ID NO: 498          moltype = DNA  length = 24
FEATURE                 Location/Qualifiers
source                  1..24
                        mol_type = other DNA
                        organism = Synthetic construct
SEQUENCE: 498
catggcggac cacgtgttca ccag                                                24

SEQ ID NO: 499          moltype = DNA  length = 24
FEATURE                 Location/Qualifiers
source                  1..24
                        mol_type = other DNA
                        organism = Synthetic construct
SEQUENCE: 499
gaacaccagg agaacgtaga gggt                                                24

SEQ ID NO: 500          moltype = DNA  length = 24
```

```
FEATURE                 Location/Qualifiers
source                  1..24
                        mol_type = other DNA
                        organism = Synthetic construct
SEQUENCE: 500
ccctctacgt tctcctggtg ttcc                                                24

SEQ ID NO: 501          moltype = DNA   length = 24
FEATURE                 Location/Qualifiers
source                  1..24
                        mol_type = other DNA
                        organism = Synthetic construct
SEQUENCE: 501
atccgaagag ggacggcctc gtct                                                24

SEQ ID NO: 502          moltype = DNA   length = 24
FEATURE                 Location/Qualifiers
source                  1..24
                        mol_type = other DNA
                        organism = Synthetic construct
SEQUENCE: 502
gacgaggccg tccctcttcg gatc                                                24

SEQ ID NO: 503          moltype = DNA   length = 24
FEATURE                 Location/Qualifiers
source                  1..24
                        mol_type = other DNA
                        organism = Synthetic construct
SEQUENCE: 503
gtcgtgggca tgcgcaacgt ggac                                                24

SEQ ID NO: 504          moltype = DNA   length = 24
FEATURE                 Location/Qualifiers
source                  1..24
                        mol_type = other DNA
                        organism = Synthetic construct
SEQUENCE: 504
tccacgttgc gcatgcccac gacc                                                24

SEQ ID NO: 505          moltype = DNA   length = 24
FEATURE                 Location/Qualifiers
source                  1..24
                        mol_type = other DNA
                        organism = Synthetic construct
SEQUENCE: 505
ggtcgacctc tccgcgttga ggaa                                                24

SEQ ID NO: 506          moltype = DNA   length = 24
FEATURE                 Location/Qualifiers
source                  1..24
                        mol_type = other DNA
                        organism = Synthetic construct
SEQUENCE: 506
tcctcaacgc ggagaggtcg acct                                                24

SEQ ID NO: 507          moltype = DNA   length = 24
FEATURE                 Location/Qualifiers
source                  1..24
                        mol_type = other DNA
                        organism = Synthetic construct
SEQUENCE: 507
ggatggtcgc cagggtggag cctc                                                24

SEQ ID NO: 508          moltype = DNA   length = 24
FEATURE                 Location/Qualifiers
source                  1..24
                        mol_type = other DNA
                        organism = Synthetic construct
SEQUENCE: 508
aggctccacc ctggcgacca tcct                                                24

SEQ ID NO: 509          moltype = DNA   length = 24
FEATURE                 Location/Qualifiers
source                  1..24
                        mol_type = other DNA
                        organism = Synthetic construct
SEQUENCE: 509
aaggctacct gccccatgaa cctc                                                24
```

-continued

```
SEQ ID NO: 510            moltype = DNA  length = 24
FEATURE                   Location/Qualifiers
source                    1..24
                          mol_type = other DNA
                          organism = Synthetic construct
SEQUENCE: 510
aggttcatgg ggcaggtagc cttg                                              24

SEQ ID NO: 511            moltype = DNA  length = 24
FEATURE                   Location/Qualifiers
source                    1..24
                          mol_type = other DNA
                          organism = Synthetic construct
SEQUENCE: 511
ggacgacctt accgtcggtg gtct                                              24

SEQ ID NO: 512            moltype = DNA  length = 24
FEATURE                   Location/Qualifiers
source                    1..24
                          mol_type = other DNA
                          organism = Synthetic construct
SEQUENCE: 512
gaccaccgac ggtaaggtcg tcca                                              24

SEQ ID NO: 513            moltype = DNA  length = 24
FEATURE                   Location/Qualifiers
source                    1..24
                          mol_type = other DNA
                          organism = Synthetic construct
SEQUENCE: 513
ggagctctca cgtctacggc ctct                                              24

SEQ ID NO: 514            moltype = DNA  length = 24
FEATURE                   Location/Qualifiers
source                    1..24
                          mol_type = other DNA
                          organism = Synthetic construct
SEQUENCE: 514
gaggccgtag acgtgagagc tccc                                              24

SEQ ID NO: 515            moltype = DNA  length = 24
FEATURE                   Location/Qualifiers
source                    1..24
                          mol_type = other DNA
                          organism = Synthetic construct
SEQUENCE: 515
gaggtcgttc ttgcggatgg gcag                                              24

SEQ ID NO: 516            moltype = DNA  length = 24
FEATURE                   Location/Qualifiers
source                    1..24
                          mol_type = other DNA
                          organism = Synthetic construct
SEQUENCE: 516
tgcccatccg caagaacgac ctcc                                              24

SEQ ID NO: 517            moltype = DNA  length = 24
FEATURE                   Location/Qualifiers
source                    1..24
                          mol_type = other DNA
                          organism = Synthetic construct
SEQUENCE: 517
cgagcactcc gacctcttct atgg                                              24

SEQ ID NO: 518            moltype = DNA  length = 24
FEATURE                   Location/Qualifiers
source                    1..24
                          mol_type = other DNA
                          organism = Synthetic construct
SEQUENCE: 518
catagaagag gtcggagtgc tcgt                                              24

SEQ ID NO: 519            moltype = DNA  length = 24
FEATURE                   Location/Qualifiers
source                    1..24
                          mol_type = other DNA
                          organism = Synthetic construct
SEQUENCE: 519
tcgggctcct ggtttcggct gaga                                              24
```

```
SEQ ID NO: 520          moltype = DNA  length = 24
FEATURE                 Location/Qualifiers
source                  1..24
                        mol_type = other DNA
                        organism = Synthetic construct
SEQUENCE: 520
ctcagccgaa accaggagcc cgat                                              24

SEQ ID NO: 521          moltype = DNA  length = 24
FEATURE                 Location/Qualifiers
source                  1..24
                        mol_type = other DNA
                        organism = Synthetic construct
SEQUENCE: 521
tacatgaggc tcacgtacac tcct                                              24

SEQ ID NO: 522          moltype = DNA  length = 24
FEATURE                 Location/Qualifiers
source                  1..24
                        mol_type = other DNA
                        organism = Synthetic construct
SEQUENCE: 522
ggagtgtacg tgagcctcat gtac                                              24

SEQ ID NO: 523          moltype = DNA  length = 24
FEATURE                 Location/Qualifiers
source                  1..24
                        mol_type = other DNA
                        organism = Synthetic construct
SEQUENCE: 523
cgcggaggct tatgctgatt cgtt                                              24

SEQ ID NO: 524          moltype = DNA  length = 24
FEATURE                 Location/Qualifiers
source                  1..24
                        mol_type = other DNA
                        organism = Synthetic construct
SEQUENCE: 524
acgaatcagc ataagcctcc gcga                                              24

SEQ ID NO: 525          moltype = DNA  length = 24
FEATURE                 Location/Qualifiers
source                  1..24
                        mol_type = other DNA
                        organism = Synthetic construct
SEQUENCE: 525
cacatgaacc cgtatcgcga gatg                                              24

SEQ ID NO: 526          moltype = DNA  length = 24
FEATURE                 Location/Qualifiers
source                  1..24
                        mol_type = other DNA
                        organism = Synthetic construct
SEQUENCE: 526
atctcgcgat acgggttcat gtgt                                              24

SEQ ID NO: 527          moltype = DNA  length = 24
FEATURE                 Location/Qualifiers
source                  1..24
                        mol_type = other DNA
                        organism = Synthetic construct
SEQUENCE: 527
tctttatcac agtggatgca tatg                                              24

SEQ ID NO: 528          moltype = DNA  length = 24
FEATURE                 Location/Qualifiers
source                  1..24
                        mol_type = other DNA
                        organism = Synthetic construct
SEQUENCE: 528
atatgcatcc actgtgataa agaa                                              24

SEQ ID NO: 529          moltype = DNA  length = 24
FEATURE                 Location/Qualifiers
source                  1..24
                        mol_type = other DNA
                        organism = Synthetic construct
SEQUENCE: 529
```

```
acagatggtt agcgagtgac agta                                              24

SEQ ID NO: 530          moltype = DNA   length = 24
FEATURE                 Location/Qualifiers
source                  1..24
                        mol_type = other DNA
                        organism = Synthetic construct
SEQUENCE: 530
actgtcactc gctaaccatc tgtt                                              24

SEQ ID NO: 531          moltype = DNA   length = 24
FEATURE                 Location/Qualifiers
source                  1..24
                        mol_type = other DNA
                        organism = Synthetic construct
SEQUENCE: 531
agttgtccga cacttcatcg gtaa                                              24

SEQ ID NO: 532          moltype = DNA   length = 24
FEATURE                 Location/Qualifiers
source                  1..24
                        mol_type = other DNA
                        organism = Synthetic construct
SEQUENCE: 532
taccgatgaa gtgtcggaca actt                                              24

SEQ ID NO: 533          moltype = DNA   length = 24
FEATURE                 Location/Qualifiers
source                  1..24
                        mol_type = other DNA
                        organism = Synthetic construct
SEQUENCE: 533
accgagtgaa tggaagaaaa acga                                              24

SEQ ID NO: 534          moltype = DNA   length = 24
FEATURE                 Location/Qualifiers
source                  1..24
                        mol_type = other DNA
                        organism = Synthetic construct
SEQUENCE: 534
cgttttctt ccattcactc ggtt                                               24

SEQ ID NO: 535          moltype = DNA   length = 24
FEATURE                 Location/Qualifiers
source                  1..24
                        mol_type = other DNA
                        organism = Synthetic construct
SEQUENCE: 535
acagcaggtt ttcttaaaaa acgt                                              24

SEQ ID NO: 536          moltype = DNA   length = 24
FEATURE                 Location/Qualifiers
source                  1..24
                        mol_type = other DNA
                        organism = Synthetic construct
SEQUENCE: 536
cgtttttaa gaaaacctgc tgtg                                               24

SEQ ID NO: 537          moltype = DNA   length = 24
FEATURE                 Location/Qualifiers
source                  1..24
                        mol_type = other DNA
                        organism = Synthetic construct
SEQUENCE: 537
ttaagaagag accaaaatat ggtc                                              24

SEQ ID NO: 538          moltype = DNA   length = 24
FEATURE                 Location/Qualifiers
source                  1..24
                        mol_type = other DNA
                        organism = Synthetic construct
SEQUENCE: 538
accatatttt ggtctcttct taat                                              24

SEQ ID NO: 539          moltype = DNA   length = 24
FEATURE                 Location/Qualifiers
source                  1..24
                        mol_type = other DNA
                        organism = Synthetic construct
```

```
SEQUENCE: 539
ttctaaacat tagttctcat cacc                                              24

SEQ ID NO: 540          moltype = DNA   length = 24
FEATURE                 Location/Qualifiers
source                  1..24
                        mol_type = other DNA
                        organism = Synthetic construct
SEQUENCE: 540
gtgatgagaa ctaatgttta gaaa                                              24

SEQ ID NO: 541          moltype = DNA   length = 24
FEATURE                 Location/Qualifiers
source                  1..24
                        mol_type = other DNA
                        organism = Synthetic construct
SEQUENCE: 541
catctagttt gcaacggtcc agtt                                              24

SEQ ID NO: 542          moltype = DNA   length = 24
FEATURE                 Location/Qualifiers
source                  1..24
                        mol_type = other DNA
                        organism = Synthetic construct
SEQUENCE: 542
actggaccgt tgcaaactag atgg                                              24

SEQ ID NO: 543          moltype = DNA   length = 24
FEATURE                 Location/Qualifiers
source                  1..24
                        mol_type = other DNA
                        organism = Synthetic construct
SEQUENCE: 543
gactcgcagc gagagaattt tttt                                              24

SEQ ID NO: 544          moltype = DNA   length = 24
FEATURE                 Location/Qualifiers
source                  1..24
                        mol_type = other DNA
                        organism = Synthetic construct
SEQUENCE: 544
aaaaaattct ctcgctgcga gtcc                                              24

SEQ ID NO: 545          moltype = DNA   length = 24
FEATURE                 Location/Qualifiers
source                  1..24
                        mol_type = other DNA
                        organism = Synthetic construct
SEQUENCE: 545
attcactttc ggacaaatcg aact                                              24

SEQ ID NO: 546          moltype = DNA   length = 24
FEATURE                 Location/Qualifiers
source                  1..24
                        mol_type = other DNA
                        organism = Synthetic construct
SEQUENCE: 546
gttcgatttg tccgaaagtg aatt                                              24

SEQ ID NO: 547          moltype = DNA   length = 24
FEATURE                 Location/Qualifiers
source                  1..24
                        mol_type = other DNA
                        organism = Synthetic construct
SEQUENCE: 547
aaccatgaga ccttttcgcc gcag                                              24

SEQ ID NO: 548          moltype = DNA   length = 24
FEATURE                 Location/Qualifiers
source                  1..24
                        mol_type = other DNA
                        organism = Synthetic construct
SEQUENCE: 548
tgcggcgaaa aggtctcatg gtta                                              24

SEQ ID NO: 549          moltype = DNA   length = 24
FEATURE                 Location/Qualifiers
source                  1..24
                        mol_type = other DNA
```

```
                              organism = Synthetic construct
SEQUENCE: 549
ggccgttaga ttttagtgac gatg                                              24

SEQ ID NO: 550            moltype = DNA   length = 24
FEATURE                   Location/Qualifiers
source                    1..24
                          mol_type = other DNA
                          organism = Synthetic construct
SEQUENCE: 550
atcgtcacta aaatctaacg gccg                                              24

SEQ ID NO: 551            moltype = DNA   length = 24
FEATURE                   Location/Qualifiers
source                    1..24
                          mol_type = other DNA
                          organism = Synthetic construct
SEQUENCE: 551
gcaacgtgcc gcatgcatcc attc                                              24

SEQ ID NO: 552            moltype = DNA   length = 24
FEATURE                   Location/Qualifiers
source                    1..24
                          mol_type = other DNA
                          organism = Synthetic construct
SEQUENCE: 552
aatggatgca tgcggcacgt tgcg                                              24

SEQ ID NO: 553            moltype = DNA   length = 24
FEATURE                   Location/Qualifiers
source                    1..24
                          mol_type = other DNA
                          organism = Synthetic construct
SEQUENCE: 553
acagtacatg taggagtact gtgc                                              24

SEQ ID NO: 554            moltype = DNA   length = 24
FEATURE                   Location/Qualifiers
source                    1..24
                          mol_type = other DNA
                          organism = Synthetic construct
SEQUENCE: 554
cacagtactc ctacatgtac tgtg                                              24

SEQ ID NO: 555            moltype = DNA   length = 24
FEATURE                   Location/Qualifiers
source                    1..24
                          mol_type = other DNA
                          organism = Synthetic construct
SEQUENCE: 555
acattcagtc tctctcacta gttg                                              24

SEQ ID NO: 556            moltype = DNA   length = 24
FEATURE                   Location/Qualifiers
source                    1..24
                          mol_type = other DNA
                          organism = Synthetic construct
SEQUENCE: 556
aactagtgag agagactgaa tgta                                              24

SEQ ID NO: 557            moltype = DNA   length = 24
FEATURE                   Location/Qualifiers
source                    1..24
                          mol_type = other DNA
                          organism = Synthetic construct
SEQUENCE: 557
ctacaaagac atgagctgcc ggga                                              24

SEQ ID NO: 558            moltype = DNA   length = 24
FEATURE                   Location/Qualifiers
source                    1..24
                          mol_type = other DNA
                          organism = Synthetic construct
SEQUENCE: 558
cccggcagct catgtctttg tagc                                              24

SEQ ID NO: 559            moltype = DNA   length = 24
FEATURE                   Location/Qualifiers
source                    1..24
```

```
                              mol_type = other DNA
                              organism = Synthetic construct
SEQUENCE: 559
gagcgagcga gcctgacggt ctca                                              24

SEQ ID NO: 560                moltype = DNA  length = 24
FEATURE                       Location/Qualifiers
source                        1..24
                              mol_type = other DNA
                              organism = Synthetic construct
SEQUENCE: 560
gagaccgtca ggctcgctcg ctcc                                              24

SEQ ID NO: 561                moltype = DNA  length = 24
FEATURE                       Location/Qualifiers
source                        1..24
                              mol_type = other DNA
                              organism = Synthetic construct
SEQUENCE: 561
actcccaagc caattattat aaga                                              24

SEQ ID NO: 562                moltype = DNA  length = 24
FEATURE                       Location/Qualifiers
source                        1..24
                              mol_type = other DNA
                              organism = Synthetic construct
SEQUENCE: 562
cttataataa ttggcttggg agtg                                              24

SEQ ID NO: 563                moltype = DNA  length = 24
FEATURE                       Location/Qualifiers
source                        1..24
                              mol_type = other DNA
                              organism = Synthetic construct
SEQUENCE: 563
actccagctc ttaaccaatc cact                                              24

SEQ ID NO: 564                moltype = DNA  length = 24
FEATURE                       Location/Qualifiers
source                        1..24
                              mol_type = other DNA
                              organism = Synthetic construct
SEQUENCE: 564
gtggattggt taagagctgg agtt                                              24

SEQ ID NO: 565                moltype = DNA  length = 24
FEATURE                       Location/Qualifiers
source                        1..24
                              mol_type = other DNA
                              organism = Synthetic construct
SEQUENCE: 565
cacctcctct gctttgctct gcca                                              24

SEQ ID NO: 566                moltype = DNA  length = 24
FEATURE                       Location/Qualifiers
source                        1..24
                              mol_type = other DNA
                              organism = Synthetic construct
SEQUENCE: 566
ggcagagcaa agcagaggag gtgg                                              24

SEQ ID NO: 567                moltype = DNA  length = 24
FEATURE                       Location/Qualifiers
source                        1..24
                              mol_type = other DNA
                              organism = Synthetic construct
SEQUENCE: 567
gggggcagag gagctccccc tccc                                              24

SEQ ID NO: 568                moltype = DNA  length = 24
FEATURE                       Location/Qualifiers
source                        1..24
                              mol_type = other DNA
                              organism = Synthetic construct
SEQUENCE: 568
ggaggggggag ctcctctgcc cccc                                             24

SEQ ID NO: 569                moltype = DNA  length = 24
FEATURE                       Location/Qualifiers
```

```
source                  1..24
                        mol_type = other DNA
                        organism = Synthetic construct
SEQUENCE: 569
tcgccatgtc tagcagcgac ccgg                                              24

SEQ ID NO: 570          moltype = DNA   length = 24
FEATURE                 Location/Qualifiers
source                  1..24
                        mol_type = other DNA
                        organism = Synthetic construct
SEQUENCE: 570
cgggtcgctg ctagacatgg cgag                                              24

SEQ ID NO: 571          moltype = DNA   length = 24
FEATURE                 Location/Qualifiers
source                  1..24
                        mol_type = other DNA
                        organism = Synthetic construct
SEQUENCE: 571
gcgcgtcgtc gttctcggtt cgcc                                              24

SEQ ID NO: 572          moltype = DNA   length = 24
FEATURE                 Location/Qualifiers
source                  1..24
                        mol_type = other DNA
                        organism = Synthetic construct
SEQUENCE: 572
gcgaaccgag aacgacgacg cgcg                                              24

SEQ ID NO: 573          moltype = DNA   length = 24
FEATURE                 Location/Qualifiers
source                  1..24
                        mol_type = other DNA
                        organism = Synthetic construct
SEQUENCE: 573
ggcgacgagt gggcccggcc cgag                                              24

SEQ ID NO: 574          moltype = DNA   length = 24
FEATURE                 Location/Qualifiers
source                  1..24
                        mol_type = other DNA
                        organism = Synthetic construct
SEQUENCE: 574
tcgggccggg cccactcgtc gccg                                              24

SEQ ID NO: 575          moltype = DNA   length = 24
FEATURE                 Location/Qualifiers
source                  1..24
                        mol_type = other DNA
                        organism = Synthetic construct
SEQUENCE: 575
atctgccgtc tcccgcccac cagc                                              24

SEQ ID NO: 576          moltype = DNA   length = 24
FEATURE                 Location/Qualifiers
source                  1..24
                        mol_type = other DNA
                        organism = Synthetic construct
SEQUENCE: 576
ctggtgggcg ggagacggca gatg                                              24

SEQ ID NO: 577          moltype = DNA   length = 24
FEATURE                 Location/Qualifiers
source                  1..24
                        mol_type = other DNA
                        organism = Synthetic construct
SEQUENCE: 577
agccgggcaa ccggaagcag caga                                              24

SEQ ID NO: 578          moltype = DNA   length = 24
FEATURE                 Location/Qualifiers
source                  1..24
                        mol_type = other DNA
                        organism = Synthetic construct
SEQUENCE: 578
ctgctgcttc cggttgcccg gcta                                              24

SEQ ID NO: 579          moltype = DNA   length = 24
```

```
FEATURE                 Location/Qualifiers
source                  1..24
                        mol_type = other DNA
                        organism = Synthetic construct
SEQUENCE: 579
cctgctcctg ctggccgcag cagc                                              24

SEQ ID NO: 580          moltype = DNA   length = 24
FEATURE                 Location/Qualifiers
source                  1..24
                        mol_type = other DNA
                        organism = Synthetic construct
SEQUENCE: 580
ctgctgcggc cagcaggagc aggg                                              24

SEQ ID NO: 581          moltype = DNA   length = 24
FEATURE                 Location/Qualifiers
source                  1..24
                        mol_type = other DNA
                        organism = Synthetic construct
SEQUENCE: 581
cgcctactac atctgccggt ggcg                                              24

SEQ ID NO: 582          moltype = DNA   length = 24
FEATURE                 Location/Qualifiers
source                  1..24
                        mol_type = other DNA
                        organism = Synthetic construct
SEQUENCE: 582
gccaccggca gatgtagtag gcgt                                              24

SEQ ID NO: 583          moltype = DNA   length = 24
FEATURE                 Location/Qualifiers
source                  1..24
                        mol_type = other DNA
                        organism = Synthetic construct
SEQUENCE: 583
tcctccttct tcgcctcccc ctcc                                              24

SEQ ID NO: 584          moltype = DNA   length = 24
FEATURE                 Location/Qualifiers
source                  1..24
                        mol_type = other DNA
                        organism = Synthetic construct
SEQUENCE: 584
gaggggagg cgaagaagga ggag                                               24

SEQ ID NO: 585          moltype = DNA   length = 24
FEATURE                 Location/Qualifiers
source                  1..24
                        mol_type = other DNA
                        organism = Synthetic construct
SEQUENCE: 585
ggtttaaaaa agatttcttt tttt                                              24

SEQ ID NO: 586          moltype = DNA   length = 24
FEATURE                 Location/Qualifiers
source                  1..24
                        mol_type = other DNA
                        organism = Synthetic construct
SEQUENCE: 586
aaaaagaaa tctttttaa acct                                                24

SEQ ID NO: 587          moltype = DNA   length = 24
FEATURE                 Location/Qualifiers
source                  1..24
                        mol_type = other DNA
                        organism = Synthetic construct
SEQUENCE: 587
gtaatcgaca cactaatgca aaga                                              24

SEQ ID NO: 588          moltype = DNA   length = 24
FEATURE                 Location/Qualifiers
source                  1..24
                        mol_type = other DNA
                        organism = Synthetic construct
SEQUENCE: 588
ctttgcatta gtgtgtcgat tact                                              24
```

```
SEQ ID NO: 589          moltype = DNA   length = 24
FEATURE                 Location/Qualifiers
source                  1..24
                        mol_type = other DNA
                        organism = Synthetic construct
SEQUENCE: 589
aacatcttgg acctaaataa ttgt                                              24

SEQ ID NO: 590          moltype = DNA   length = 24
FEATURE                 Location/Qualifiers
source                  1..24
                        mol_type = other DNA
                        organism = Synthetic construct
SEQUENCE: 590
caattattta ggtccaagat gttt                                              24

SEQ ID NO: 591          moltype = DNA   length = 24
FEATURE                 Location/Qualifiers
source                  1..24
                        mol_type = other DNA
                        organism = Synthetic construct
SEQUENCE: 591
ctttccattt tcatctttaa atat                                              24

SEQ ID NO: 592          moltype = DNA   length = 24
FEATURE                 Location/Qualifiers
source                  1..24
                        mol_type = other DNA
                        organism = Synthetic construct
SEQUENCE: 592
tatttaaaga tgaaaatgga aagg                                              24

SEQ ID NO: 593          moltype = DNA   length = 24
FEATURE                 Location/Qualifiers
source                  1..24
                        mol_type = other DNA
                        organism = Synthetic construct
SEQUENCE: 593
acaatttttt tttgggctaa aatg                                              24

SEQ ID NO: 594          moltype = DNA   length = 24
FEATURE                 Location/Qualifiers
source                  1..24
                        mol_type = other DNA
                        organism = Synthetic construct
SEQUENCE: 594
attttagccc aaaaaaaaat tgtg                                              24

SEQ ID NO: 595          moltype = DNA   length = 24
FEATURE                 Location/Qualifiers
source                  1..24
                        mol_type = other DNA
                        organism = Synthetic construct
SEQUENCE: 595
tggtggagtt atgaccacat attg                                              24

SEQ ID NO: 596          moltype = DNA   length = 24
FEATURE                 Location/Qualifiers
source                  1..24
                        mol_type = other DNA
                        organism = Synthetic construct
SEQUENCE: 596
aatatgtggt cataactcca ccat                                              24

SEQ ID NO: 597          moltype = DNA   length = 24
FEATURE                 Location/Qualifiers
source                  1..24
                        mol_type = other DNA
                        organism = Synthetic construct
SEQUENCE: 597
agtgctcaaa aggagagtct actg                                              24

SEQ ID NO: 598          moltype = DNA   length = 24
FEATURE                 Location/Qualifiers
source                  1..24
                        mol_type = other DNA
                        organism = Synthetic construct
SEQUENCE: 598
agtagactct ccttttgagc actt                                              24
```

```
SEQ ID NO: 599         moltype = DNA  length = 24
FEATURE                Location/Qualifiers
source                 1..24
                       mol_type = other DNA
                       organism = Synthetic construct
SEQUENCE: 599
ccaccacaag tactatgcaa caaa                                              24

SEQ ID NO: 600         moltype = DNA  length = 24
FEATURE                Location/Qualifiers
source                 1..24
                       mol_type = other DNA
                       organism = Synthetic construct
SEQUENCE: 600
ttgttgcata gtacttgtgg tgga                                              24

SEQ ID NO: 601         moltype = DNA  length = 24
FEATURE                Location/Qualifiers
source                 1..24
                       mol_type = other DNA
                       organism = Synthetic construct
SEQUENCE: 601
aagaaaatgg aaactttcct ctct                                              24

SEQ ID NO: 602         moltype = DNA  length = 24
FEATURE                Location/Qualifiers
source                 1..24
                       mol_type = other DNA
                       organism = Synthetic construct
SEQUENCE: 602
gagagaaaag tttccatttt cttg                                              24

SEQ ID NO: 603         moltype = DNA  length = 24
FEATURE                Location/Qualifiers
source                 1..24
                       mol_type = other DNA
                       organism = Synthetic construct
SEQUENCE: 603
cactagctgt ttacatggtg agca                                              24

SEQ ID NO: 604         moltype = DNA  length = 24
FEATURE                Location/Qualifiers
source                 1..24
                       mol_type = other DNA
                       organism = Synthetic construct
SEQUENCE: 604
gctcaccatg taaacagcta gtga                                              24

SEQ ID NO: 605         moltype = DNA  length = 24
FEATURE                Location/Qualifiers
source                 1..24
                       mol_type = other DNA
                       organism = Synthetic construct
SEQUENCE: 605
agaaatactt agtatatatc tata                                              24

SEQ ID NO: 606         moltype = DNA  length = 24
FEATURE                Location/Qualifiers
source                 1..24
                       mol_type = other DNA
                       organism = Synthetic construct
SEQUENCE: 606
atagatatat actaagtatt tcta                                              24

SEQ ID NO: 607         moltype = DNA  length = 24
FEATURE                Location/Qualifiers
source                 1..24
                       mol_type = other DNA
                       organism = Synthetic construct
SEQUENCE: 607
acttttcatt ctgtaattct ttaa                                              24

SEQ ID NO: 608         moltype = DNA  length = 24
FEATURE                Location/Qualifiers
source                 1..24
                       mol_type = other DNA
                       organism = Synthetic construct
SEQUENCE: 608
```

```
taaagaatta cagaatgaaa agtg                                              24

SEQ ID NO: 609          moltype = DNA   length = 24
FEATURE                 Location/Qualifiers
source                  1..24
                        mol_type = other DNA
                        organism = Synthetic construct
SEQUENCE: 609
ctgtttaaag cttgattttt ttta                                              24

SEQ ID NO: 610          moltype = DNA   length = 24
FEATURE                 Location/Qualifiers
source                  1..24
                        mol_type = other DNA
                        organism = Synthetic construct
SEQUENCE: 610
aaaaaaaatc aagctttaaa cagt                                              24

SEQ ID NO: 611          moltype = DNA   length = 24
FEATURE                 Location/Qualifiers
source                  1..24
                        mol_type = other DNA
                        organism = Synthetic construct
SEQUENCE: 611
atgttctgct tcatttgtgt tgaa                                              24

SEQ ID NO: 612          moltype = DNA   length = 24
FEATURE                 Location/Qualifiers
source                  1..24
                        mol_type = other DNA
                        organism = Synthetic construct
SEQUENCE: 612
tcaacacaaa tgaagcagaa catg                                              24

SEQ ID NO: 613          moltype = DNA   length = 24
FEATURE                 Location/Qualifiers
source                  1..24
                        mol_type = other DNA
                        organism = Synthetic construct
SEQUENCE: 613
attggggaac tttcttgaat ccag                                              24

SEQ ID NO: 614          moltype = DNA   length = 24
FEATURE                 Location/Qualifiers
source                  1..24
                        mol_type = other DNA
                        organism = Synthetic construct
SEQUENCE: 614
tggattcaag aaagttcccc aatt                                              24

SEQ ID NO: 615          moltype = DNA   length = 24
FEATURE                 Location/Qualifiers
source                  1..24
                        mol_type = other DNA
                        organism = Synthetic construct
SEQUENCE: 615
catttgaagt tttcttgaaa caaa                                              24

SEQ ID NO: 616          moltype = DNA   length = 24
FEATURE                 Location/Qualifiers
source                  1..24
                        mol_type = other DNA
                        organism = Synthetic construct
SEQUENCE: 616
ttgtttcaag aaaacttcaa atgg                                              24

SEQ ID NO: 617          moltype = DNA   length = 24
FEATURE                 Location/Qualifiers
source                  1..24
                        mol_type = other DNA
                        organism = Synthetic construct
SEQUENCE: 617
cattaccctg ttggaaaaag atgg                                              24

SEQ ID NO: 618          moltype = DNA   length = 24
FEATURE                 Location/Qualifiers
source                  1..24
                        mol_type = other DNA
                        organism = Synthetic construct
```

```
SEQUENCE: 618
catctttttc caacagggta atga                                         24

SEQ ID NO: 619         moltype = DNA   length = 24
FEATURE                Location/Qualifiers
source                 1..24
                       mol_type = other DNA
                       organism = Synthetic construct
SEQUENCE: 619
tactttgttg aaacccccaa ataa                                         24

SEQ ID NO: 620         moltype = DNA   length = 24
FEATURE                Location/Qualifiers
source                 1..24
                       mol_type = other DNA
                       organism = Synthetic construct
SEQUENCE: 620
tatttggggt tttcaacaaa gtat                                         24

SEQ ID NO: 621         moltype = DNA   length = 24
FEATURE                Location/Qualifiers
source                 1..24
                       mol_type = other DNA
                       organism = Synthetic construct
SEQUENCE: 621
cttgaatttc tgaacccaca tcat                                         24

SEQ ID NO: 622         moltype = DNA   length = 24
FEATURE                Location/Qualifiers
source                 1..24
                       mol_type = other DNA
                       organism = Synthetic construct
SEQUENCE: 622
tgatgtgggt tcagaaattc aagg                                         24

SEQ ID NO: 623         moltype = DNA   length = 24
FEATURE                Location/Qualifiers
source                 1..24
                       mol_type = other DNA
                       organism = Synthetic construct
SEQUENCE: 623
gttttgctgt taaagctagt acct                                         24

SEQ ID NO: 624         moltype = DNA   length = 24
FEATURE                Location/Qualifiers
source                 1..24
                       mol_type = other DNA
                       organism = Synthetic construct
SEQUENCE: 624
ggtactagct ttaacagcaa aacc                                         24

SEQ ID NO: 625         moltype = DNA   length = 24
FEATURE                Location/Qualifiers
source                 1..24
                       mol_type = other DNA
                       organism = Synthetic construct
SEQUENCE: 625
ggttctagga agttttgtga aact                                         24

SEQ ID NO: 626         moltype = DNA   length = 24
FEATURE                Location/Qualifiers
source                 1..24
                       mol_type = other DNA
                       organism = Synthetic construct
SEQUENCE: 626
gtttcacaaa acttcctaga acca                                         24

SEQ ID NO: 627         moltype = DNA   length = 24
FEATURE                Location/Qualifiers
source                 1..24
                       mol_type = other DNA
                       organism = Synthetic construct
SEQUENCE: 627
tgggtagaag tgtttgtgtt aagg                                         24

SEQ ID NO: 628         moltype = DNA   length = 24
FEATURE                Location/Qualifiers
source                 1..24
                       mol_type = other DNA
```

-continued

```
                        organism = Synthetic construct
SEQUENCE: 628
cttaacacaa acacttctac ccaa                                              24

SEQ ID NO: 629          moltype = DNA   length = 24
FEATURE                 Location/Qualifiers
source                  1..24
                        mol_type = other DNA
                        organism = Synthetic construct
SEQUENCE: 629
tagtagtagt gctcttttag agct                                              24

SEQ ID NO: 630          moltype = DNA   length = 24
FEATURE                 Location/Qualifiers
source                  1..24
                        mol_type = other DNA
                        organism = Synthetic construct
SEQUENCE: 630
gctctaaaag agcactacta ctac                                              24

SEQ ID NO: 631          moltype = DNA   length = 24
FEATURE                 Location/Qualifiers
source                  1..24
                        mol_type = other DNA
                        organism = Synthetic construct
SEQUENCE: 631
gtacctgaga ccaaaaagga gaat                                              24

SEQ ID NO: 632          moltype = DNA   length = 24
FEATURE                 Location/Qualifiers
source                  1..24
                        mol_type = other DNA
                        organism = Synthetic construct
SEQUENCE: 632
ttctcctttt tggtctcagg taca                                              24

SEQ ID NO: 633          moltype = DNA   length = 24
FEATURE                 Location/Qualifiers
source                  1..24
                        mol_type = other DNA
                        organism = Synthetic construct
SEQUENCE: 633
ttgattttga gcttcctatg tatg                                              24

SEQ ID NO: 634          moltype = DNA   length = 24
FEATURE                 Location/Qualifiers
source                  1..24
                        mol_type = other DNA
                        organism = Synthetic construct
SEQUENCE: 634
atacatagga agctcaaaat caag                                              24

SEQ ID NO: 635          moltype = DNA   length = 24
FEATURE                 Location/Qualifiers
source                  1..24
                        mol_type = other DNA
                        organism = Synthetic construct
SEQUENCE: 635
cttgctgtgg ttggtggtgg ccct                                              24

SEQ ID NO: 636          moltype = DNA   length = 24
FEATURE                 Location/Qualifiers
source                  1..24
                        mol_type = other DNA
                        organism = Synthetic construct
SEQUENCE: 636
gggccaccac caaccacagc aaga                                              24

SEQ ID NO: 637          moltype = DNA   length = 24
FEATURE                 Location/Qualifiers
source                  1..24
                        mol_type = other DNA
                        organism = Synthetic construct
SEQUENCE: 637
caggacttgc tgttgcacag caag                                              24

SEQ ID NO: 638          moltype = DNA   length = 24
FEATURE                 Location/Qualifiers
source                  1..24
```

-continued

```
                          mol_type = other DNA
                          organism = Synthetic construct
SEQUENCE: 638
ttgctgtgca acagcaagtc ctgc                                              24

SEQ ID NO: 639            moltype = DNA   length = 24
FEATURE                   Location/Qualifiers
source                    1..24
                          mol_type = other DNA
                          organism = Synthetic construct
SEQUENCE: 639
ttctgaagca ggactctctg tttg                                              24

SEQ ID NO: 640            moltype = DNA   length = 24
FEATURE                   Location/Qualifiers
source                    1..24
                          mol_type = other DNA
                          organism = Synthetic construct
SEQUENCE: 640
aaacagagag tcctgcttca gaaa                                              24

SEQ ID NO: 641            moltype = DNA   length = 24
FEATURE                   Location/Qualifiers
source                    1..24
                          mol_type = other DNA
                          organism = Synthetic construct
SEQUENCE: 641
tcaattgatc cgaatcctaa attg                                              24

SEQ ID NO: 642            moltype = DNA   length = 24
FEATURE                   Location/Qualifiers
source                    1..24
                          mol_type = other DNA
                          organism = Synthetic construct
SEQUENCE: 642
aatttaggat tcggatcaat tgaa                                              24

SEQ ID NO: 643            moltype = DNA   length = 24
FEATURE                   Location/Qualifiers
source                    1..24
                          mol_type = other DNA
                          organism = Synthetic construct
SEQUENCE: 643
tatggcctaa taactatggt gttt                                              24

SEQ ID NO: 644            moltype = DNA   length = 24
FEATURE                   Location/Qualifiers
source                    1..24
                          mol_type = other DNA
                          organism = Synthetic construct
SEQUENCE: 644
aacaccatag ttattaggcc atat                                              24

SEQ ID NO: 645            moltype = DNA   length = 24
FEATURE                   Location/Qualifiers
source                    1..24
                          mol_type = other DNA
                          organism = Synthetic construct
SEQUENCE: 645
ttgttagatt gtctagatgc tacc                                              24

SEQ ID NO: 646            moltype = DNA   length = 24
FEATURE                   Location/Qualifiers
source                    1..24
                          mol_type = other DNA
                          organism = Synthetic construct
SEQUENCE: 646
gtagcatcta gacaatctaa caag                                              24

SEQ ID NO: 647            moltype = DNA   length = 24
FEATURE                   Location/Qualifiers
source                    1..24
                          mol_type = other DNA
                          organism = Synthetic construct
SEQUENCE: 647
ggtctggtgc agcagtgtac attg                                              24

SEQ ID NO: 648            moltype = DNA   length = 24
FEATURE                   Location/Qualifiers
```

```
source                  1..24
                        mol_type = other DNA
                        organism = Synthetic construct
SEQUENCE: 648
aatgtacact gctgcaccag acca                                              24

SEQ ID NO: 649          moltype = DNA   length = 24
FEATURE                 Location/Qualifiers
source                  1..24
                        mol_type = other DNA
                        organism = Synthetic construct
SEQUENCE: 649
tgataatacg gctaaagatc ttca                                              24

SEQ ID NO: 650          moltype = DNA   length = 24
FEATURE                 Location/Qualifiers
source                  1..24
                        mol_type = other DNA
                        organism = Synthetic construct
SEQUENCE: 650
gaagatcttt agccgtatta tcat                                              24

SEQ ID NO: 651          moltype = DNA   length = 24
FEATURE                 Location/Qualifiers
source                  1..24
                        mol_type = other DNA
                        organism = Synthetic construct
SEQUENCE: 651
agaccttatg gaagggttaa ccgg                                              24

SEQ ID NO: 652          moltype = DNA   length = 24
FEATURE                 Location/Qualifiers
source                  1..24
                        mol_type = other DNA
                        organism = Synthetic construct
SEQUENCE: 652
cggttaaccc ttccataagg tcta                                              24

SEQ ID NO: 653          moltype = DNA   length = 24
FEATURE                 Location/Qualifiers
source                  1..24
                        mol_type = other DNA
                        organism = Synthetic construct
SEQUENCE: 653
aacagctgaa atcgaaaatg atgc                                              24

SEQ ID NO: 654          moltype = DNA   length = 24
FEATURE                 Location/Qualifiers
source                  1..24
                        mol_type = other DNA
                        organism = Synthetic construct
SEQUENCE: 654
catcattttc gatttcagct gttt                                              24

SEQ ID NO: 655          moltype = DNA   length = 24
FEATURE                 Location/Qualifiers
source                  1..24
                        mol_type = other DNA
                        organism = Synthetic construct
SEQUENCE: 655
ttccaccaag ccaaagttat aaag                                              24

SEQ ID NO: 656          moltype = DNA   length = 24
FEATURE                 Location/Qualifiers
source                  1..24
                        mol_type = other DNA
                        organism = Synthetic construct
SEQUENCE: 656
tttataactt tggcttggtg gaat                                              24

SEQ ID NO: 657          moltype = DNA   length = 24
FEATURE                 Location/Qualifiers
source                  1..24
                        mol_type = other DNA
                        organism = Synthetic construct
SEQUENCE: 657
tgattcatga ggaatcgaaa tcca                                              24

SEQ ID NO: 658          moltype = DNA   length = 24
```

```
FEATURE                 Location/Qualifiers
source                  1..24
                        mol_type = other DNA
                        organism = Synthetic construct
SEQUENCE: 658
ggatttcgat tcctcatgaa tcac                                              24

SEQ ID NO: 659          moltype = DNA   length = 24
FEATURE                 Location/Qualifiers
source                  1..24
                        mol_type = other DNA
                        organism = Synthetic construct
SEQUENCE: 659
gttgatatgc aatgatggta ttac                                              24

SEQ ID NO: 660          moltype = DNA   length = 24
FEATURE                 Location/Qualifiers
source                  1..24
                        mol_type = other DNA
                        organism = Synthetic construct
SEQUENCE: 660
taataccatc attgcatatc aaca                                              24

SEQ ID NO: 661          moltype = DNA   length = 24
FEATURE                 Location/Qualifiers
source                  1..24
                        mol_type = other DNA
                        organism = Synthetic construct
SEQUENCE: 661
attcaggcaa cggtggtgct cgat                                              24

SEQ ID NO: 662          moltype = DNA   length = 24
FEATURE                 Location/Qualifiers
source                  1..24
                        mol_type = other DNA
                        organism = Synthetic construct
SEQUENCE: 662
tcgagcacca ccgttgcctg aata                                              24

SEQ ID NO: 663          moltype = DNA   length = 24
FEATURE                 Location/Qualifiers
source                  1..24
                        mol_type = other DNA
                        organism = Synthetic construct
SEQUENCE: 663
caactggctt ctctagatct cttg                                              24

SEQ ID NO: 664          moltype = DNA   length = 24
FEATURE                 Location/Qualifiers
source                  1..24
                        mol_type = other DNA
                        organism = Synthetic construct
SEQUENCE: 664
aagagatcta gagaagccag ttgc                                              24

SEQ ID NO: 665          moltype = DNA   length = 24
FEATURE                 Location/Qualifiers
source                  1..24
                        mol_type = other DNA
                        organism = Synthetic construct
SEQUENCE: 665
tcaaaaacct cccacctacc gcgt                                              24

SEQ ID NO: 666          moltype = DNA   length = 24
FEATURE                 Location/Qualifiers
source                  1..24
                        mol_type = other DNA
                        organism = Synthetic construct
SEQUENCE: 666
cgcggtaggt gggaggtttt tgaa                                              24

SEQ ID NO: 667          moltype = RNA   length = 24
FEATURE                 Location/Qualifiers
source                  1..24
                        mol_type = other RNA
                        organism = Synthetic construct
SEQUENCE: 667
tcaaaaacct cccacctacc gcgt                                              24
```

```
SEQ ID NO: 668         moltype = RNA   length = 24
FEATURE                Location/Qualifiers
source                 1..24
                       mol_type = other RNA
                       organism = Synthetic construct
SEQUENCE: 668
cgcggtaggt gggaggtttt tgaa                                              24

SEQ ID NO: 669         moltype = DNA   length = 24
FEATURE                Location/Qualifiers
source                 1..24
                       mol_type = other DNA
                       organism = Synthetic construct
SEQUENCE: 669
tcaaaaacct cccacctacc gcgt                                              24

SEQ ID NO: 670         moltype = DNA   length = 24
FEATURE                Location/Qualifiers
source                 1..24
                       mol_type = other DNA
                       organism = Synthetic construct
SEQUENCE: 670
cgcggtaggt gggaggtttt tgaa                                              24

SEQ ID NO: 671         moltype = DNA   length = 24
FEATURE                Location/Qualifiers
source                 1..24
                       mol_type = other DNA
                       organism = Synthetic construct
SEQUENCE: 671
tcaaaaacct cccacctacc gcgt                                              24

SEQ ID NO: 672         moltype = DNA   length = 24
FEATURE                Location/Qualifiers
source                 1..24
                       mol_type = other DNA
                       organism = Synthetic construct
SEQUENCE: 672
cgcggtaggt gggaggtttt tgaa                                              24

SEQ ID NO: 673         moltype = DNA   length = 24
FEATURE                Location/Qualifiers
source                 1..24
                       mol_type = other DNA
                       organism = Synthetic construct
SEQUENCE: 673
tcaaaaacct cccacctacc gcgt                                              24

SEQ ID NO: 674         moltype = DNA   length = 24
FEATURE                Location/Qualifiers
source                 1..24
                       mol_type = other DNA
                       organism = Synthetic construct
SEQUENCE: 674
cgcggtaggt gggaggtttt tgaa                                              24
```